United States Patent
Ji et al.

(10) Patent No.: US 10,081,812 B2
(45) Date of Patent: Sep. 25, 2018

(54) **D-AMINO ACID-INDUCIBLE GENE EXPRESSION SYSTEM FOR *RHODOSPORIDIUM* AND *RHODOTORULA***

(71) Applicant: TEMASEK LIFE SCIENCES LABORATORY LIMITED, Singapore (SG)

(72) Inventors: Lianghui Ji, Singapore (SG); Yanbin Liu, Singapore (SG); Chong Mei John Koh, Singapore (SG)

(73) Assignee: TEMASEK LIFE SCIENCES LABORATORY LTD, Singapore (SG)

( * ) Notice: Subject to any disclaimer, the term of this patent is extended or adjusted under 35 U.S.C. 154(b) by 0 days.

(21) Appl. No.: 15/563,176

(22) PCT Filed: Mar. 31, 2016

(86) PCT No.: PCT/SG2016/050161
§ 371 (c)(1),
(2) Date: Sep. 29, 2017

(87) PCT Pub. No.: WO2016/159887
PCT Pub. Date: Jun. 10, 2016

(65) Prior Publication Data
US 2018/0073034 A1   Mar. 15, 2018

Related U.S. Application Data

(60) Provisional application No. 62/142,788, filed on Apr. 3, 2015.

(51) Int. Cl.
*C12N 15/81* (2006.01)
*C12N 15/80* (2006.01)
*C12N 1/16* (2006.01)

(52) U.S. Cl.
CPC ............ *C12N 15/815* (2013.01); *C12N 1/16* (2013.01); *C12N 15/80* (2013.01); *C12N 15/81* (2013.01); *C12N 2830/36* (2013.01); *C12N 2840/002* (2013.01)

(58) Field of Classification Search
None
See application file for complete search history.

(56) References Cited

U.S. PATENT DOCUMENTS 6,187,574 B1   2/2001   Garcia Lopez et al.

FOREIGN PATENT DOCUMENTS

WO   98/59037 A1   12/1998

OTHER PUBLICATIONS

International Search Report and Written Opinion for PCT/SG2016/050161 dated Jun. 14, 2016 (10 pages).
GenBank, Database accession No. Z71657.1, Nov. 14, 2006 (3 pages).
Kiyoshi Fukui et al. "Molecular cloning and chromosomal localization of a human gene encoding D-amino acid oxidase", The Journal of Biological Chemistry, Sep. 1992, pp. 18631-18638, vol. 267, No. 26.
Herve Le Hir et al. "How introns influence and enhance eukaryotic gene expression", Trends in Biochemical Sciences, Apr. 2003, pp. 215-220, vol. 28, No. 4.
Yanbin Liu et al. "Engineering an efficient and tight D-amino acid-inducible gene expression system in *Rhodosporidium/Rhodotorula* species", Microbial Cell Factories, Oct. 2015, vol. 14, (17 pages).
Gianluca Molla et al. "Regulation of D-amino acid oxidase expression in the yeast *Rhodotorula gracilis*", Yeast, 2003, pp. 1061-1069, vol. 20, No. 12.
Mirella Pilone Simonetta et al. "Induction of D-amino acid oxidase by D-alanine in Rhodotorula gracilis grown in defined medium", Journal of General Microbiology, 1989, pp. 593-600, vol. 135.
The European Communication with extended European Search Report issued in Application No. 16773586.9 dated Mar. 2, 2018, 9 pages.
Database EMBL [Online]: "Rhodotorula gracilis mRNA for D-amino acid oxidase", XP002778037, retrieved from EBI accession No. EM_STD: Z71657, Jul. 1, 1997, 2 pages.
Database Geneseq [Online]: "Rhodosporidium toruloides D-amino acid oxidase encoding genomic DNA.", XP002778038, retrieved from EBI accession No. GSN: AAX19101, Jun. 4, 1999, 1 page.
Alonso, Jorge et al: "D-amino-acid oxidase gene from *Rhodotorula gracilis* (*Rhodosporidium toruloides*) ATCC 26217", Microbiology (Reading), vol. 144, No. 4, Apr. 1998, XP002778039, pp. 1095-1101.

*Primary Examiner* — James S Ketter
(74) *Attorney, Agent, or Firm* — Rothwell, Figg, Ernst & Manbeck, P.C.

(57) ABSTRACT

The present invention relates to the field of fungal biotechnology, more particularly to a strong inducible gene expression system in fungal species, such as a species of the *Rhodosporidium* genus or the *Rhodotorula* genus.

20 Claims, 10 Drawing Sheets

Specification includes a Sequence Listing.

FIG. 2A

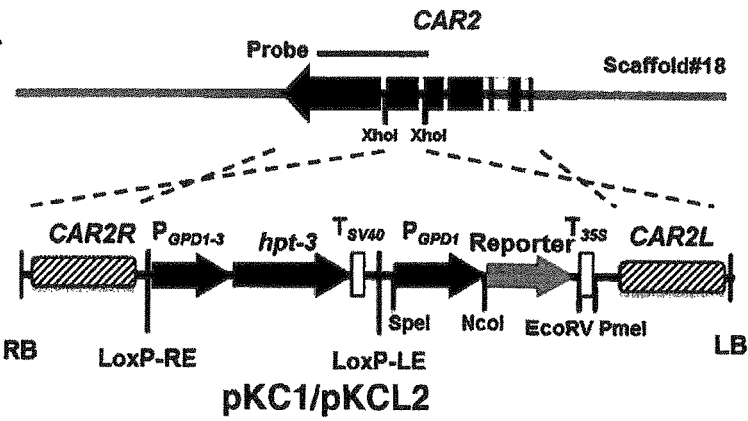

pKC1/pKCL2

FIG. 2B

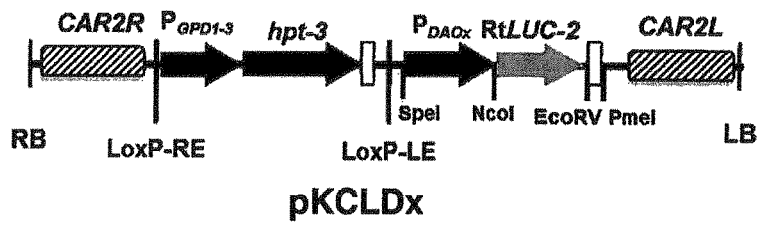

pKCLDx

FIG. 2C

```
-100  tgagcgaagg aagccgcatc gacaagttcg ctcccctttg ccctctttcc
                                           ct box
 -50  gATCACCCGT TCTCGCCTTA CCCGCTCAGA ACAACACCAG ATCACTCACA
      ↑ tsp                            5'UTR
   1  ATgtctgtgc agcatccgcc ctgaacttgc cgcatcgtca gcggtctccc
   P1 M                                 intron 1
  51  tcgccctctg ctgacctcgt ctcgtcacct cctccctcat ccgctcctat
                                intron 1
 101  cgcttcccgt acaccgctgg gatgctcgca gGTCTGCCGG AAAGGGATCT
   P2                                   S  A  G  K  G  S
 151  GTCAACGTCG GAATCAACGG CTTCGGTCGC ATCGGCCGCA TCGTCCTCCG
   P3  V  N  V  G  I  N  G  F  G  R  I  G  R  I  V  L  R
```

FIG. 2D

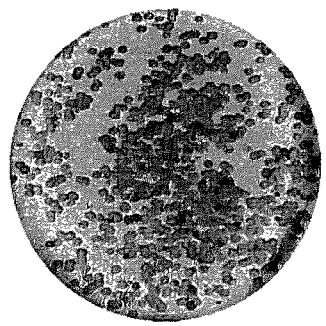

Amino Acid Substitution per 100 residues

Fig. 5 A
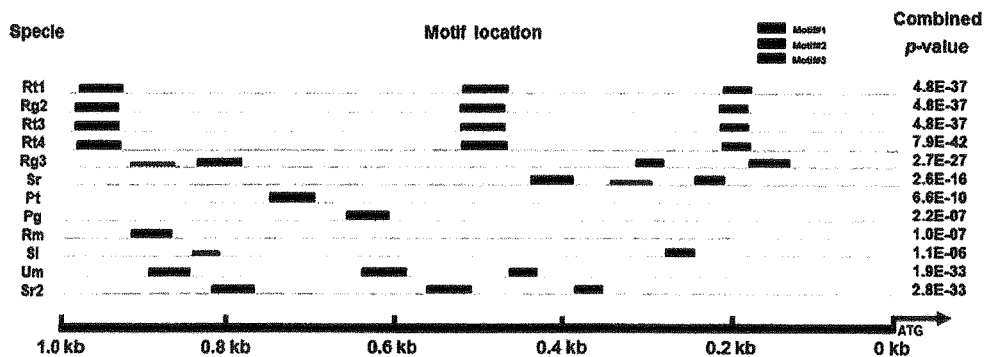
Fig. 5 B
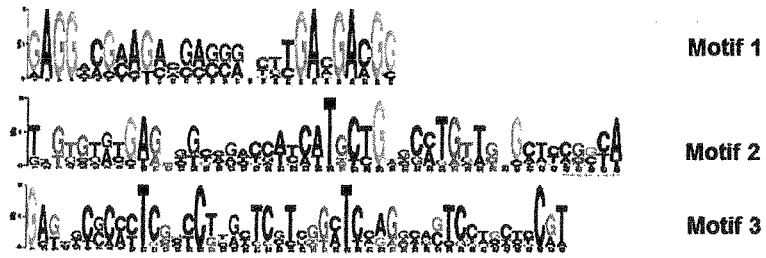
Motif 1
Motif 2
Motif 3
Fig. 5 C
| Name | Start | p-value | Sequence |
|---|---|---|---|
| Rg3 | -307 | 9.8E-14 | GAGGACAAGCCGAGGAACTTGAAGAAGG |
| Um | -468 | 1.5E-13 | GAGGTAGAAGAAGCCGGTCTTGACGACGG |
| Sr2 | -391 | 2.1E-13 | GAGGTAGAACAAGCCCGTCTTGACGACGG |
| Sr | -252 | 2.4E-12 | GAGGACCCAGCCGAGGAACTTGAAGAAGG |
| Rg2 | -222 | 4.2E-12 | GAGGCCGCAGAGCAGCGCTGCGACGACGG |
| Rt1 | -219 | 1.7E-11 | AAGCCCGCACAGCAGCGCTGCGACGACGG |
| Sl | -285 | 1.4E-10 | GAGGACGACTACGACGAGGATGAGGACG- |
AGG--G-AG----------GA-GA-GG

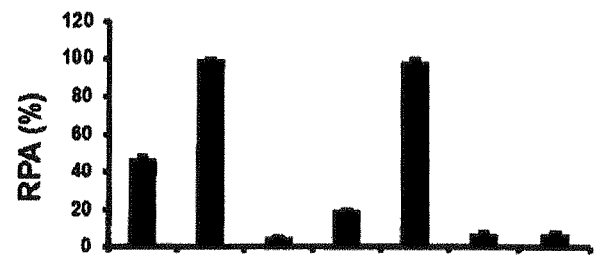
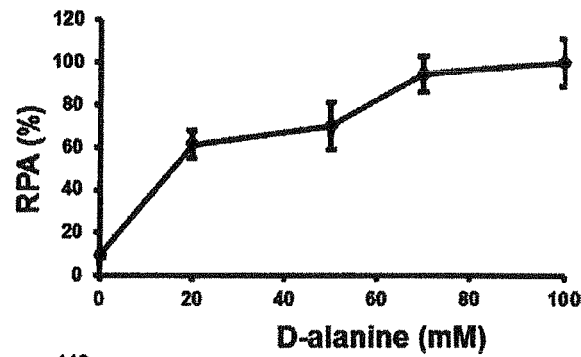
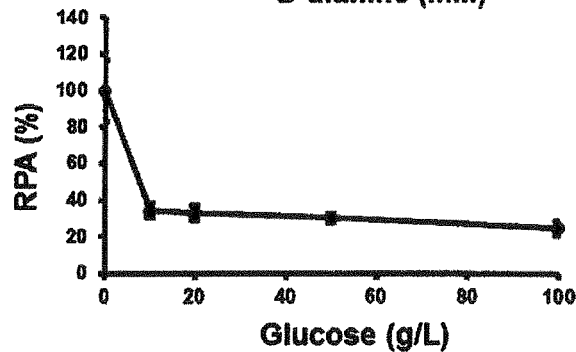
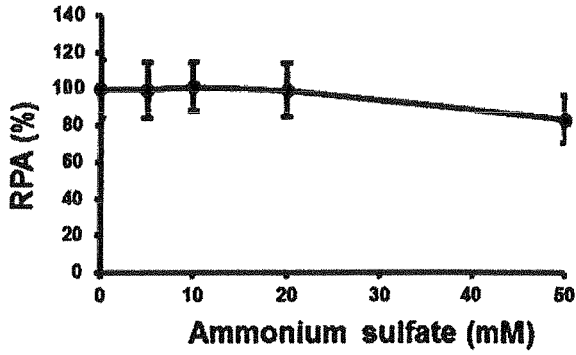

Fig. 9A
| Seq ID | Region | Sequence (5'> 3') |
|---|---|---|
| 56 | 1-50 | GTGCGTC-TTTCCCTCTCCTCCCCACACCCGACAGTTCTCGAGGAGGAGTA |
| 57 | 1-51 | GTGCGTCTTTTCCCTCTCCTCCCCACACCCGACAGTCCTCGACGAGGTGTA |
| 58 | 1-51 | GTGCGTCTTTTCCCTCTCCTCCCCACACCCGACAGTCCTCGACGAGGTGTA |
| 59 | 1-50 | GTGAGCCCCAGCCCTCACACTCTCCCCCTCCCCCCCACTTCCGAGGCCTG |
Fig. 9B
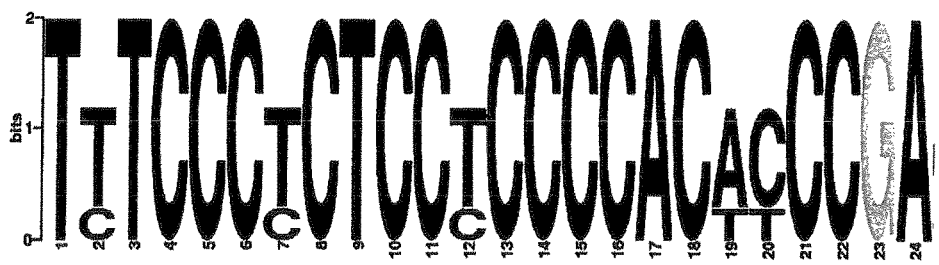
Fig. 9C
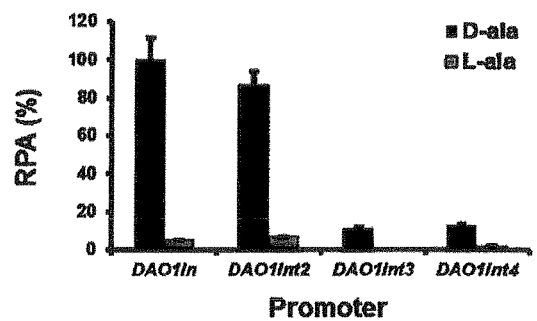

D-AMINO ACID-INDUCIBLE GENE EXPRESSION SYSTEM FOR *RHODOSPORIDIUM* AND *RHODOTORULA*

CROSS-REFERENCE TO RELATED APPLICATIONS

The present application is a national stage filing under 35 U.S.C. § 371 of PCT/SG2016/050161, filed on 31 Mar. 2016, which is related to and claims the benefit of priority to U.S. Provisional Patent Application Ser. No. 62/142,788 filed 3 Apr. 2015. Each application is incorporated herein by reference in its entirety.

SUBMISSION OF SEQUENCE LISTING

The present application is being filed along with a Sequence Listing in electronic format. The Sequence Listing is entitled 2577248PCTSequenceListing.txt, created on 12 Jan. 2016 and is 125 kb in size. The information in the electronic format of the Sequence Listing is incorporated herein by reference in their entirety.

BACKGROUND OF THE INVENTION

The present invention relates to the field of fungal biotechnology, more particularly to a strong inducible gene expression system in fungal species, such as *Rhodosporidium* or *Rhodotorula* genus.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

*Rhodosporidium* and *Rhodotorula* are two closely related genera of fungi belonging to the Pucciniomycotina subphylum of the Basidiomycota. Both are often isolated as oil or carotenoid producing yeast (1). Due to their ability to be cultured to extremely high cell density (>100 g/l dry cell mass) and accumulate more than 60% biomass as triglycerides, *Rhodosporidium* and *Rhodotorula* are fungal hosts with great biotechnological potential (2-4). Towards this goal, we have established efficient systems for genetic transformation, gene knockout and strong constitutive protein expression (5-7). However, there are no effective promoters for gene expression in *Rhodosporidium* and *Rhodotorula* to date. This becomes a major bottleneck in metabolic engineering in these hosts (8-10).

D-Amino acid oxidase (DAAO, EC 1.4.3.3) is a flavoenzyme that specifically catalyzes the oxidative deamination of D-amino acids to $\alpha$-keto acids, ammonia and hydrogen peroxide (FIG. 1). DAAO activity has been widely identified, ranging from bacteria, fungi to animals [11]. DAAO is best known for its use in the production of cephalosporin, an antibiotic with an annual global market of ~200 million US dollars (12).

The *Rhodosporidium toruloides* and *Rhodotorula gracilis*DAAO is a peroxisomal protein that has been well documented since 1987 (13). Recent studies of *R. toruloides* Dao1 mainly focus on its heterologous expression (14), enzyme properties (15-18) and immobilization (19-22). DAO1 mRNA transcripts have been reported to peak within 12-hr after induction with D-alanine and Dao1 protein may account for 1.0% of the soluble intracellular proteins (23), however, there is no information on how the D-amino acid inducible property of the DAO1 gene can be exploited for biotechnological applications.

Small interfering RNA (siRNA) is a class of double-stranded RNA molecules, 20-25 base pairs in length. siRNA interferes with the expression of specific genes with complementary nucleotide sequences causing mRNA to be broken down after transcription resulting in no translation. siRNAs are produced from double-stranded RNAs, e.g., from an inverted repeat of an RNA sequence and typically base-pair perfectly and induce mRNA cleavage only in a single, specific mRNA target (24). MicroRNAs (miRNAs) are genomically encoded non-coding RNAs that help regulate gene expression, particularly during development. Mature miRNAs are structurally similar to siRNAs produced from exogenous dsRNA except that they are expressed from a much longer RNA-coding gene as a primary transcript known as a pri-miRNA which is processed, in the cell nucleus, to a stem-loop structure called a pre-miRNA by the microprocessor complex. A region of the pri-miRNA is partially self-complementary allowing the transcript to fold back onto itself to form a stem-loop structure of imperfectly dsRNA. Artificial miRNA (amiRNA) technology uses endogenous pri-miRNAs, in which the miRNA and miRNA* (passenger strand of the miRNA duplex) sequences have been replaced with corresponding amiRNA/amiRNA* sequences that direct highly efficient RNA silencing of the targeted gene (25). miRNAs typically have incomplete base pairing to a target and inhibit the translation of multiple different mRNAs with similar sequences.

It is desired to identify inducible promoters and create nucleic acid constructs that are useful for introducing into fungal species.

SUMMARY OF THE INVENTION

The present invention relates to the field of fungal biotechnology, more particularly to a strong inducible gene expression system in fungal species, such as *Rhodosporidium* or *Rhodotorula* genus.

Thus, in one aspect, the present invention provides an inducible promoter for expression of a heterologous polynucleotide in a fungal species. In one embodiment, the inducible promoter comprises a nucleotide sequence that has at least 75% identity to the nucleotide set forth in SEQ ID NO:94. In another embodiment, the inducible promoter comprises a nucleotide sequence that has at least 75% identity to the nucleotide set forth in SEQ ID NO:95. In a further embodiment, the inducible promoter comprises a nucleotide sequence that has at least 75% identity to the nucleotide set forth in SEQ ID NO:96. In another embodiment, the inducible promoter comprises a nucleotide sequence that has at least 75% identity to the nucleotide set forth in SEQ ID NO:97. In an additional embodiment, the inducible promoter comprises a nucleotide sequence that has at least 75% identity to the nucleotide set forth in SEQ ID NO:5. In some embodiments, the promoter includes a DNA motif, sometimes referred to herein as the promoter DNA motif. In one embodiment, the promoter DNA motif comprises the consensus sequence AGGNNGNAGN$_{11}$GANGANGG (SEQ ID NO:6). In another embodiment, the promoter DNA motif has at least 75% identity to the specifically identified nucleotides of the consensus sequence, i.e., the specified A and G. In some embodiments, the inducible promoter is inducible by a D-amino acid. In other embodiments, the D-amino acid is D-alanine, D-threonine, D-serine, D-valine or D-proline.

In another aspect, the present invention provides a nucleic acid construct. In one embodiment, the nucleic acid construct comprises an inducible promoter, as described herein, operably linked to a heterologous polynucleotide. In another embodiment, the polynucleotide is operably linked to a transcription terminator. In a further embodiment, the transcription terminator is operable in a fungal species. In some embodiments, the nucleic acid construct contains a CT-rich nucleotide sequence. In one embodiment, the CT-rich nucleotide sequence has at least 75% identity to the consensus sequence T(T/C)TCCC(T/C)CTCC(T/C)CCCCA C(A/T)(C/T)CCGA (SEQ ID NO:7).

In some embodiments, the CT-rich nucleotide sequence is an intron. In one embodiment, the intron is inserted, positioned or located upstream of or within the 5' end or 5' region of the polynucleotide in the nucleic acid construct. In another embodiment, the intron is inserted into the 5' UTR of the inducible promoter. In other embodiments, the intron includes a DNA motif, sometimes referred to herein as the intron DNA motif. In one embodiment, the intron DNA motif comprises the CT-rich nucleotide sequence. In other embodiments, the CT-rich nucleotide sequence is contained within the coding sequence of a heterologous polynucleotide in the nucleic acid construct. In some embodiments, the CT-rich nucleotide sequence may span an intron and the nucleotides of the promoter and/or heterologous polynucleotide surrounding the intron. In some embodiments, the heterologous polynucleotide encodes a protein of interest. In other embodiments, the heterologous polynucleotide encodes an RNA molecule for down regulating a target gene of interest.

In a further aspect, the present invention provides a fungal cell comprising the nucleic acid construct described herein. In one embodiment, the fungal cell is a cell of a species of the *Rhodosporidium* genus. In another embodiment, the fungal cell is a cell of a species of the *Rhodotorula* genus. In some embodiments, the nucleic acid construct is stably integrated in the genome of the fungal cell. In other embodiments, the fungal cell is part of a composition also comprising a culture medium.

In an additional aspect, the present invention provides a method of preparing and using a fungal species comprising the nucleic acid construct described herein. In one embodiment, a method of preparing the fungal species comprises introducing the nucleic acid construct described herein into a fungal cell and selecting a fungal cell that has the nucleic acid stably integrated in its genome. In another embodiment, a method of using the fungal species comprises culturing the fungal species comprising the nucleic acid construct described herein in a medium containing a D-amino acid. In some embodiments, the D-amino acid is D-alanine, D-threonine, D-serine, D-valine or D-proline.

BRIEF DESCRIPTION OF THE FIGURES

FIGS. 2A-2D show binary vectors and DAO1 promoter structure used in certain embodiments of the present invention. FIG. 2A: T-DNA region of the GFP reporter plasmid pKC1, luciferase reporter plasmid pKCL2, and the knock-in strategy of reporter gene cassette to the CAR2 allele of *R. toruloides*. FIG. 2B: T-DNA region of plasmid series pKCLDx with the luciferase reporter gene RtLUC-2. FIG. 2C: Partial DAO1 promoter sequence including the first intron (SEQ ID NO:8). The location of mRNA transcription start position (tsp), 5' untranslated region (5'UTR), CT-rich region (ct box), intron 1 and N-terminal peptide sequence (SEQ ID NO:87) are shown. The complete peptide sequence of the Dao1 protein is set forth in SEQ ID NO:88. FIG. 2D: Candidate albino transformants visually selected on selection media.

FIG. 3A: Schematic diagrams obtained for DAO1 genes (SEQ ID NOs:9, 11, 13, 15, 17, 19, 21, 23, 25, 27 and 29). FIG. 3B: Phylogenetic tree analysis obtained for Dao1 proteins (SEQ ID NOs:10, 12, 14, 16, 18, 20, 22, 24, 26, 28 and 30).

FIG. 4A: Southern blot analysis of DAO1 gene copies in *R. toruloides*. The digoxigenin-labeled DNA probe was amplified using the template of genomic DNA and oligos DAO1f and DAO1r (Table 1), and was shown in FIG. 2A. FIG. 4B: mRNA levels of DAO1 at 3 and 6 hour after induction with 70 mM D or L-alanine. Carbon and nitrogen sources used: CTL—glucose and ammonium sulfate; L-ala—glucose and L-alanine; D-ala—glucose and D-alanine; solo D-ala—D-alanine only. FIG. 4C: mRNA levels of DAO1 in *R. toruloides* cells cultured in YPD medium under various stress conditions for 6 hour. CTL—cultured in YPD broth at 28° C.; Oxidative stress—cultured in YPD broth supplemented with 1% $H_2O_2$ (w/v) at 28° C.; Cold stress—cultured in YPD broth at 4° C.; Heat stress—cultured in YPD broth at 37° C.; Osmatic stress—Cultured in YPD broth supplemented with 1 M KCl at 28° C.; Glycerol—cultured in YPG broth (carbon source of glucose in YPD replaced by the same concentration of glycerol) at 28° C.

FIGS. 5A-5C show the analysis of 1.0 kb upstream sequences of DAO1 from Pucciniomycotina species. FIG. 5A: Localization of three highly conserved motifs in the upstream sequences of DAO1s. Sequences examined: Rt1—*R. toruloides* ATCC 10657 (SEQ ID NO:31); Rt3—*R. toruloides* MTCC 457 (SEQ ID NO:32); Rt4—*R. toruloides* NP11 (SEQ ID NO:33); Rg2—*R. glutinis* ATCC 204091 (SEQ ID NO:34); Rg3—*R. graminis* WP1 (SEQ ID NO:35); Sr—*S. roseus* (SEQ ID NO:36); Pt—*P. tritartic* (SEQ ID NO:37); Pg-*P. graminis* (SEQ ID NO:38); Rm—*R. minuta* (SEQ ID NO:39); S1—*S. linerdae* (SEQ ID NO:40); Um—*U. maydis* (SEQ ID NO:41); Sr2—*S. reilianum* (SEQ ID NO:42); M1—*Melampsora laricispopulina* (SEQ ID NO:43) was used for multiple sequence alignment but does not have the consensus motifs as shown. FIG. 5B: Nucleotide sequence logos of the motifs examined (motif 1: SEQ ID NO:91; motif 2: SEQ ID NO:92; motif 3: SEQ ID NO:93). FIG. 5C: Alignment of motif 1 sequences among the upstream sequences of DAO1. The sequences are set forth as follows: Rg3—SEQ ID NO:44; Um—SEQ ID NO:45; Sr2—SEQ ID NO:46; Sr—SEQ ID NO:47; Rg2—SEQ ID NO:48; Rt1—SEQ ID NO:49; S1—SEQ ID NO:50; Consensus—SEQ ID NO:6

FIG. 6A: Schematic diagram of serial deletions of the DAO1 promoter. All promoters were cloned in pKCLDx (FIG. 2B), where x indicates different versions of the DAO1 upstream sequence. $P_{DAO1}$: 2021 bp DAO1 upstream sequence without intron 1; $P_{DAO1in}$: 2175 bp DAO1 upstream sequence including intron 1 (SEQ ID NO:1 without NcoI site); $P_{DAO1in\bar{i}}$: same as $P_{DAO1in}$ except that motif 1 is deleted. $P_{DAO1in2}$ to $P_{DAO1in6}$ are serial deletions from the 5', with a length of 1655, 1157, 953, 663 and 354 bp, respectively. A codon adapted luciferase gene (RtLUC-2, SEQ ID NO:51) was used as the reporter for the promoter activity. FIG. 6B: Effect of intron 1 and motif 1 on DAO1 promoter activity. Cells were cultured for 21 hr in MinABs medium supplemented of D-alanine or L-alanine. FIG. 6C: Effects of 5' sequence deletions on $P_{DAO1in}$ activity. RPA: relative promoter activity; GPD1: endogenous 795-bp promoter of glyceraldehyde-3-phosphate dehydrogenase; P-less: negative control construct where the RtLUC-2:T35S is not fused to any promoter; D-ala and L-ala: cells were cultured in medium with D- and L-alanine, respectively.

FIGS. 7A-7D show the effects of extra carbon or nitrogen sources on DAO1 promoter activities. FIG. 7A: Effects of different media. Basal medium MinAB was supplemented with the designated carbon or nitrogen source and the protein extract was made from 21-hr cultures. Abbreviations: G—Glucose (10 g/L); AS—Ammonium sulfate (70 mM); D—D-alanine (70 mM); L—L-alanine (70 mM). FIG. 7B: Effects of D-alanine concentrations. 10 g/L glucose and different concentrations of D-alanine were supplemented to the basal medium MinABs. FIG. 7C: Effects of glucose concentrations. 70 mM D-alanine and different concentrations of D-alanine were supplemented to the basal medium MinABs. FIG. 7D: Effects of ammonium sulfate concentrations. 10 g/L glucose, 70 mM D-alanine and different concentrations of ammonium sulfate were supplemented to the basal medium MinABs. All experiments were performed by biological triplicates and RPA represents the relative reading of luciferase activity.

FIGS. 9A-9C show the analysis of the first intron sequences of DAO1 from Rhodosporidium/Rhodotorula species. FIG. 9A: Alignment of intron 1 5' partial sequences. Sequences used are: Rg2—R. glutinis ATCC 204091 (SEQ ID NO:52); R. toruloides MTCC 457 (SEQ ID NO:53); R. toruloides NP11 (SEQ ID NO:54); R. graminis WP1 (SEQ ID NO:55). The complete intron sequences are set forth in SEQ ID NOs:56-59, respectively. FIG. 9B: Nucleotide sequence logos of motif 2. FIG. 9C: Promoter activities PDAO1in mutants. DAO1$_{in}$: 0.7 kb version of the intron 1-containing promoter; DAO1$_{in2}$: as DAO1$_{in}$ except the translation initiation codon was changed to ATC so that no additional N-terminal residues are translated in the protein to be expressed; DAO1$_{in3}$: as DAO1$_{in2}$ except the all cytosine residues in motif 2 were changed to adenine; DAO1$_{in4}$ DAO1$_{in2}$ except the 24 nt motif 2 was deleted.

FIG. 10A: Southern blot analysis of DAO1 deletion mutants. Genomic DNA (2 µg) was digested with PstI and hybridized against the digoxigenin-labeled probe of DAO1R (probe 2 in FIG. 2A). FIG. 10B: Growth of DAO1 null mutant in YNB medium supplemented with D-alanine or L-alanine as the sole carbon source. FIG. 10C: Comparison of DAO1in promoter activity in various media in Wt and DAO1 knockout mutant Δdao1. WT and Δdao1 cells knockin with the 2.2 kb DAO1 promoter ($P_{DAO1in}$) LUC2 reporter at the CAR2 locus were cultured in MinABs supplemented with (shown with +) various combination of glucose (10 g/L), ammonium sulfate (70 mM), D-alanine (D-ala) and L-alanine (70 mM). Induction with lower concentration of D-alanine (10 mM and 1 mM) is shown on the right side of FIG. 10C.

DETAILED DESCRIPTION OF THE INVENTION

Figure 1:
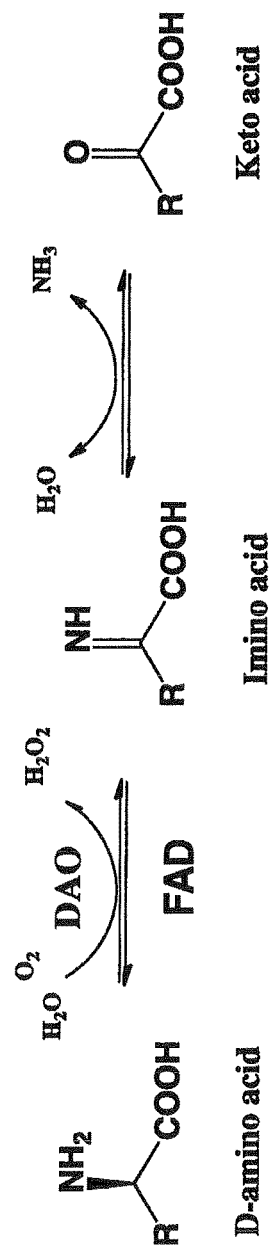
FIG. 1 is a scheme illustrating the reaction catalyzed by D-amino acid oxidase. The reductive reaction requires FAD cofactor, which is re-oxidated by molecular oxygen to give hydrogen peroxide. The imino acid is hydrolyzed spontaneously to the corresponding keto acid and ammonia.

The present invention relates to the field of fungal biotechnology, more particularly to a strong inducible gene expression system in fungal species, such as Rhodosporidium or Rhodotorula genus.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

"Altered levels" refers to the production of gene product(s) in transgenic organisms in amounts or proportions that differ from that of normal, control or non-transformed organisms.

"Coding sequence" refers to a nucleotide sequence that codes for a specific amino acid sequence.

A "control" or "control fungus" or "control fungal cell" provides a reference point for measuring changes in phenotype of a subject fungus or fungal cell in which genetic alteration, such as transformation, has been effected as to a polynucleotide of interest. A subject fungus or fungal cell may be descended from a fungus or fungal cell so altered and will comprise the alteration.

A control fungus or fungal cell may comprise, for example: (a) a wild-type fungus or fungal cell, i.e., of the same genotype as the starting material for the genetic alteration which resulted in the subject fungus or fungal cell; (b) a fungus or fungal cell of the same genotype as the starting material but which has been transformed with a null construct (i.e., with a construct which has no known effect on the trait of interest, such as a construct comprising a marker gene); (c) a fungus or fungal cell which is a non-transformed segregant among progeny of a subject fungus or fungal cell; (d) a fungus or fungal cell genetically identical to the subject fungus or fungal cell but which is not exposed to conditions or stimuli that would induce expression of the polynucleotide of interest or (e) the subject fungus or fungal cell itself, under conditions in which the polynucleotide of interest is not expressed.

"D-Amino acid oxidase" (DAAO, EC 1.4.3.3), "Dao1," "Dao1 polypeptide" and "Dao1 protein" are used interchangeably herein to refer to a flavoenzyme that specifically catalyzes the oxidative deamination of D-amino acids to α-keto acids, ammonia and hydrogen peroxide.

"DAO1" and "DAO1 gene" are used interchangeably herein to refer to a nucleic acid sequence which encodes a Dao1 polypeptide.

"DAO1 promoter" refers to a portion of the DAO1 gene upstream of the translation start site which controls transcription of the Dao1 polypeptide or any nucleic acid operatively linked to the DAO1 promoter. In some embodiments, the DAO1 promoter includes the consensus sequence AGGNNGNAGN$_{11}$GANGANGG (SEQ ID NO:6) where N is any deoxyribonucleotide. In other embodiments, the DAO1 promoter may include nucleotides downstream of the translation start site.

A "dsRNA" or "RNAi molecule," as used herein in the context of RNAi, refers to a compound, which is capable of down-regulating or reducing the expression of a gene or the activity of the product of such gene to an extent sufficient to achieve a desired biological or physiological effect. The term "dsRNA" or "RNAi molecule," as used herein, refers to one or more of a dsRNA, siRNA, shRNA, ihpRNA, synthetic shRNA, miRNA.

The term "down regulated" or "down regulation," as it refers to genes inhibited by the subject RNAi method, refers to a diminishment in the level of expression of a gene(s) in the presence of one or more RNAi construct(s) when compared to the level in the absence of such RNAi construct(s). The term "down regulated" is used herein to indicate that the target gene expression is lowered by 1-100%. For example, the expression may be reduced by about 5%, 10%, 15%, 20%, 25%, 30%, 35%, 40%, 45%, 50%, 55%, 60%, 65%, 70%, 75%, 80%, 85%, 90%, 95%, or 99%.

"Expression" refers to the production of a functional product. For example, expression of a nucleic acid fragment may refer to transcription of the nucleic acid fragment (e.g., transcription resulting in mRNA, functional RNA, dsRNA and the like) and/or translation of mRNA into a precursor or mature protein.

As used herein, "gene" refers to a nucleic acid sequence that encompasses a 5' promoter region associated with the expression of the gene product, any intron and exon regions and 3' or 5' untranslated regions associated with the expression of the gene product.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. Gene silencing may be allele-specific wherein specific silencing of one allele of a gene occurs.

"Heterologous" with respect to sequence means a sequence that originates from a foreign species, or, if from the same species, is substantially modified from its native form in composition and/or genomic locus by deliberate human intervention.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Intron" as used herein refers to an intron that is inserted, positioned or located upstream of or within the 5' end of a polynucleotide in a nucleic acid construct as described herein. The intron may be isolated from a gene, such as a fungal gene or it may be synthesized on the basis of known introns.

The term "operably linked" or "operatively linked" is defined herein as a configuration in which a regulatory or control sequence is appropriately placed at a position relative to the polynucleotide sequence of the nucleic acid construct such that the control sequence directs the expression of a polynucleotide of the present invention. Regulatory or control sequences may be positioned on the 5' side of the nucleotide sequence or on the 3' side of the nucleotide sequence as is well known in the art.

"Over-expression" or "overexpression" refers to the production of a gene product in transgenic organisms that exceeds levels of production in normal, control or non-transformed organisms.

The terms "polynucleotide," nucleic acid" and "nucleic acid molecule are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range. The "nucleic acid" may also optionally contain non-naturally occurring or altered nucleotide bases that permit correct read through by a polymerase and do not reduce expression of the nucleic acid.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

"Progeny" comprises any subsequent generation of a fungus.

"Promoter" refers to a nucleic acid fragment capable of controlling transcription of another nucleic acid fragment.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct", "recombinant construct" and "nucleic acid construct" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

The term "strong expression" as used herein means expression of a marker protein, mRNA, siRNA (small-interference RNA) or miRNA (microRNA) to a detectable level using detection methods known, for example, florescence for GFP and luciferase, activity assay for GUS and lacZ, Northern blots or Western blots.

"Transient transformation" refers to the introduction of a nucleic acid fragment into the nucleus, or DNA-containing organelle, of a host organism resulting in gene expression without genetically stable inheritance.

"Transgenic fungus" includes reference to a fungus which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window such as the full length of a referenced SEQ ID NO:, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

As used herein, the term "substantially homologous" or "substantial homology", with reference to a nucleic acid sequence, includes a nucleotide sequence that hybridizes under stringent conditions to a referenced SEQ ID NO:, or a portion or complement thereof, are those that allow an antiparallel alignment to take place between the two sequences, and the two sequences are then able, under stringent conditions, to form hydrogen bonds with corresponding bases on the opposite strand to form a duplex molecule that is sufficiently stable under conditions of appropriate stringency, including high stringency, to be detectable using methods well known in the art. Substantially homologous sequences may have from about 70% to about 80% sequence identity, or more preferably from about 80% to about 85% sequence identity, or most preferable from about 90% to about 95% sequence identity, to about 99% sequence identity, to the referent nucleotide sequences as set forth the sequence listing, or the complements thereof. Alternatively, substantially homologous sequences include those which hybridize under stringent conditions to the target regions of introns of plant genes. For stringency conditions, see the description herein and see also U.S. Pat. Nos. 8,455,716 and 8,536,403.

Embodiments of the present invention which include isolated promoters, nucleic acid constructs, compositions (such as fungi) comprising these nucleic acid constructs, and methods utilizing these nucleic acid constructs are now described.

Isolated Promoters

The present invention provides isolated, inducible promoters for expression of a heterologous polynucleotide in a fungal species:

In one embodiment, the inducible promoter comprises a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to SEQ ID NO:94.

In another embodiment, the inducible promoter comprises a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to SEQ ID NO:95.

In a further embodiment, the inducible promoter comprises a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to SEQ ID NO:96.

In another embodiment, the inducible promoter comprises a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to SEQ ID NO:97.

In another embodiment, the inducible promoter comprises a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V or Clustal W method of alignment, when compared to SEQ ID NO:5.

In a further embodiment, the inducible promoter comprises a nucleotide sequence, wherein the nucleotide sequence is hybridizable under stringent conditions with a DNA molecule comprising the full complement of SEQ ID NO:94, 95, 96, 97 or 5.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., *Molecular Cloning: A Laboratory Manual*, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

In another embodiment, the inducible promoter comprises a nucleotide sequence, wherein the nucleotide sequence is derived from SEQ ID NO:94, 95, 96, 97 or 5 by alteration of one or more nucleotides by at least one method selected from the group consisting of: deletion, substitution, addition and insertion.

In some embodiments, each of the above inducible promoters includes a DNA motif, sometimes referred to herein as the promoter DNA motif. In one embodiment, the promoter DNA motif comprises the consensus sequence AGGNNGNAGN$_{11}$GANGANGG (SEQ ID NO:6). In another embodiment, the promoter DNA motif has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the specifically identified nucleotides of the consensus sequence, i.e., the specified A and G nucleotides. In some embodiments, the inducible promoter is inducible by a D-amino acid. In other embodiments, the D-amino acid is D-alanine, D-threonine, D-serine, D-valine or D-proline.

Database searches and homology searches of genome and nucleotide databases can be used to identify similar inducible promoters based on the alignment of nucleotides using algorithms or computer programs and these techniques well known to those of skill in the art.

Nucleic Acid Constructs:

In one aspect, the present invention provides nucleic constructs.

In one embodiment, the nucleic acid construct comprises an inducible promoter, as described herein, operably linked to a heterologous polynucleotide. In another embodiment, the polynucleotide is operably linked to a transcription terminator. In a further embodiment, the transcription terminator is operable in a fungal species. Transcription terminators of protein encoding genes are typically located downstream (3') of the gene, after the stop codon (TGA, TAG or TAA). Transcription terminators play an important role in the processing and stability of RNA as well as in translation. Most, but not all transcription terminators, contain a polyadenylation sequence or cleavage site.

In some embodiments, the nucleic acid construct contains a CT-rich nucleotide sequence. In one embodiment, the CT-rich nucleotide sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the consensus sequence T(T/C)TCCC(T/C)CTCC(T/C)CCCCAC(A/T)(C/T)CCGA (SEQ ID NO:7).

In some embodiments, the CT-rich nucleotide sequence is an intron. The intron may be isolated or derived from a gene, such as a fungal gene, or it may be synthesized on the basis of known introns. In some embodiments, the intron is intron 1 of a DAO1 gene. In one embodiment, the DAO1 gene is a fungal DAO1 gene. In some embodiments, the intron includes a DNA motif, sometimes referred to herein as the intron DNA motif. In one embodiment, the intron DNA motif has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the consensus sequence T(T/C)TCCC(T/C)CTCC(T/C)CCCCAC(A/T)(C/T)CCGA (SEQ ID NO:7).

In one embodiment, the intron is inserted, positioned or located upstream of or within the 5' end of a polynucleotide in the nucleic acid construct. In some embodiments, the intron is operably linked to the inducible promoter on its 5' end and operably linked to the heterologous polynucleotide on its 3' end. In another embodiment, the intron is positioned within the 5' end or 5' region of the heterologous polynucleotide. In a further embodiment, the intron is inserted into the 5' UTR of the inducible promoter.

In some embodiments, the CT-rich nucleotide sequence may span an intron and the nucleotides of the inducible promoter and/or heterologous polynucleotide surrounding the intron.

In other embodiments, the CT-rich nucleotide sequence is contained within the coding sequence of a polynucleotide in the nucleic acid construct. In one embodiment, the CT-rich nucleotide sequence contained within coding sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the consensus sequence T(T/C)TCCC(T/C)CTCC(T/C)CCCCAC(A/T)(C/T)CCGA (SEQ ID NO:7).

In some embodiments, the heterologous polynucleotide encodes a protein of interest. Examples of proteins of interest include, but are not limited to, antibiotic resistance enzyme, herbicide resistance enzyme, GFP, GUS, lacZ, terpene synthase, fatty acid desaturase, P450 cytochrome oxidase, glucanase, xylanase, mannanase, mannosidase, glucosidase, glucomannanase, xyluglucanase, hydroxymethylglutaryl-CoA synthase, hydroxymethylglutaryl-CoA reductase, acetyl-CoA C-acetyltransferase, mevalonate kinase, phosphomevalonate kinase, diphosphomevalonate decarboxylase, isopentenyl-diphosphate delta-isomerase, farnesyl diphosphate synthase, geranylgeranyl diphosphate synthase, methyl transferase, or glucosyl transferease, beta-carotenoid hydroxylase and beta-carotenoid oxidase.

In other embodiments, the heterologous polynucleotide encodes an RNA molecule for down regulating a target gene of interest. Down-regulation of a target gene can be brought about by using well known techniques, including, but not limited to, RNAi techniques, such as dsRNA, miRNA, siRNA, smRNA, hpRNA or ihpRNA (collectively referred to as RNAi molecules), sense suppression (co-suppression), antisense, and the like. Such techniques are described in U.S. Pat. No. 7,312,323 and references cited therein. For example, reduction might be accomplished, for example, with transformation of a fungal host cell to comprise a promoter and other 5' and/or 3' regulatory regions described herein linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. RNAi molecules or microRNA molecules (referred to collectively herein as RNAi molecules) can be prepared by the skilled artisan using techniques well known in the art, including techniques for the selection and testing of RNAi molecules and microRNA molecules that are useful for down regulating a polynucleotide of the present invention. See, for example, Wesley et al. (2001), Mysara et al. (2011) and Yan et al. (2012).

For example, a nucleic acid construct can be prepared that includes a polynucleotide that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence, or a fragment thereof, of a target gene, and that is from about 10 nucleotides to about 1,800 nucleotides in length. The length of the sequence that is similar or identical to the sense coding sequence can be from 10 nucleotides to 1000 nucleotides, from 15 nucleotides to 600 nucleotides, from 20 nucleotides to 500 nucleotides, or from 25 nucleotides to 100 nucleotides, or any length within the 10 nucleotides to 2,500 nucleotides. The other strand of the stem portion of a double stranded RNA comprises a sequence that is similar or identical to the antisense strand, or a fragment thereof, of the coding sequence of the target gene, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of the mRNA of the target gene, and the other strand of the stem portion of the double stranded RNA comprises a sequence that is similar or identical to the sequence that is complementary to the 3' or 5' untranslated region, respectively, or a fragment thereof, of the mRNA of the target gene. In other embodiments, one strand of the stem portion of a double stranded RNA comprises a sequence that is similar or identical to the sequence of an intron or a fragment thereof in the pre-mRNA transcribed from the target gene, and the other strand of the stem portion comprises a sequence that is similar or identical to the sequence that is complementary to the sequence of the intron or fragment thereof in the pre-mRNA.

The loop portion of a double stranded RNA can be from 3 nucleotides to 5,000 nucleotides, e.g., from 3 nucleotides to 2500 nucleotides, from 15 nucleotides to 1,000 nucleotides, from 20 nucleotides to 500 nucleotides, or from 25 nucleotides to 200 nucleotides, or any length within the 3 nucleotides to 5,000 nucleotides. The loop portion of the RNA can include an intron or a fragment thereof. A double stranded RNA can have zero, one, two, three, four, five, six, seven, eight, nine, ten, or more stem-loop structures.

The nucleic acid construct may include other transcriptional regulatory regions as are well known in the art.

In some embodiments, the nucleic acid construct further comprises a selectable marker. Selectable markers are well known to the skilled artisan as are nucleic acid constructs incorporating such selectable markers and promoters to drive their expression, such as described in International Patent Application Publication No. WO 2012/169969. Any suitable promoter operably linked to any suitable selectable marker can be used in the present invention. In some embodiments, examples of suitable promoters for use with selectable markers include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidyl-prolyl isomerase (PPI), acetyl-CoA carboxylase (ACC) or transaldolase.

In one embodiment, the coding sequence for the selectable marker is one that is either naturally existent or artificially created and contains at least about 60% GC. In a second embodiment, the coding sequence for the selectable marker is one that is either naturally existent or artificially created and contains about 70% GC. In a third embodiment, the coding sequence for the selectable marker is one that is either naturally existent or artificially created and contains about 75% GC. In one embodiment, at least about 70% of the codon triplets of such coding sequences end with C or G. In another embodiment, more than about 80% of the codon triplets of such coding sequences end with C or G. In one embodiment, the coding sequence for a selectable marker is at least 60% GC, preferably about 70% GC and most preferably about 75% GC in which at least 70% of the codon triplets end with C or G, preferably more than 80% of the codon triplets end with C or G. In one embodiment, such coding sequences are composed of UCG codons in at least about 40% of the total serine (Ser) residues.

In some embodiments, the selectable marker is part of a recombination marker free system. In one embodiment, the recombination marker free system is a Cre-lox recombination marker free system, such as described by Zuo et al. (2001). Such a system is useful for producing selection marker free transgenic plants, including transgenic Jatropha plants. In some embodiments, the recombination marker free system is positioned between the plant operable promoter and the one or more nucleic acid fragments. In this embodiment, the removal of the marker gene by the recombination event places the plant operable promoter in operable linkage with the one or more nucleic acid fragments as described herein.

In preparing the nucleic acid construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

In a further aspect, the present invention provides a fungal cell comprising the nucleic acid construct described herein. In one embodiment, the fungal cell is a cell of a species of the *Rhodosporidium* genus. In another embodiment, the fungal cell is a cell of a species of the *Rhodotorula* genus. In some embodiments, the nucleic acid construct is stably integrated in the genome of the fungal cell. In other embodiments, the fungal cell is part of a composition also comprising a culture medium.

One or more nucleic acid constructs may be introduced directly into a fungal cell using techniques such as electroporation, DNA particle bombardment. Alternatively, the nucleic acid constructs may be combined with suitable T-DNA flanking regions and introduced into an *Agrobacterium tumefaciens* host, which will deliver the gene cassette into the fungal genome. Thus, any method, which provides for effective transformation/transfection of fungi may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

It may be useful to generate a number of individual transformed fungi with any recombinant construct in order to recover fungi free from any positional effects. It may also be preferable to select fungi that contain more than one copy of the introduced nucleic construct such that high levels of expression of the polynucleotide are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

In an additional aspect, the present invention provides a method of preparing and using a fungal species comprising the nucleic acid construct described herein. In one embodiment, a method of preparing the fungal species comprises introducing the nucleic acid construct described herein into a fungal cell and selecting a fungal cell that has the nucleic acid construct stably integrated in its genome. In another embodiment, a method of using the fungal species comprises culturing the fungal species comprising the nucleic acid construct described herein in a medium containing a D-amino acid. In some embodiments, the D-amino acid is D-alanine, D-threonine, D-serine, D-valine or D-proline.

In some embodiments, transformed fungi are transferred to standard growing media (e.g., solid or liquid nutrient media, grain, vermiculite, compost, peat, wood, wood sawdust, straw, etc.) and grown or cultivated in a manner known to the skilled artisan. In one embodiment, the media is minAB medium or minAB medium modified to omit carbon source and $NH_4NO_3$. In other embodiments, the expression of the polynucleotide of the nucleic acid construct is induced by the presence of a D-amino acid in the growing media. In one embodiment, the D-amino acid is added to the culture media prior to culturing the transformed fungi. In another embodiment, the D-amino acid is added to the culture media after the transformed fungi have been added to the culture media. In some embodiments, the amount of D-amino acid in the culture media is from about 0.1 mM to about 100 mM, preferably from about 1.0 mM to about 70 mM, more preferably from about 1.0 mM to about 20 mM.

In one embodiment, traditional fungi media are used for culturing the transformed fungi in which the media has been modified to contain no or a low amount of a carbon source other than the D-amino acid. In another embodiment, traditional fungi media are used for culturing the transformed fungi in which the media has been modified to contain no or a low amount of a nitrogen source other than the D-amino acid. In some embodiments the cell culturing is preferably performed at 25° C. to 35° C.

In one embodiment, the DAO1 inducible constructs are introduced into a yeast strain with reduced or no (zero) D-amino acid oxidase activity.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Strains, Media, and Culture Conditions

*R. toruloides* strain ATCC 10657 was obtained from ATCC (USA). *Rhodotorula graminis* WP1 was obtained from Fungal Genetics Stock Center (University of Missouri, USA). *R. toruloides* was cultured at 28° C. in YPD broth (1% yeast extract, 2% peptone, 2% glucose, w/v) or on potato-dextrose agar (PDA). *A. tumefaciens* strain AGL1 (26) or AGL2 (27) was used for donor of T-DNA and was cultured at 28° C. in either liquid or solid 2YT medium (1.6% tryptone, 1% yeast extract, 0.5% NaCl). *Escherichia coli* XL1-Blue was cultured in Luria-Bertani (LB) broth or on LB agar and used for routine DNA manipulations.

For gene induction studies, modified MinAB (MinABs) (28) with carbon source and nitrogen source ($NH_4NO_3$) omitted was used as basal medium. Carbon source (10 g/L glucose, 70 mM L-alanine or D-alanine) and nitrogen source (70 mM ammonium sulfate, L-alanine or D-alanine) were supplemented as required. For stress treatments, YPD broth was used as the basal medium and cultured after supplementation of various chemicals, or in harsh conditions. Unless indicated otherwise, cell cultures were conducted in a rotary shaker under 28° C. and 250 rpm.

Example 2

Plasmid Constructs

Oligonucleotides that were used are listed in Table 1. All restriction and modification enzymes were obtained from New England Biolabs (NEB, Massachusetts, USA).

TABLE 1

Oligonucleotide Sequences

| Name | Sequence (Restriction enzyme site)* (SEQ ID NO:) | PCR target |
|---|---|---|
| Rt290Sf | 5'-TTTactagtCTTCCCGGTCTCGTATCGAG-3' (SpeI) (60) | $P_{DAO1}$ 2.0 kb |
| Rt315S | 5'-TTTACTAGTACTCCGCAATCTGCAGAGAC-3' (SpeI) (61) | $P_{DAO1}$ 1.5 kb |
| Rt314S | 5'-TTTactagtCATGGTCTGATCGCTTGTGTG-3' (SpeI) (62) | $P_{DAO1}$ 1.0 kb |
| Rt120S | 5'-TTTactagtGTGGCAGGTGTGCGTG-3' (SpeI) (63) | $P_{DAO1}$ 0.8 kb |
| Rt313S | 5'-TTTactagtCGTTCGTGGGCTCAAGGAAG-3' (SpeI) (64) | $P_{DAO1}$ 0.5 kb |
| Rt117S | 5'-TTTactagtCGACGACGGGAAGCTTCG-3' (SpeI) (65) | $P_{DAO1}$ 0.2 kb |
| Rt287Nr | 5'-TTTccatggCAATCACTGTATAATCAAGAGCTG-3' (NcoI) (66) | $P_{DAO1in}$ reverse |
| Rt309Nr | 5'-TTTccatggCGTCGTTCGAGCAG-3' (SpeI) (67) | $P_{DAO1}$ reverse |
| Rt311 | 5'-GAAGCTTCGGCACGAGCATG-3' (68) | $P_{DAO1int}$ without |
| Rt312 | 5'-ACAGTCATGCTCGTGCCGAAGCTTCGCAACCGCTCATCAGTACAC-3' (69) | $P_{DAO1int}$ without motif#1 |
| SFGEPSEQ | 5'-GGACAAACCACAACTAGAATGCAG-3' (70) | $P_{DAO1int}$ without motif#1 |
| 35STer | 5'-AAAGCATGCTAATTCGGGGGATCTGGAT-3' (71) | $P_{DAO1int}$ without motif#1 |
| Rt327r | 5'-GGCGTCGTTCGAGCAGTAC-3' (72) | $P_{DAO1int2}$ |
| Rt328f | 5'-CTGCTTGTACTGCTCGAACGACGCCATCCATTCACAGAAGCGCGTCGT-3' (73) | $P_{DAO1int2}$ |
| Rt329r | 5'-GACGCACCGCCTGATCCGAG-3' (74) | $P_{DAO1int3}$ and $P_{AO1int4}$ |
| Rt330f | 5'-TTGTCCTCGGATCAGGCGGTGCGTCYTTAAATATAATAAAAAAAAAAGACAGTTCTCGAGGAGGAGTAC-3' (75) | $P_{AO1int3}$ |
| Rt331f | 5'-TTGTCCTCGGATCAGGCGGTGCGTCCAGTTCTCGAGGAGGAGTAC-3' (76) | $P_{AO1int4}$ |
| LUC2U | 5'-GAAGTACTCGGCGTAGGTG-3' (77) | $P_{AO1int2,3,4}$ |
| DAO1f | 5'-CTTCGTGCTAACCAAGCTCGT-3' (78) | Probe of DAO1 |
| DAO1r | 5'-GTCTCAGGGTTGACGGACAAG-3' (79) | Probe of DAO1 |
| qDAO1f | 5'-TCAAACCGTCCTCGTCAAGTC-3' (80) | qPCR of DAO1 |
| qDAO1r | 5'-GTTGACGGACAAGTCCCAATC-3' (81) | qPCR of DAO1 |
| qACT1f | 5'-CGACAACTTTGACGACCCTTC-3' (82) | qPCR of ACT1, reference gene |
| qACT1r | 5'-CAGGTTGGGACAAGTTGGGTA-3' (83) | qPCR of ACT1, reference gene |
| HptRU | 5'-GGACAAACCACAACTAGAATGCAG-3' (84) | hygromycin resistance gene |
| HptRSL2 | 5'-AAAGCATGCTAATTCGGGGGATCTGGAT-3' (85) | hygromycin resistance gene |

*Sequences in lowercase and italics denote the recognition (marked in brackets).

Plasmid pKC1 is a pPZP200 derivative (29) consisting of a hygromycin resistant cassette ($P_{GPD1-3}$::hpt-3::Tsv40) and a GFP reporter cassette ($P_{GPD1}$::RtGFP::35T), wherein $P_{GPD1-3}$ and $P_{GPD1}$ is the glyceraldehyde 3-phosphate dehydrogenase promoter of *Rhodotorula graminis* WP1 and *R. toruloides* ATCC 10657, respectively (GenBank Accession Nos. JQ806386 and JN208861, respectively) (30); hpt-3 (GenBank Accession No. JQ806387) and RtGFP (GenBank Accession No. JQ806388) is the codon-optimized gene encoding hygromycin phosphotransferase (Hpt) and eGFP, respectively (30); $Tsv_{40}$ and $T_{35S}$ is the terminator of Simian virus 40 and Cauliflower mosaic virus 35S gene, respectively (FIG. 2A).

Plasmid pKCL2 was derived from pKC1 where the RtGFP reporter gene was replaced by a synthetic codon-optimized luciferase reporter gene RtLUC-2 that encodes the *Photinus pyralis* luciferase (GenBank Accession No. ACH53166). The 2.0 kb SpeI-NcoI DNA fragment derived from the upstream regions of DAO1 coding sequence were obtained by PCR amplification using the template of *R. toruloides* genomic DNA and oligos Rt290Sf and Rt309Nr (Table 1). The PCR products was double digested with SpeI-NcoI and ligated with SpeI-NcoI-linearized pKCL2 vector to create plasmid pKCLD1 (FIG. 2B).

The intron-containing promoter of DAO1 ($P_{DAO1in}$, 2.2 kb) was amplified using the same template and oligos Rt290Sf and Rt287Nr. $P_{DAO1in}$ contains the first 40 nt Dao1-encoding sequence of exon 1, 108 nt intron 1 and first 6 nt of exon 2, giving rise to a 16 aa (MHSQKRVVVLGS-GVIA; SEQ ID NO:86) extra residues to any protein expressed by the promoter. the last amino acid was changed from $17^{th}$) residue (G17) was changed to alanine because of the introduction of a NcoI site for cloning of genes of interest (FIG. 2C). The SpeI-NcoI treated PCR products of $P_{DAO1in}$ were ligated with similarly digested pKCL2 vector to create plasmid pKCLD2.

To make the motif 1-deleted mutant promoter ($P_{DAO1int}$, 2.2 kb, FIGS. 5A and 6A), a fusion PCR of the upstream and downstream DNA sequences adjacent to the DAO1 consensus motif 1 was performed. The upstream sequence was amplified using pKCLD2 as the template and oligo pair SFGFPSEQ/Rt312 while downstream DNA sequence used Rt311/35STer as the primers. Subsequently, the two PCR fragments were fused by PCR using oligos Rt290Sf and Rt287Nr as described previously (31). The resultant 2.2 kb PCR products were digested with SpeI-NcoI and ligated with the similarly digested pKCL2 vector to create plasmid pKCLD3.

A promoter-less RtLUC-2 negative control vector, pKCL20, was made by self-ligation of the SpeI-NcoI-cut and blunt-ended pKCL2 vector. For construction of serially truncated promoter reporter plasmids, $P_{DAO1in}$ with 1.7-kb, 1.2 kb, 1.0-kb, 0.7-kb and 0.4-kb was amplified using pKCLD2 as the template, Rt287Nr as the reverse primer and Rt315S, Rt314S, Rt120S, Rt313S and Rt117S as forward primer, respectively. The PCR products were treated as above to construct plasmids pKCLD4 to pKCLD8, containing $P_{DAO1in}$ promoter of approximately 1.7-kb, 1.2 kb, 1.0-kb, 0.7-kb and 0.4-kb in length, respectively (FIG. 5A).

$P_{DAO1int2}$ is mutant of the 0.7 kb intron 1-containing $P_{DAO1}$ with the original translation initiation codon changed to ATC by oligo-directed site mutagenesis. $P_{DAO1int3}$ was made by converting all cytosine residues in motif 2 of $P_{DAO1int2}$ to adenine while $P_{DAO1int4}$ is a mutant with the 24 nt motif 2 deleted. All mutations were made by two-step fusion PCRs. plasmid pKCLD7 was used as the template for PCR of DAO1 promoter fragments. For promoter $P_{DAO1int2}$, oligo pairs SFGFPSEQ/Rt327r and Rt328f/LUC2U were used to make the 0.8 kb and 0.4 kb DNA fragment, respectively. Fusion PCR of above DNA fragments were performed using oligos of Rt313S and Rt287Nr, and the resultant 0.7 kb PCR products were digested with SpeI-NcoI and ligated with the SpeI-NcoI-linearized pKCL2 vector to create plasmid pKCLD71.

Similarly, oligo pairs SFGFPSEQ/Rt329r and Rt330f/LUC2U were used for the amplification of the 0.8 kb upstream and 0.3 kb downstream DNA fragment of $P_{DAO1int3}$, respectively. And oligo pairs SFGFPSEQ/Rt329r and Rt331f/LUC2U were used for the 0.8 kb upstream and 0.3 kb downstream DNA fragment of $P_{DAO1int4}$, respectively. Plasmid pKCLD72 and pKCLD73 were generated using the same procedure of fusion PCR and plasmid construction as pKCLD71.

Example 3

Analysis of Promoter Activity

The T-DNA constructs were transformed into agrobacterium cells by electroporation (2.5 kV, 25 µF, 400Ω) and selected on 2YT agar medium supplemented with streptomycin (100 µg/ml). *Agrobacterium tumefaciens*-mediated transformation (ATMT) of *R. toruloides* was performed as previously described (30). To avoid positional effects, all constructs were knock-in into the CAR2 locus using the KU70 mutant strain (Ku70e) (7), which was conveniently done by selecting albino transformants (FIG. 2C).

Yeast strains transformed with $P_{DAO1inx}$::RtLUC2 cassettes were cultured in YPD broth to mid-exponential phase. Cells were water-washed twice and resuspended in MinABs plus 70 mM of either D-alanine or L-alanine to a cell optical density at 600 nm ($OD_{600}$) of 0.5 and continued culturing at 30° C., 250 rpm for 21 hr. Cells were harvested, washed and resuspended in PBS buffer supplemented with 1 mM DTT, 3 mM β-mercaptoethanol and 1 mM PMSF (pH7.4) supplemented with equal volume of 0.5 mm glass beads (Sigma-Aldrich, USA), and lysed with FastPrep 24™ 5 G (MP Biomedicals, Irvine, Calif., USA) for 40 seconds. The protein concentration and luciferase activity was determined using Bradford method and a commercial luciferase assay kit (Promega, USA) under the supplier's protocol, respectively. All data was measured and acquired with the Infinite M200 plate reader coupled with the iCycler software (version 3.0, Tecan, Salzburg, Austria). All experiments were performed in both biological and statistical triplicates. For determination of relative promoter activity (RPA), luminescence value was subtracted against the blank or negative control (promoter-less strain), normalized against the protein concentration, then normalized against either the values of $P_{GPD1}$ or the maximum reading.

Example 4

Extraction of Genomic DNA and Total RNA

Genomic DNA from *R. toruloides* was extracted using the MasterPure-Yeast DNA and RNA Purification Kits, respectively (Epicenter, Singapore). The concentrations of DNA or RNA samples were determined with NanoDrop® ND-1000 Spectrophotometer (Nanodrop Technologies, Wilmington, USA) and the integrity of the extracted nucleic acids were checked by agarose gel electrophoresis.

Example 5

Southern Blot Analysis

For Southern blot analysis, genomic DNA (10 µg) was digested with PstI and separated by electrophoresis in 0.8% agarose gel. Southern hybridization was performed using DIG High Prime DNA Labeling and Detection Starter Kit according to manufacturer's instruction (Roche Diagnostics, Ind., USA), and the DIG-labeled probe was partial DNA fragment of hpt-3 amplified using oligos HptRU and HptRSL2 (Table 1).

Example 6

Quantitative Reverse Transcription PCR (qRT-PCR)

Total RNA was treated with DNase I (Roche Diagnostics) and recovered by ethanol precipitation to remove the trace DNA. cDNA was synthesized using the iScript™ Reverse Transcription Supermix for RT (Bio-Rad, USA) and real-time PCR was conducted in ABI PRISM 7900HT Sequence Detection System (Life Technologies, USA) using the ABI SYBR® Select Master Mix (Life Technologies, USA). PCR conditions were as followed: an initial 50° C. for 2 min and 95° C. denaturation step for 10 min followed by 40 cycles of denaturation at 95° C. for 15 s, annealing at 60° C. for 1 min. Triplicates were used for all qRT-PCR analyses. The data was acquired using the software SDS 2.4 (Applied Biosystems, Life Technologies, USA) and relative gene expression was calculated against the reference gene ACT1 (nucleotide sequence: SEQ ID NO:89; amino acid sequence: SEQ ID NO:90) with the 2-ΔΔCt method through the RQ Manager software v1.2.1 (Applied Biosystems, USA).

Example 7

Identification of DAO1 in *R. Toruloides* ATCC 10657

Two DAO1 sequences from *Rhodotorula* species were obtained with the GenBank Accession Nos. DM380716 and Z71657 (32), and their homolog in *R. glutinis* ATCC 204091 was identified through the BLASTn search at NCBI. The DAO1 gene (Gen Bank Accesion No. EGU13479.1) in the target strain is located on the sequencing scaffold #23. To achieve the full-length cDNA sequence, 5' and 3'RACE was performed and two approximate 0.5 kb cDNA fragment was obtained (data not shown). Using oligo pair Rt332f and Rt333r (Table 1), the full-length cDNA of DAO1 was successfully amplified by RT-PCR (data not shown). The 1183 nt full-length mRNA transcript contains a 1107 nt ORF, 29 nt 5' UTR (untranslated region) and 47 nt 3' UTR. The ORF is GC-rich with a GC content of 63.0%. Comparison between the cDNA and genomic sequences revealed 6 exons separated by 5 introns (FIG. 2A). All splicing junctions and putative branching point sequences are highly similar to other fungi. The 368-aa protein contains a conserved DAO motif (pfam01266, E-value=4.2E-27), exhibiting high homology to DAAO from other species, with that of *R. toruloides* ATCC 26217 showing the highest identity (UniProtKB/Swiss-Prot acc. no. P80324.1, 94% identity) (data not shown).

Figure 3A:
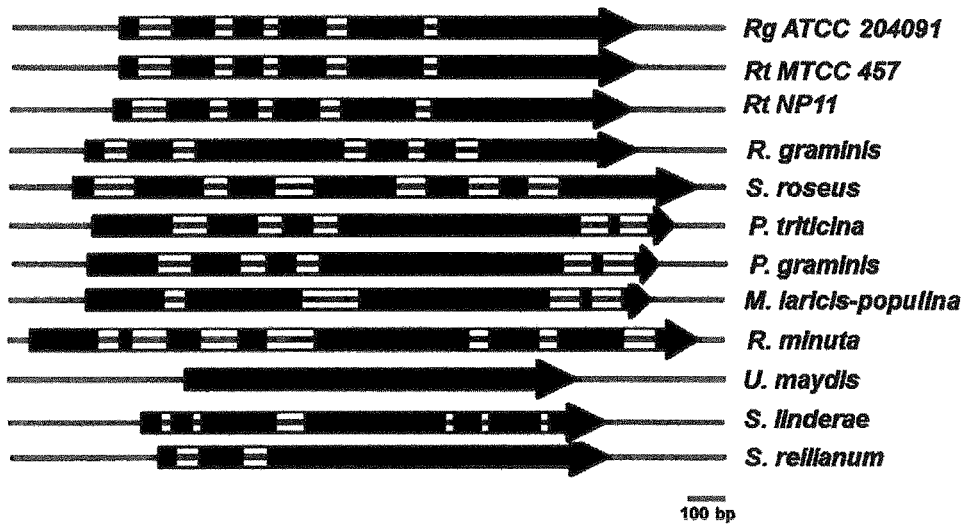
FIGS. 3A-3B show putative DAO1 genes and proteins of Pucciniomycotina and Ustilagiomycotina subphyla.
Figure 3B:
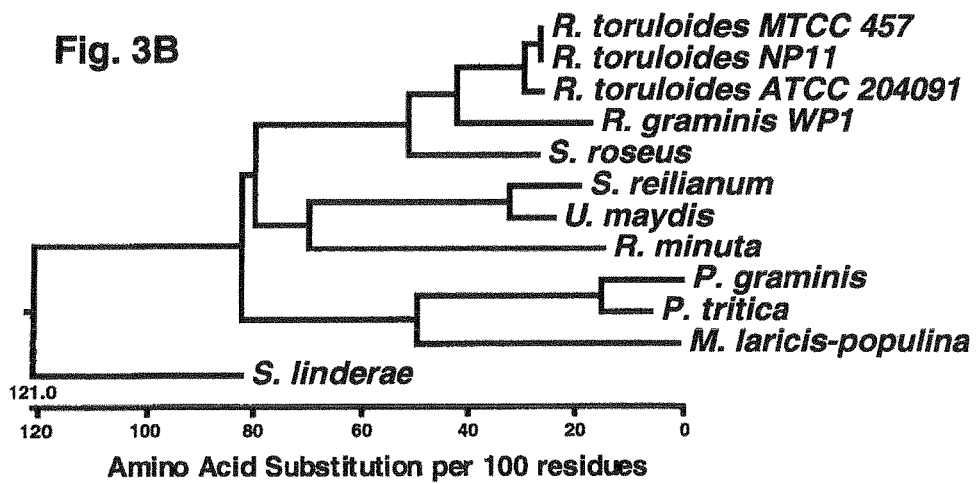

Based on BLAST search, several putative Dao1 encoding genes from Pucciniomycotina and Ustilagiomycotina subphyla were identified and their mRNA splicing patterns were manually annotated. The genes contain 4-7 introns although the putative DAO gene of *U. maydis* is intron-free and *S. reilianum* homologue contains 2 short introns (FIG. 3A). Unrooted phylogenetic tree analysis revealed that Dao1 from Pucciniomycotina subphyla can be separated into two clades: *Rhodosporidium/Rhodotorula* genera and *Sporobolomyces reseus* were clustered in one clade, and Puccinia members and *Melampsora laricis-populina* clustered in the other clade. Those of the Ustilagiomycotina members, are more related to those of the first clade (FIG. 3B).

Example 8

Copy Number of DAO1 and its mRNA Transcripts

Figure 4A:
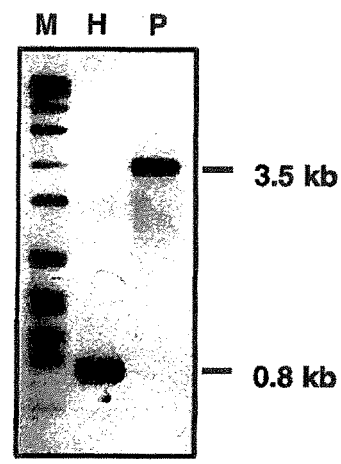
FIGS. 4A-4C show the transcript profiles of DAO1 in *R. toruloides*.
Figure 4B:
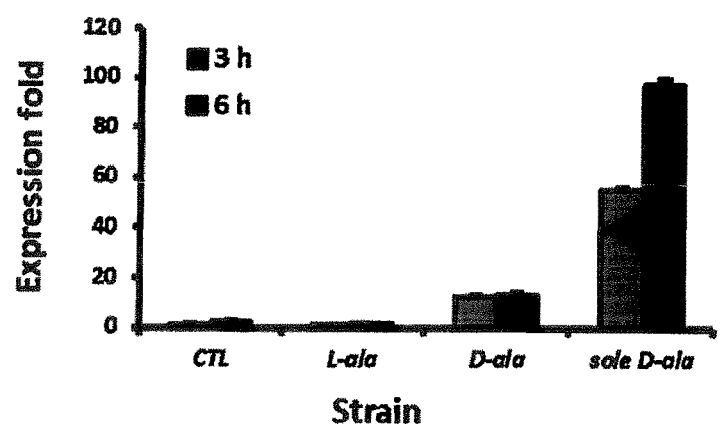
Figure 4C:
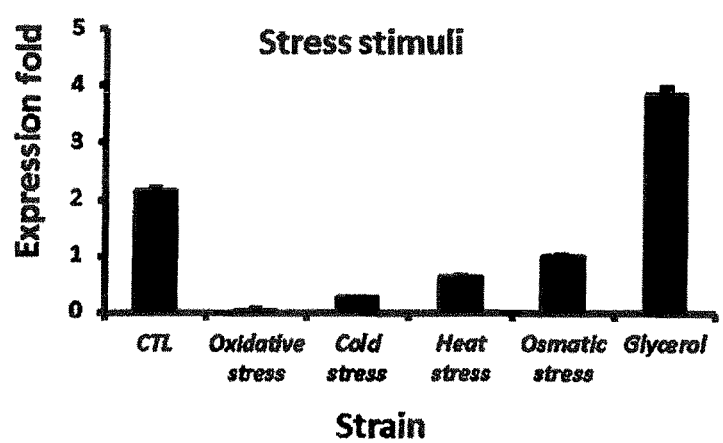

Southern blot analysis revealed a single band when digested with HindIII or PstI, confirming that a single DAO1 gene is encoded in *R. toruloides* genome (FIG. 4A). To investigate the regulation DAO1 gene expression, the mRNA level in cells cultured in YPD medium supplemented with D-alanine or L-alanine levels was quantitated by qRT-PCR using the Actin mRNA (ACT1) as the reference. As expected, DAO1 mRNA expression was negligible when cells were cultured in MinABs medium supplemented with L-alanine or ammonium sulfate as the sole nitrogen source (FIG. 4B). Notably, mRNA level was increased the 12-18 folds cultured in the presence of 70 mM D-alanine and it was further increased to ~100 fold of control medium at 6-hr after D-alanine supplementation if both glucose and ammonium sulfate were omitted in the medium (FIG. 4B). These results confine that the transcription of DAO1 transcription is specifically induced by D-alanine and the presence of extra carbon source strongly inhibits the induction. qRT-PCR of cells cultured under various stress stimuli showed that the transcription of DAO1 was significantly repressed by all stress stimuli tested while glycerol as the sole carbon source appeared to enhance DAO1 transcription compared to that of glucose (FIG. 4C).

Example 9

Identification of Potential Cis-Acting Elements in DAO1 Promoter

To understand the regulation of DAO1 transcription, upstream sequences (~1.0 kb) of DAO1 genes from several basidiomycetous fungi were sent to the MEME server (http colon slash slash meme dot nbcr dot net/meme/) to search for potential cis-acting elements for the gene regulation. The results revealed three conserved motifs. Motif 1 has a consensus sequence of AGGNNGNAGN$_{11}$GANGANGG (SEQ ID NO:6), located most closely to the transcriptional initiation (FIGS. 5A and 5C).

Example 10

Luciferase Reporter Assay of DAO1 Promoters

To investigate the effects of the intron 1 and motif 1 on DAO1 transcription, several mutants of the DAO1 promoter were used for drive the expression of LUC-2, which is a luciferase gene synthetized by Genescript according to the codon preference of *Rhodosporidium* and *Rhodotorula*. In particular, the 2.0 kb intron-less promoter (P$_{DAO1}$), a 2.2 kb intron 1-containing promoter (P$_{DAO1in}$) and a 2.2 kb motif 1-deficient mutant promoter P$_{DAO1int}$ which was made by fusion PCR of two split PCR fragments of the promoter, was cloned into pKCL2 individually. The reporter cassettes (FIG. 6A) were integrated into the CAR2 locus to avoid positional effects. As CAR2 encodes the bifunctional enzyme phytoene synthase and lycopene cyclase that is functionally involved in the biosynthesis of carotenoids in *R. toruloides*, strains with a knock-in LUC-2 reporter cassette can be easily identified by the loss of red carotenoid pigment (7). Southern blot analysis was used to further verify the knock-in strains used. Cells were cultured for 21 hr in MinABs medium supplemented of D-alanine or L-alanine. Results showed that the intron 1 containing P$_{DAO1in}$ promoter was about 5-fold stronger than the intron-less P$_{DAO1}$ when D-alanine was used as the inducer. In addition, the motif 1-deficient mutant P$_{DAO1int}$ showed severe de-repression of promoter activity because MinABs medium with L-alanine as the sole carbon and nitrogen source exhibited much higher luciferase expression level (FIG. 6B). These data confirm that both intron 1 and motif 1 play an important role in the regulation of DAO1 transcription by D-alanine.

Figure 6A:
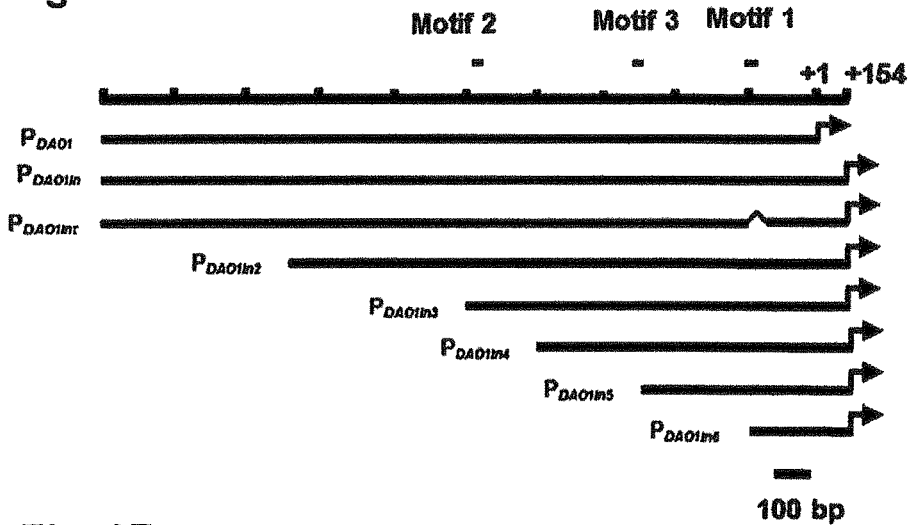
FIGS. 6A-6C show the functional dissection of DAO1 promoter.
Figure 6B:
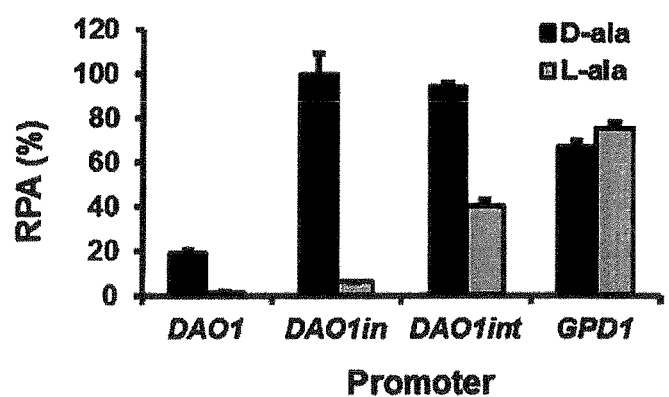
Figure 6C:
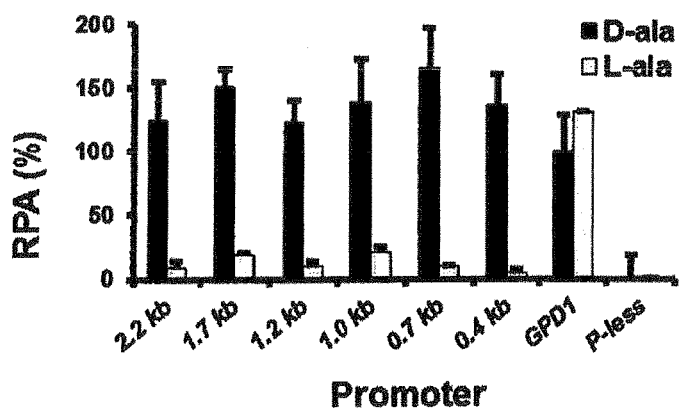

To further characterize the DAO1 promoter, nested deletion of the 2 kb $P_{DAO1in}$ were performed (FIG. 6A and Example 2). The 1.7 and 0.7 kb versions appeared to have slightly increased activity when D-alanine was used as the inducer. However, the 0.4 kb fragment appeared to be the best promoter as it showed similar activity to 2.2 kb version while maintaining the lowest basal activity in L-alanine containing medium (FIG. 6C). Thus, the 0.7 and 0.4 kb intron 1 containing fragments are most preferable fragments for use as promoter for D-alanine inducible gene expression system.

Example 11

Effects of Medium Carbon and Nitrogen Sources on DAO1 Promoter Activity

To investigate the effects of carbon and nitrogen sources on promoter activity, 3 strains with 2.2 kb intron 1-containing DAO1 promoter ($P_{DAO1in}$) knocked in at the CAR2 locus were cultured in the modified MinAB medium (MinABs), which had glucose and ammonium sulfate supplemented to the basal medium MinAB when necessary. Best luciferase expression was observed with MinABs supplemented with 70 mM D-alanine only. The expression was reduced about 5-fold when equal level of L-alanine was added as the competitor after 21 hr culture (FIG. 7A). Ammonium sulfate (70 mM) alone had little effect while glucose at 10 g/L reduced the activity by half. Strikingly, supplementation of both glucose (10 g/L) and ammonium sulfate (70 mM) lead to a drastic repression DAO1 in promoter activity. D-alanine as low as 20 mM was effective in driving expression of the reporter gene although high concentrations continued to enhance the activity (FIG. 7B). The concentrations of glucose (10-100 g/L) and ammonium sulfate (5-50 mM) showed only marginal effects (FIGS. 7C and 7D).

Example 12

Use of Different D-Amino Acids as Inducers

Figure 8:
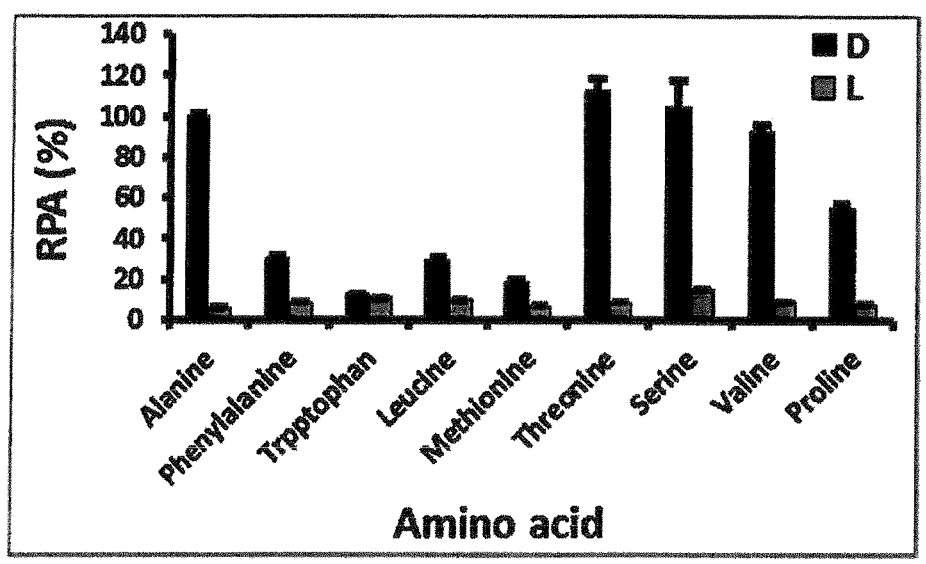
FIG. 8 shows the effects of different D-amino acids on the induction of DAO1 promoter. All promoter activities were assayed after 21 h induction and each amino acid was supplemented as the sole carbon and nitrogen source to MinABs medium with the same concentration of 70 mM.

It has been reported previously that the *Rhodotorula gracilis* D-amino acid oxidase exhibited high substrate affinity to several neutral D-amino acids (33). Here, substrate selectivity of the 2.2 kb DAO1 promoter ($P_{DAO1in}$) reporter strains was investigated on their inducibility by different D-amino acids. Luciferase assay of cells cultured in Min-ABs supplemented with 70 mM of the D-amino acids as the sole carbon and nitrogen source revealed that the promoter was most preferably induced by D-alanine as it showed the best strength and lowest background expression although D-threonine, D-serine, D-valine and D-proline were similarly effective. Other D-amino acids such as D-leucine, D-phenylalanine, D-tryptophan and D-methionine were significantly less effective (FIG. 8).

Example 13

Identification of Cis-Acting Elements in Intron 1 of DAO1 Gene

As intron 1 strongly enhanced the promoter activity (FIG. 6B), we sought to identify the cis-acting element for this activity. Analysis of intron 1 sequences of DAO1 genes from several *Rhodosporidium/Rhodotorula* species at the MEME server (http colon slash slash meme dot nbcr dot net/meme/) for potential cis-acting elements revealed a conserved CT-rich motif (FIG. 9A) with a consensus sequence of T(T/C) TCCC(T/C)CTCC(T/C)CCCCAC(A/T)(C/T) CCGA (SEQ ID NO:7), which was named motif 2 (FIG. 9B). A similar motif has been found in the GPD1 promoter and is known to be an important cis-acting element in fungi (30). To demonstrate the function of this motif, 3 more mutants of the 0.7 kb $DAO1_{in}$ promoter were created: $DAO1_{in2}$ where the original translation initiation codon was changed to ATC so that no additional N-terminal residues are translated in the protein to be expressed; $DAO1_{in3}$ where the all cytosine residues in motif 2 of $DAO1_{in2}$ were changed to adenine and $DAO1_{in4}$ where the 24 nt motif 2 in $DAO1_{in2}$ was deleted. (See example 2.) $DAO1_{in2}$ was essentially the same as $DAO1_{in}$, suggesting that the translation of the initial 16 aa was dispensable for promoter activity and regulation. However, $DAO1_{in3}$ and $DAO1_{in4}$ showed severely reduced activity in both D and L-alanine supplemented MinABs media. This suggests that motif 2 is a binding site for general transcriptional enhancer.

Example 14

Effects of DAO1 Knockout on DAO1in Promoter Activity

Figure 10A:
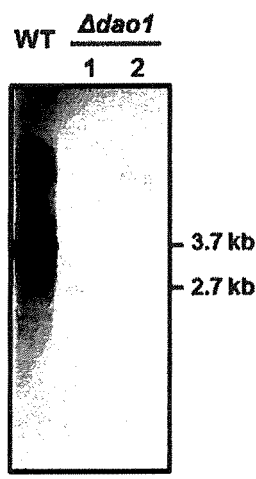
FIG. 10A-C show the effects of DAO1 knockout on DAO1in promoter activity.
Figure 10B:
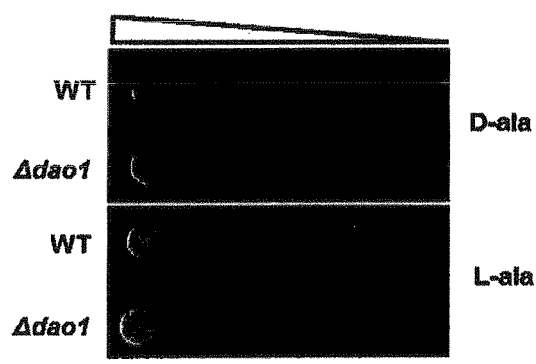
Figure 10C:
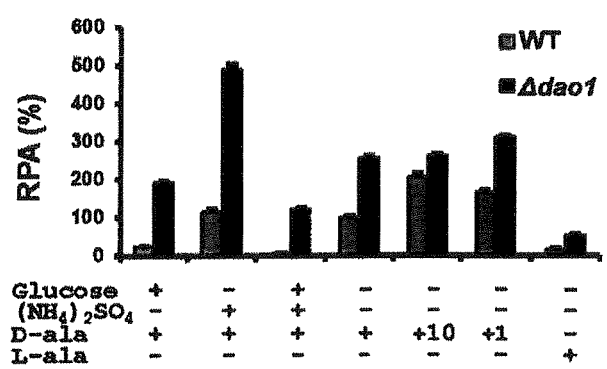

DAO1 knockout mutants (Δdao1) was created according to the method of Koh et al (7). The deletion of DAO1 gene was confirmed by Southern blotting (FIG. 10A). The mutants are significantly compromised in growth when D- or L-alanine was used as the sole carbon source (FIG. 10B). Notably, Δdao1 showed significantly higher induction level of luciferase reporter that the Wt cells. Importantly, strong inducible expression of the reporter gene was achievable even in the presence of high levels of carbon (glucose 10 g/L), and nitrogen source) ammonium sulfate 70 mM). The promoter activity in Δdao1 was 7.8 and 4.2 folds higher than in Wt when supplemented with 10 g/L glucose and) and 70 mM ammonium sulfate respectively. The difference was enhanced to 17 fold when both 10 g/L glucose and 70 mM ammonium sulfate were added to the medium (FIG. 10C).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Sampaio J P, Gadanho M, Bauer R, Weiß M: Taxonomic studies in the Microbotryomycetidae: *Leucosporidium golubevii* sp. nov., *Leucosporidiella* gen. nov. and the new orders *Leucosporidiales* and *Sporidiobolales*. *Mycol Prog* 2003, 2(1):53-68.
2. Zhao X, Wu S, Hu C, Wang Q, Hua Y, Zhao Z K: Lipid production from Jerusalem artichoke by *Rhodosporidium toruloides* Y4. *J Ind Microbiol Biotechnol* 2010, 37(6): 581-585.
3. Liu H, Zhao X, Wang F, Li Y, Jiang X, Ye M, Zhao Z K, Zou H: Comparative proteomic analysis of *Rhodosporidium toruloides* during lipid accumulation. *Yeast* 2009, 26(10):553-566.
4. Turcotte G, Kosaric N: Biosynthesis of lipids by *Rhodosporidium toruloides* ATCC 10788. *J Biotechnol* 1988, 8(3):221-237.
5. Liu Y, Koh C M J, Sun L, Hlaing M M, Du M, Peng N, Ji L: Characterization of glyceraldehyde-3-phosphate dehydrogenase gene RtGPD1 and development of genetic transformation method by dominant selection in oleaginous yeast *Rhodosporidium toruloides*. *Appl Microbiol Biotechnol* 2013, 97(2): 719-729.
6. Peng N, Cheng, H-I, Ji, L.: POLYNUCLEOTIDE SEQUENCES FROM *RHODOSPORIDIUM* AND *RHODOTORULA* AND USE THEREOF. In. USA: Temasek Life Sciences Laboratory.
7. Koh C M, Liu Y, Du M, Ji L: Molecular characterization of KU70 and KU80 homologues and exploitation of a KU70-deficient mutant for improving gene deletion frequency in *Rhodosporidium toruloides*. *BMC Microbiology* 2014, 14(1):50.
8. Terpe K: Overview of bacterial expression systems for heterologous protein production: from molecular and biochemical fundamentals to commercial systems. *Appl Microbiol Biotechnol* 2006, 72(2):211-222.
9. Hollenberg C P, Gellissen G: Production of recombinant proteins by methylotrophic yeasts. *Current Opinion in Biotechnology* 1997, 8(5):554-560.
10. Kim S W, Keasling J: Metabolic engineering of the nonmevalonate isopentenyl diphosphate synthesis pathway in *Escherichia coli* enhances lycopene production. *Biotechnology and bioengineering* 2001, 72(4):408-415.
11. Pollegioni L, Piubelli L, Sacchi S, Pilone M S, Molla G: Physiological functions of D-amino acid oxidases: from yeast to humans. *Cell Mol Life Sci* 2007, 64(11):1373-1394.
12. Pollegioni L, Molla G, Sacchi S, Rosini E, Verga R, Pilone M S: Properties and applications of microbial D-amino acid oxidases: current state and perspectives. *Appl Microbiol Biotechnol* 2008, 78(1):1-16.
13. Simonetta M P, Vanoni M A, Casalin P: Purification and properties of d-amino-acid oxidase, an inducible flavoenzyme from <i>Rhodotorula gracilis</i>. *Biochimica et Biophysica Acta (BBA)-Protein Structure and Molecular Enzymology* 1987, 914(2):136-142.
14. Abad S, Nahalka J, Winkler M, Bergler G, Speight R, Glieder A, Nidetzky B: High-level expression of *Rhodotorula gracilis*D-amino acid oxidase in *Pichia pastoris*. *Biotechnol Lett* 2011, 33(3):557-563.
15. Boselli A, Piubelli L, Molla G, Pilone M S, Pollegioni L, Sacchi S: Investigating the role of active site residues of *Rhodotorula gracilis*D-amino acid oxidase on its substrate specificity. *Biochimie* 2007, 89(3):360-368.
16. Caldinelli L, Molla G, Pilone M S, Pollegioni L: Tryptophan 243 affects interprotein contacts, cofactor binding and stability in D-amino acid oxidase from *Rhodotorula gracilis*. *The FEBS journal* 2006, 273(3):504-512.
17. Boselli A, Piubelli L, Molla G, Sacchi S, Pilone M S, Ghisla S, Pollegioni L: On the mechanism of *Rhodotorula gracilis*D-amino acid oxidase: role of the active site serine 335. *Biochim Biophys Acta* 2004, 1702(1):19-32.
18. Pollegioni L, Harris C M, Molla G, Pilone M S, Ghisla S: Identification and role of ionizing functional groups at the active center of *Rhodotorula gracilis*D-amino acid oxidase. *FEBS Lett* 2001, 507(3):323-326.
19. Hsieh H C, Kuan I C, Lee S L, Tien G Y, Wang Y J, Yu C Y: Stabilization of D-amino acid oxidase from *Rhodosporidium toruloides* by immobilization onto magnetic nanoparticles. *Biotechnol Lett* 2009, 31(4):557-563.
20. Wang S J, Yu C Y, Kuan I C: Stabilization of native and double D-amino acid oxidases from *Rhodosporidium toruloides* and *Trigonopsis variabilis* by immobilization on streptavidin-coated magnetic beads. *Biotechnol Lett* 2008, 30(11):1973-1981.
21. Kuan I, Liao R, Hsieh H, Chen K, Yu C: Properties of *Rhodotorula gracilis*D-amino acid oxidase immobilized on magnetic beads through his-tag. *J Biosci Bioeng* 2008, 105(2):110-115.
22. Upadhya R, Nagajyothi, Bhat S G: Stabilization of D-amino acid oxidase and catalase in permeabilized *Rhodotorula gracilis* cells and its application for the preparation of alpha-ketoacids*. *Biotechnology and Bioengineering* 2000, 68(4):430-436.
23. Molla G, Motteran L, Piubelli L, Pilone M S, Pollegioni L: Regulation of D-amino acid oxidase expression in the yeast *Rhodotorula gracilis*. *Yeast* 2003, 20(12):1061-1069.
24. Carthew R W, Sontheimer E J: Origins and mechanisms of miRNAs and siRNAs. *Cell* 2009, 136(4):642-655.
25. Eamens A, McHale M, Waterhouse P: The Use of Artificial MicroRNA Technology to Control Gene Expression in *Arabidopsis thaliana*. In: *Arabidopsis Protocols*. Edited by Sanchez-Serrano J J, Salinas J, vol. 1062: Humana Press; 2014: 211-224.
26. Lazo G R, Stein P A, Ludwig R A: A DNA transformation-competent *Arabidopsis genomic* library in *Agrobacterium*. *Nature Biotechnol* 1991, 9(10):963-967.
27. Cai L, Sun L, Fu L, Ji L: MEDIA COMPOSITIONS, SELECTION METHODS AND *AGROBACTERIUM* STRAINS FOR TRANSFORMATION OF PLANTS. In: US Patent 20,120,246,759; 2012.
28. Watson B, Currier T C, Gordon M P, Chilton M, Nester E: Plasmid required for virulence of *Agrobacterium tumefaciens*. *J Bacteriol* 1975, 123(1):255-264.
29. Lee L Y, Gelvin S B: T-DNA binary vectors and systems. *Plant Physiol* 2008, 146(2):325-332.

30. Liu Y, Koh C M, Sun L, Hlaing M M, Du M, Peng N, Ji L: Characterization of glyceraldehyde-3-phosphate dehydrogenase gene RtGPD1 and development of genetic transformation method by dominant selection in oleaginous yeast *Rhodosporidium toruloides*. *Appl Microbiol Biotechnol* 2013, 97(2):719-729.
31. Szewczyk E, Nayak T, Oakley C E, Edgerton H, Xiong Y, Taheri-Talesh N, Osmani S A, Oakley B R: Fusion PCR and gene targeting in *Aspergillus nidulans*. *Nat Protoc* 2006, 1(6):3111-3120.
32. Pollegioni L, Molla G, Campaner S, Martegani E, Pilone M S: Cloning, sequencing and expression in *E. coli* of a D-amino acid oxidase cDNA from *Rhodotorula gracilis* active on cephalosporin C. *J Biotechnol* 1997, 58(2):115-123.
33. Pollegioni L, Falbo A, Pilone M S: Specificity and kinetics of *Rhodotorula gracilis* D-amino acid oxidase. *Biochim Biophys Acta* 1992, 1120(1):11-16.
Mysara, M. et al. (2011). MysiRNA-designer: a workflow for efficient siRNA design. *PLOS one* 6(10):e25642.
Wesley, S. V. et al. (2001). Construct design for efficient, effective and high-throughput gene silencing in plants. *Plant J* 27:581-590.
Yan, P. et al. (2012). High-throughput construction of intron-containing hairpin RNA vectors for RNAi in plants. *PLOS one* 7(5):e38186.
Zuo, J., et al., *Chemical-regulated, site-specific DNA excision in transgenic plants*. Nat Biotechnol, 2001. 19(2): p. 157-61.

What is claimed is:

1. A D-amino acid inducible gene expression system operable in a transgenic fungal cell comprising a nucleic acid construct comprising a D-amino acid inducible promoter operably linked to a heterologous polynucleotide, wherein the promoter is selected from the group consisting of:
   (a) a promoter having at least 80% identity to the nucleotide sequence set forth in SEQ ID NO:94;
   (b) a promoter having at least 80% identity to the nucleotide sequence set forth in SEQ ID NO:95;
   (c) a promoter having at least 80% identity to the nucleotide sequence set forth in SEQ ID NO:96;
   (d) a promoter having at least 80% identity to the nucleotide sequence set forth in SEQ ID NO:97; and
   (e) a promoter having at least 80% identity to the nucleotide sequence set forth in SEQ ID NO:5, and
   wherein the promoter comprises a promoter motif comprising the nucleotide sequence set forth in SEQ ID NO:6.

2. The expression system of claim 1, wherein the fungal cell is a transgenic fungal cell of a species of *Rhodsporidium* genus or *Rodottorula* genus.

3. The expression system of claim 1, wherein the transgenic fungal cell comprises a mutant D-amino acid oxidase gene having no or reduced D-amino acid oxidase activity compared to a fungal cell comprising a wild type D-amino acid oxidase gene.

4. The expression system of claim 1, wherein the heterologous polynucleotide is operably linked to a transcription terminator.

5. The expression system of claim 1, wherein the nucleic acid construct contains a nucleotide sequence having at least 75% identity to the nucleotide sequence set forth in SEQ ID NO:7.

6. The expression system of claim 5, wherein the nucleotide sequence is an intron operably linked to the inducible promoter and operably linked to the heterologous polynucleotide.

7. The expression system of claim 5, wherein the nucleotide sequence is an intron inserted into the 5' region of the heterologous polynucleotide.

8. The expression system of claim 5, wherein the nucleotide sequence is an intron inserted into the 5' UTR of the inducible promoter.

9. The expression system of claim 5, wherein the nucleotide sequence is part of the coding sequence of the heterologous polynucleotide.

10. The expression system of claim 5, wherein the nucleotide sequence is selected from the group consisting of SEQ ID NO:56, SEQ ID NO:57, SEQ ID NO:58 and SEQ ID NO:59.

11. The expression system of claim 1, wherein the heterologous polynucleotide encodes a protein of interest.

12. The expression system of claim 1, wherein the heterologous polynucleotide encodes an RNA molecule for down regulating a target gene of interest.

13. A transgenic fungal cell comprising the expression system of claim 1.

14. A composition comprising the transgenic fungal cell of claim 13 and a culture medium comprising a D-amino acid.

15. The composition of claim 14, wherein the D-amino acid is D-alanine, D-threonine, D-serine, D-valine or D-proline.

16. The composition of claim 14, wherein the concentration of the D-amino acid in the culture medium is from about 0.1 mM to about 100 mM.

17. A method for preparing a transgenic fungal cell comprising:
    (a) introducing the expression system of claim 1 into a fungal cell and
    (b) selecting a transgenic fungal cell which comprises the nucleic acid construct.

18. A method of inducible expression of a polynucleotide in a fungal cell comprising culturing the transgenic fungal cell of claim 13 in a culture medium comprising a D-amino acid to induce expression of the heterologous polynucleotide.

19. The method of claim 18, wherein the D-amino acid is D-alanine, D-threonine, D-serine, D-valine or D-proline.

20. The method of claim 18, wherein the concentration of the D-amino acid in the culture medium is from about 0.1 mM to about 100 mM.

* * * * *

SEQUENCE LISTING

```
<160> NUMBER OF SEQ ID NOS: 97

<210> SEQ ID NO 1
<211> LENGTH: 2181
<212> TYPE: DNA
<213> ORGANISM: Rhodosporidium toruloides
<220> FEATURE:
<221> NAME/KEY: misc_feature
<222> LOCATION: (1803)..(1830)
<223> OTHER INFORMATION: DNA motif 1
<220> FEATURE:
<221> NAME/KEY: misc_feature
<222> LOCATION: (2024)..(2024)
<223> OTHER INFORMATION: G may be replaced by C, A or T
<220> FEATURE:
<221> NAME/KEY: Intron
<222> LOCATION: (2062)..(2169)
<220> FEATURE:
<221> NAME/KEY: misc_feature
<222> LOCATION: (2069)..(2092)
<223> OTHER INFORMATION: DNA motif 2
<220> FEATURE:
<221> NAME/KEY: misc_feature
<222> LOCATION: (2176)..(2181)
<223> OTHER INFORMATION: NcoI site

<400> SEQUENCE: 1
cttcccggtc tcgtatcgag cggaagacat ccccctcttc ctcgctcaga ttgccgctct      60
cctgcaaggc cagcagtggg gcgtcggtgc gtgcccaact cgtctgaagt ggccaaatgg     120
ctgacagtgc tcccgcaggt cacgacgctg ccgccatcct tcgcggtctt cggcagcgga     180
agctttgatt ctttcttgcc tctctcggtt gtacaatcgt cgtgctcgcc agtttgttgt     240
tgatatccct agccttgcct tccatactga acaatctaca actcgtcctt cttgcgcggc     300
ggaaagcgct tcagcacctc gttctgcacg tcttgcggca agtactcccc acccggtcct     360
gcccacatca ccggcagatc tgtccgcttc tcatacactg ctggtgaggc aggttgcgag     420
gcgagagagc gctggaccgc ctcgacttct tccattacgc gaaggaggtt gccgccgatc     480
aagtctgcta ggtcgtcttc cgtccatcct cgtcgcaaca actccgcaat ctgcagagac     540
gaggtagtca gcacatgtca tagctgaaga agcaagcgat gcgcaccaag ttcggaaact     600
tcgacgcgtc ctcaagcccc tcaacactcg agcgcatacc gtcaaagtca gacccgagac     660
cgacgtgctt cttgccgcag acggaggcga tgtactcgat atgatcggcg acacggattt     720
gcgtggcgtt cgtagggtcg ataaaggaag ggtagaagac gaccattctg cgagacgcga     780
aggtcagccg gaaacttctg acgacaggaa gtaacgtcgt acgcacacga tgccgtggtt     840
ctggtgctcg cctggcccga tcagctgaag aacttcctct gggacgtttc gcgggtggtc     900
gtggatcgct cgcgcgccag agtgcgagaa gatgacgggc gcaacgctga gttcgagggc     960
```

```
ctgctcgcaa atcgtcagct aaagctcgaa agtgttgaag cgcggtgcgc acgtcgagca    1020
tggtctgatc gcttgtgtgc gagaggtcga ccatcatgcc gagcctgttc agctccggta    1080
caagctcgcg cccgaaggcg gtcaggccgt tcccgtcgtg tacaggctcg ataggagagc    1140 cgtcccggc ggaagaggcg aaggctgtga gaaaaacccg tcaacagagc ggaagaaggc     1200
cgagaggtcg cctcgcctca caagtgtggc aggtgtgcgt gagcgtaagg taccgcacgc    1260
cgagttgctg aaagaggcgt aggatggcca gcgagttcat caggtgatgc gagctgtagg    1320
aagagcgggt tagcgggagg atgtcggtag agactgttcg tacaaacccc tctagcccaa    1380
tcaaggacgc gatcttcccc tccgcgaacg cactccgcac ctcgtccgcc gttcgagcga    1440
gcgccatctc ctcaggatag tgctccacca tccgatgaat aaggtcgacg ctctcgagtg    1500
cccactcgac cgcgttcgtg ggctcaagga agtcctcccc cgtcggctgc gcatcacacg    1560
gagcatacgc aacatggaac aagcctccta cgcgtccttg acgcaacttc gggaggtcga    1620
catggcctgc aagaccggtc gcaagttcag ggaggacgtc gagcggtctc ggcagaggt     1680 ggcgagcgac gtaggggagg tcgacgtgtc cgtctatgag tgggtggcgt ttcaggatcc    1740
cgcgggcctc agcgagcaag gactcgttgg gcaaagtgaa ggtgtactga tgagcggttg    1800
cgaggccgca gagcagcgct gcgacgacgg gaagcttcgg cacgagcatg actgtgagta    1860
gtagtccaag gagaacagcg cagagtcggc aggagggcac atggaggcag agcgtggggc    1920
ggaggaggca gatggggagt cgcgctgggg gacgagaggg tgccgctcga ccaactgctc    1980
tctttcgctc ttgctgctgc ttgtactgct cgaacgacgc catgcattca cagaagcgcg    2040
tcgttgtcct cggatcaggc ggtgcgtctt tccctctcct ccccacaccc gacagttctc    2100
gaggaggagt acagcagcga gcgaggctgc cgaggggat ctgggttgac gcagctcttg     2160
attatacagt gattgccatg g                                              2181
```

<210> SEQ ID NO 2
<211> LENGTH: 1701
<212> TYPE: DNA
<213> ORGANISM: Rhodosporidium toruloides
<220> FEATURE:
<221> NAME/KEY: misc_feature
<222> LOCATION: (1323)..(1350)
<223> OTHER INFORMATION: DNA motif 1
<220> FEATURE:
<221> NAME/KEY: misc_feature
<222> LOCATION: (1544)..(1544)
<223> OTHER INFORMATION: G may be replaced by C, A or T
<220> FEATURE:
<221> NAME/KEY: Intron
<222> LOCATION: (1582)..(1689)
<220> FEATURE:
<221> NAME/KEY: misc_feature
<222> LOCATION: (1589)..(1612)
<223> OTHER INFORMATION: DNA motif 2
<220> FEATURE:
<221> NAME/KEY: misc_feature
<222> LOCATION: (1696)..(1701)
<223> OTHER INFORMATION: NcoI site

<400> SEQUENCE: 2

```
aagtctgcta ggtcgtcttc cgtccatcct cgtcgcaaca actccgcaat ctgcagagac      60
gaggtagtca gcacatgtca tagctgaaga agcaagcgat gcgcaccaag ttcggaaact     120
tcgacgcgtc ctcaagcccc tcaacactcg agcgcatacc gtcaaagtca gacccgagac     180
cgacgtgctt cttgccgcag acggaggcga tgtactcgat atgatcggcg acacggattt     240
gcgtggcgtt cgtagggtcg ataaaggaag ggtagaagac gaccattctg cgagacgcga     300
```

```
aggtcagccg gaaacttctg acgacaggaa gtaacgtcgt acgcacacga tgccgtggtt      360
ctggtgctcg cctggcccga tcagctgaag aacttcctct gggacgtttc gcgggtggtc      420
gtggatcgct cgcgcgccag agtgcgagaa gatgacgggc gcaacgctga gttcgagggc      480
ctgctcgcaa atcgtcagct aaagctcgaa agtgttgaag cgcggtgcgc acgtcgagca      540
tggtctgatc gcttgtgtgc gagaggtcga ccatcatgcc gagcctgttc agctccggta      600
caagctcgcg cccgaaggcg gtcaggccgt tcccgtcgtg tacaggctcg ataggagagc      660
cgtccccggc ggaagaggcg aaggctgtga gaaaacccg tcaacagagc ggaagaaggc       720
cgagaggtcg cctcgcctca caagtgtggc aggtgtgcgt gagcgtaagg taccgcacgc      780
cgagttgctg aaagaggcgt aggatggcca gcgagttcat caggtgatgc gagctgtagg      840
aagagcgggt tagcgggagg atgtcggtag agactgttcg tacaaacccc tctagcccaa      900
tcaaggacgc gatcttcccc tccgcgaacg cactccgcac ctcgtccgcc gttcgagcga      960
gcgccatctc ctcaggatag tgctccacca tccgatgaat aaggtcgacg ctctcgagtg     1020
cccactcgac cgcgttcgtg ggctcaagga agtcctcccc cgtcggctgc gcatcacacg     1080
gagcatacgc aacatggaac aagcctccta cgcgtccttg acgcaacttc gggaggtcga     1140
catggcctgc aagaccggtc gcaagttcag ggaggacgtc gagcggtctc cggcagaggt     1200
ggcgagcgac gtaggggagg tcgacgtgtc cgtctatgag tgggtggcgt ttcaggatcc     1260
cgcgggcctc agcgagcaag gactcgttgg gcaaagtgaa ggtgtactga tgagcggttg     1320
cgaggccgca gagcagcgct gcgacgacgg gaagcttcgg cacgagcatg actgtgagta     1380
gtagtccaag gagaacagcg cagagtcggc aggagggcac atggaggcag agcgtggggc     1440
ggaggaggca gatggggagt cgcgctgggg gacgagaggg tgccgctcga ccaactgctc     1500
tctttcgctc ttgctgctgc ttgtactgct cgaacgacgc catgcattca cagaagcgcg     1560
tcgttgtcct cggatcaggc ggtgcgtctt tccctctcct ccccacaccc gacagttctc     1620
gaggaggagt acagcagcga gcgaggctgc cgaggggat ctgggttgac gcagctcttg      1680
attatacagt gattgccatg g                                              1701
```

<210> SEQ ID NO 3
<211> LENGTH: 701
<212> TYPE: DNA
<213> ORGANISM: Rhodosporidium toruloides
<220> FEATURE:
<221> NAME/KEY: misc_feature
<222> LOCATION: (323)..(350)
<223> OTHER INFORMATION: DNA motif 1
<220> FEATURE:
<221> NAME/KEY: misc_feature
<222> LOCATION: (544)..(544)
<223> OTHER INFORMATION: G may be replaced by C, A or T
<220> FEATURE:
<221> NAME/KEY: Intron
<222> LOCATION: (582)..(689)
<220> FEATURE:
<221> NAME/KEY: misc_feature
<222> LOCATION: (589)..(612)
<223> OTHER INFORMATION: DNA motif 2
<220> FEATURE:
<221> NAME/KEY: misc_feature
<222> LOCATION: (696)..(701)
<223> OTHER INFORMATION: NcoI site

<400> SEQUENCE: 3

```
aaggtcgacg ctctcgagtg cccactcgac cgcgttcgtg ggctcaagga agtcctcccc       60
cgtcggctgc gcatcacacg gagcatacgc aacatggaac aagcctccta cgcgtccttg      120
```

```
acgcaacttc gggaggtcga catggcctgc aagaccggtc gcaagttcag ggaggacgtc      180
gagcggtctc cggcagaggt ggcgagcgac gtaggggagg tcgacgtgtc cgtctatgag      240
tgggtggcgt ttcaggatcc cgcgggcctc agcgagcaag gactcgttgg gcaaagtgaa      300
ggtgtactga tgagcggttg cgaggccgca gagcagcgct gcgacgacgg gaagcttcgg      360
cacgagcatg actgtgagta gtagtccaag gagaacagcg cagagtcggc aggagggcac      420
atggaggcag agcgtggggc ggaggaggca gatggggagt cgcgctgggg gacgagaggg      480
tgccgctcga ccaactgctc tctttcgctc ttgctgctgc ttgtactgct cgaacgacgc      540
catgcattca cagaagcgcg tcgttgtcct cggatcaggc ggtgcgtctt tccctctcct      600
ccccacaccc gacagttctc gaggaggagt acagcagcga gcgaggctgc cgaggggat      660 ctgggttgac gcagctcttg attatacagt gattgccatg g                          701

<210> SEQ ID NO 4
<211> LENGTH: 401
<212> TYPE: DNA
<213> ORGANISM: Rhodosporidium toruloides
<220> FEATURE:
<221> NAME/KEY: misc_feature
<222> LOCATION: (23)..(50)
<223> OTHER INFORMATION: DNA motif 1
<220> FEATURE:
<221> NAME/KEY: misc_feature
<222> LOCATION: (244)..(244)
<223> OTHER INFORMATION: G may be replaced with C, A or T
<220> FEATURE:
<221> NAME/KEY: Intron
<222> LOCATION: (282)..(389)
<220> FEATURE:
<221> NAME/KEY: misc_feature
<222> LOCATION: (289)..(312)
<223> OTHER INFORMATION: DNA motif 2
<220> FEATURE:
<221> NAME/KEY: misc_feature
<222> LOCATION: (396)..(401)
<223> OTHER INFORMATION: NcoI site

<400> SEQUENCE: 4
ggtgtactga tgagcggttg cgaggccgca gagcagcgct gcgacgacgg gaagcttcgg       60
cacgagcatg actgtgagta gtagtccaag gagaacagcg cagagtcggc aggagggcac      120
atggaggcag agcgtggggc ggaggaggca gatggggagt cgcgctgggg gacgagaggg      180
tgccgctcga ccaactgctc tctttcgctc ttgctgctgc ttgtactgct cgaacgacgc      240
catgcattca cagaagcgcg tcgttgtcct cggatcaggc ggtgcgtctt tccctctcct      300
ccccacaccc gacagttctc gaggaggagt acagcagcga gcgaggctgc cgaggggat      360 ctgggttgac gcagctcttg attatacagt gattgccatg g                          401

<210> SEQ ID NO 5
<211> LENGTH: 997
<212> TYPE: DNA
<213> ORGANISM: Rhodosporidium toruloides
<220> FEATURE:
<221> NAME/KEY: misc_feature
<222> LOCATION: (779)..(806)
<223> OTHER INFORMATION: DNA motif 1

<400> SEQUENCE: 5
ctgatcgctt gtgtgcgaga ggtcgaccat catgccgagc ctgttcagct ccggtacaag       60
ctcgcgcccg aaggcggtca ggccgttccc gtcgtgtaca ggctcgatag gagagccgtc      120
cccggcggaa gaggcgaagg ctgtgagaaa aacccgtcaa cagagcggaa gaaggccgag      180
```

```
aggtcgcctc gcctcacaag tgtggcaggt gtgcgtgagc gtaaggtacc gcacgccgag    240
ttgctgaaag aggcgtagga tggccagcga gttcatcagg tgatgcgagc tgtaggaaga    300
gcgggttagc gggaggatgt cggtagagac tgttcgtaca aacccctcta gcccaatcaa    360
ggacgcgatc ttcccctccg cgaacgcact ccgcacctcg tccgccgttc gagcgagcgc    420
catctcctca ggatagtgct ccaccatccg atgaataagg tcgacgctct cgagtgccca    480
ctcgaccgcg ttcgtgggct caaggaagtc ctcccccgtc ggctgcgcat cacacggagc    540
atacgcaaca tggaacaagc ctcctacgcg tccttgacgc aacttcggga ggtcgacatg    600
gcctgcaaga ccggtcgcaa gttcagggag gacgtcgagc ggtctccggc agaggtggcg    660
agcgacgtag gggaggtcga cgtgtccgtc tatgagtggg tggcgtttca ggatcccgcg    720
ggcctcagcg agcaaggact cgttgggcaa agtgaaggtg tactgatgag cggttgcgag    780
gccgcagagc agcgctgcga cgacgggaag cttcggcacg agcatgactg tgagtagtag    840
tccaaggaga acagcgcaga gtcggcagga gggcacatgg aggcagagcg tggggcggag    900
gaggcagatg gggagtcgcg ctgggggacg agagggtgcc gctcgaccaa ctgctctctt    960
tcgctcttgc tgctgcttgt actgctcgaa cgacgcc                            997
```

```
<210> SEQ ID NO 6
<211> LENGTH: 28
<212> TYPE: DNA
<213> ORGANISM: Rhodosporidium toruloides
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 6
aggnngnagn nnnnnnnnnn gangangg                                       28

<210> SEQ ID NO 7
<211> LENGTH: 24
<212> TYPE: DNA
<213> ORGANISM: Rhodosporidium toruloides

<400> SEQUENCE: 7
tytcccyctc cycccacwy ccga                                            24

<210> SEQ ID NO 8
<211> LENGTH: 300
<212> TYPE: DNA
<213> ORGANISM: Rhodosporidium toruloides
<220> FEATURE:
<221> NAME/KEY: misc_feature
<222> LOCATION: (27)..(51)
<223> OTHER INFORMATION: ct box
<220> FEATURE:
```

<221> NAME/KEY: misc_feature
<222> LOCATION: (52)..(52)
<223> OTHER INFORMATION: transcription start point
<220> FEATURE:
<221> NAME/KEY: 5'UTR
<222> LOCATION: (52)..(100)
<220> FEATURE:
<221> NAME/KEY: misc_feature
<222> LOCATION: (101)..(102)
<223> OTHER INFORMATION: coding sequence
<220> FEATURE:
<221> NAME/KEY: Intron
<222> LOCATION: (103)..(231)
<220> FEATURE:
<221> NAME/KEY: misc_feature
<222> LOCATION: (232)..(300)
<223> OTHER INFORMATION: coding sequence

<400> SEQUENCE: 8

| | | | | | |
|---|---|---|---|---|---|
| tgagcgaagg | aagccgcatc | gacaagttcg | ctccccttcg | ccctcttccc | catcacccgt | 60 |
| tctcgcctta | cccgctcaga | acaacaccag | atcactcaca | atgtctgtgc | agcatccgcc | 120 |
| ctgaacttgc | cgcatcgtca | gcggtctccc | tcgccctctg | ctgacctcgt | ctcgtcacct | 180 |
| cctccctcat | ccgctcctat | cgcttcccgt | acaccgctgg | gatgctcgca | ggtctgccgg | 240 |
| aaagggatct | gtcaacgtcg | gaatcaacgg | cttcggtcgc | atcggccgca | tcgtcctccg | 300 |

<210> SEQ ID NO 9
<211> LENGTH: 1702
<212> TYPE: DNA
<213> ORGANISM: Rhodotorula graminis WP1

<400> SEQUENCE: 9

| | | | | | |
|---|---|---|---|---|---|
| cgctgcagca | ctagccgctc | ccgctgagcc | agcttgctcc | ctctcgttcg | cactacaatg | 60 |
| gctatcgaca | agcgcgtcgt | cgtcctcggc | accggcggtg | agcccagcc | ctcacactct | 120 |
| cccctcccc | cccacttccg | aggcctgact | cttccctctc | gccctcgcc | tcgcagtggt | 180 |
| cggccttcg | tgcggcctcg | tcctgtcccg | acaaggctac | cgcgtccact | tcatcgcgcg | 240 |
| cgacttgccc | gaggactcga | cctcgcaagg | cttcgcctcc | cctgggcgg | tccgtctcct | 300 |
| cggcctcaac | cctcccattc | ttccctgttt | atagacccga | gctgaccctc | tcgagtacgt | 360 |
| gcacgcaggg | cgccaactgg | acgccgttct | actcgcggga | cgagggccct | cgccaggcca | 420 |
| agtgggagga | ggccacctttt | gctgctgggg | tctcgctcgt | cccgtccggc | ctcgccatgt | 480 |
| ggctcaacga | cacgcgccgc | tacgccgaca | ccgacgccgg | cctcctcggt | cactggtacc | 540 |
| gcgacacggt | ccgcaactac | cgcgagctcc | cgccgagcga | gctgcccaaa | ggcgtcgcgg | 600 |
| ccggcgccgc | gtacgacacc | ctgtcggtca | acgcgccgct | gtactgccag | gcgctcgcga | 660 |
| gggagctgca | gacgctcggc | gcgaccttcg | agcgcaggtc | ggtctcgtcg | atcgagcagg | 720 |
| tgttcgaggg | ccaggacgac | attgcgctcg | tcgtcaacgc | caccgggctc | ggtgcgtcct | 780 |
| ctttcgccga | cctgtccttc | tcctctcctc | gagcagagtc | gctcaccgtg | tcttcgagtg | 840 |
| tttgcaggcg | ccaagtcgat | cgctggcatc | gaggactcgg | cgtgccaccc | agtgcgaggc | 900 |
| cagacggtgc | tcgtcaagtc | cggctgcaag | cgctgcacca | tggactcgtc | gagtgcgtcc | 960 |
| cctcgcgtcc | tctttcggtc | ttggttccgg | acgagactga | cgctgcgctc | gtacagaccc | 1020 |
| tgaggcgccc | gcctacatca | ttccgaggcc | tggcggcgag | gtcatctgcg | gcggcaccta | 1080 |
| tttggtccgt | cccactctct | ctctcgctct | ctcccgacgc | tcgtgcgaga | catgccctga | 1140 |
| ccttgcttcc | gcccatcctc | acgcaggtcg | acgactggga | cctctcgccc | tcggcctcga | 1200 |
| ccgcgcagcg | cattctcacc | cagtgcctcg | cgctcgaccc | gtccatctcg | accgacggca | 1260 |

```
cgctcgacgg aatccacatc ctgcggcaca acgtcgggct gcgccctgcg cgcaccggcg    1320
gaccgcgcgt cgaggtcggc aagctcacgc tgccactcgt gcgctcgacc gagccgggca    1380
cggcgctcgc gctcggaacg gctcgccctg ctcctgcggg cgcgtcgagc gaagcggtgg    1440
gtgcgccgag cgaggcggtc aagcgcgagg tgacgctcgt gcacgcgtac gggttctcga    1500
gcgccggcta ccagcagagc tggggcgtcg cgcaggacgt gctcgggctc gtcgagggcg    1560
agatcgggcc gcctcgagcc tggtggacgc agaggggcaa gctgtagtgc gggtcgtgcg    1620
catcggagcg agtttgtgtc ggccttcgca agttggctcg aatcgcggtg gcggcgcagc    1680
tccctcaacc tcttctctct ct                                             1702
```

<210> SEQ ID NO 10
<211> LENGTH: 389
<212> TYPE: PRT
<213> ORGANISM: Rhodotorula graminis WP1

<400> SEQUENCE: 10

```
Met Ala Ile Asp Lys Arg Val Val Leu Gly Thr Gly Val Val Gly
1               5                   10                  15

Leu Ser Cys Gly Leu Val Leu Ser Arg Gln Gly Tyr Arg Val His Phe
            20                  25                  30

Ile Ala Arg Asp Leu Pro Glu Asp Ser Thr Ser Gln Gly Phe Ala Ser
        35                  40                  45

Pro Trp Ala Gly Ala Asn Trp Thr Pro Phe Tyr Ser Arg Asp Glu Gly
    50                  55                  60

Pro Arg Gln Ala Lys Trp Glu Glu Ala Thr Phe Ala Arg Trp Val Ser
65                  70                  75                  80

Leu Val Pro Ser Gly Leu Ala Met Trp Leu Asn Asp Thr Arg Arg Tyr
                85                  90                  95

Ala Asp Thr Asp Ala Gly Leu Leu Gly His Trp Tyr Arg Asp Thr Val
            100                 105                 110

Arg Asn Tyr Arg Glu Leu Pro Pro Ser Glu Leu Pro Lys Gly Val Ala
        115                 120                 125

Ala Gly Ala Ala Tyr Asp Thr Leu Ser Val Asn Ala Pro Leu Tyr Cys
    130                 135                 140

Gln Ala Leu Ala Arg Glu Leu Gln Thr Leu Gly Ala Thr Phe Glu Arg
145                 150                 155                 160

Arg Ser Val Ser Ser Ile Glu Gln Val Phe Glu Gly Gln Asp Asp Ile
                165                 170                 175

Ala Leu Val Val Asn Ala Thr Gly Leu Gly Ala Lys Ser Ile Ala Gly
            180                 185                 190

Ile Glu Asp Ser Ala Cys His Pro Val Arg Gly Gln Thr Val Leu Val
        195                 200                 205

Lys Ser Gly Cys Lys Arg Cys Thr Met Asp Ser Ser Asn Pro Glu Ala
    210                 215                 220

Pro Ala Tyr Ile Ile Pro Arg Pro Gly Gly Glu Val Ile Cys Gly Gly
225                 230                 235                 240

Thr Tyr Leu Val Asp Asp Trp Asp Leu Ser Pro Ser Ala Ser Thr Ala
                245                 250                 255

Gln Arg Ile Leu Thr Gln Cys Leu Ala Leu Asp Pro Ser Ile Ser Thr
            260                 265                 270

Asp Gly Thr Leu Asp Gly Ile His Ile Leu Arg His Asn Val Gly Leu
        275                 280                 285
```

```
Arg Pro Ala Arg Thr Gly Gly Pro Arg Val Glu Val Gly Lys Leu Thr
    290                 295                 300

Leu Pro Leu Val Arg Ser Thr Glu Pro Gly Thr Ala Leu Ala Leu Gly
305                 310                 315                 320

Thr Ala Arg Pro Ala Pro Ala Gly Ala Ser Ser Glu Ala Val Gly Ala
                325                 330                 335

Pro Ser Glu Ala Val Lys Arg Glu Val Thr Leu Val His Ala Tyr Gly
            340                 345                 350

Phe Ser Ala Gly Tyr Gln Gln Ser Trp Val Ala Gln Asp Val
        355                 360                 365

Leu Gly Leu Val Glu Gly Glu Ile Gly Pro Pro Arg Ala Trp Trp Thr
370                 375                 380

Gln Arg Gly Lys Leu
385

<210> SEQ ID NO 11
<211> LENGTH: 1461
<212> TYPE: DNA
<213> ORGANISM: Rhodosporidium toruloides MTCC 457

<400> SEQUENCE: 11
atgcactctc agaagcgcgt cgttgtcctc ggatcaggcg gtgcgtcttt tccctctcct      60
ccccacaccc gacagtcctc gacgaggtgt aggacggcga gcaaagctgc cgagggcgat     120
ctgggctgac tgagcgctcg agtgtacagt tatcggtctg agcagcgccc tcatcctcgc     180
tcggaagggc tacagcgtgc atattctcgc gcgcgacttg ccggaggacg tctcgagcca     240
gactttcgct tcaccatggg ctgtgcgtcg tctcactgta gttggaggat gtcagcgaga     300
gctgagcaat ctcgtcatcc ccgcagggcg cgaattggac gcctttcatg acgcttacag     360
acggtcctcg acaagcaaaa tgggaagaat cgactttgtg cgtctccttc tacctcattc     420
ttggcctcga gctgacgagt gtatgataca cagcaagaag tgggtcgagt tggtcccgac     480
gggccatgcc atgtggctca aggggacgag gcggttcgcg cagaacgaag acggcttgct     540
cgggcactgg tacaaggaca tcacgccaaa tgtgcgccca cattcactct tcccttcgca     600
tgtctccgtt tactgacccg ccctctttcg ccgtgcgcag taccgccccc tcccatcttc     660
cgaatgtcca cctggcgcta tcggcgtaac ctacgacacc ctctccgtcc acgcaccaaa     720
gtactgccag taccttgcaa gagagctgca gaagctcggc gcgacgtttg agagacggac     780
cgttacgtcg cttgagcagg cgttcgacgg tgcggatttg gtggtcaacg ctacgggact     840
tggtatgtcc gaactgcccc tctctacct gcaattttgc tgattgatat gctcgcaggc     900
gccaagtcga ttgcgggcat cgacgaccaa gccgccgagc caatccgcgg ccaaaccgtc     960
ctcgtcaagt cccatgcaa gcgatgcacg atggactcgt ccgaccccgc ttctcccgcc    1020
tacatcattc cccgaccagg tggcgaagtc atctgcggcg gacgtacgg cgtgggagac    1080 tgggacttgt ctgtcaaccc agagacggtc cagcggatcc tcaagcactg cttgcgcctc    1140
gacccgacca tctcgagcga cggaacgatc gaaggcatcg aggtcctccg ccacaacgtc    1200
ggcttgcgac ctgcacgacg aggcggaccc cgcgtcgagg cagaacggat cgtcctgcct    1260
ctcgaccgga caaagtcgcc cctctcgctc ggcaggggca gcgcacgagc ggcgaaggag    1320
aaggaggtca gcttgtgca tgcgtatggc ttctcgagtg cgggatacca gcagagttgg    1380
ggcgcggcgg aggatgtcgc gcagctcgtc gacgaggcgt ccagcggta ccacggcgcg    1440 gcgcgggagt cgaagttgta g                                             1461
```

<210> SEQ ID NO 12
<211> LENGTH: 368
<212> TYPE: PRT
<213> ORGANISM: Rhodosporidium toruloides MTCC 457

<400> SEQUENCE: 12

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Asn Trp Thr Pro Phe Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 13

```
<211> LENGTH: 1461
<212> TYPE: DNA
<213> ORGANISM: Rhodosporidium toruloides NP11

<400> SEQUENCE: 13
atgcactctc agaagcgcgt cgttgtcctc ggatcaggcg gtgcgtcttt tccctctcct      60
ccccacaccc gacagtcctc gacgaggtgt aggacggcga gcaaagctgc cgagggcgat     120
ctgggctgac tgagcgctcg agtgtacagt tatcggtctg agcagcgccc tcatcctcgc     180
tcggaagggc tacagcgtgc atattctcgc gcgcgacttg ccggaggacg tctcgagcca     240
gactttcgct tcaccatggg ctgtgcgtcg tctcactgta gttggaggat gtcagcgaga     300
gctgagcaat ctcgtcatcc cgcagggcg cgaattggac gcctttcatg acgcttacag      360
acggtcctcg acaagcaaaa tgggaagaat cgactttgtg cgtctccttc tacctcattc     420
ttggcctcga gctgacgagt gtatgataca cagcaagaag tgggtcgagt tggtcccgac     480
gggccatgcc atgtggctca aggggacgag gcggttcgcg cagaacgaag acggcttgct     540
cgggcactgg tacaaggaca tcacgccaaa tgtgcgccca cattcactct cccttcgca     600 tgtctccgtt tactgacccg ccctctttcg ccgtgcgcag taccgccccc tcccatcttc     660
cgaatgtcca cctggcgcta tcggcgtaac ctacgacacc ctctccgtcc acgcaccaaa     720
gtactgccag taccttgcaa gagagctgca gaagctcggc gcgacgtttg agagacggac     780
cgttacgtcg cttgagcagg cgttcgacgg tgcggattg gtggtcaacg ctacgggact      840
tggtatgtcc gaactgcccc tctctacct gcaattttgc tgattgatat gctcgcaggc       900
gccaagtcga ttgcgggcat cgacgaccaa gccgccgagc caatccgcgg ccaaaccgtc      960
ctcgtcaagt ccccatgcaa gcgatgcacg atggactcgt ccgaccccgc ttctcccgcc    1020
tacatcattc cccgaccagg tggcgaagtc atctgcggcg gacgtacgg cgtgggagac     1080 tgggacttgt ctgtcaaccc agagacggtc cagcgatcc tcaagcactg cttgcgcctc     1140
gacccgacca tctcgagcga cggaacgatc gaaggcatcg aggtcctccg ccacaacgtc    1200
ggcttgcgac ctgcacgacg aggcggaccc cgcgtcgagg cagaacggat cgtcctgcct    1260
ctcgaccgga caaagtcgcc cctctcgctc ggcaggggca gcgcacgagc ggcgaaggag    1320
aaggaggtca gcttgtgca tgcgtatggc ttctcgagtg cgggatacca gcagagttgg     1380
ggcgcggcgg aggatgtcgc gcagctcgtc gacgaggcgt tccagcggta ccacggcgcg    1440
gcgcgggagt cgaagttgta g                                              1461

<210> SEQ ID NO 14
<211> LENGTH: 368
<212> TYPE: PRT
<213> ORGANISM: Rhodosporidium toruloides NP11

<400> SEQUENCE: 14

Met His Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Asn Trp Thr Pro Phe Met Thr Leu Thr Asp Gly
        50                  55                  60

Pro Arg Gln Ala Lys Trp Glu Glu Ser Thr Phe Lys Lys Trp Val Glu
65                  70                  75                  80
```

```
Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Met Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 15
<211> LENGTH: 2092
<212> TYPE: DNA
<213> ORGANISM: Rhodotorula minuta

<400> SEQUENCE: 15
cgtctctcaa acaagttcaa acggaccgga agcgataacc tgcttttctt cttcataacc      60
acacattctg acaagcatga cgctaccact tctcgaagat gcacctcgag cattggacgc     120
cgtcattatc ggcgcaggcg tcactggcct cagtatcgga ctggagcttg taaaaagagg     180
ctacaagatt gcagtcgtag cgaaggactt gcctgaagat gatcagagtc ctggctttgc     240
aagtccatgg gctgtgagga gtcttttcct tcatctatcg ttccttttga catgcctact     300
gacgcactgg ctgtgacatt gcaggggtgc aactggtgct ctttcgcagg tatgccctc     360 caatcttccg aaagattagc ttcgcgggga cggcaaaaaa agatcctcgc aagatgtcat     420
aagctgaaga agcgcttccc ttcccccact ttccttagac aacaacaaga gagagcaaga     480
atgggatcgt aaaacatacc aagccctctt taacgtagct gaaaaccatc ccaacctatg     540
```

-continued

```
cgaggtgagc taggctttcg cttagagaga gagatcacgt ggtgtacaag gacgaagtgt      600
gaaggaaccg cttcaatata gtttatgata gctgactctc ttgcttttgg cttgactaca      660
gctcattcag ttccactcgt atgaaagcga caagttacct gaaccttggt tcaaagatct      720
cgtgaaagat gtaagctacc tgttttccg ctacttccta cgataaattg gggaatgcaa       780
ataagaacca ttccgcaaga cagtagttga cgaagctata acctctttac cctcgcgttc      840
tcaatgtcac ctttcacatt tctgaccacc catcagtaca aagtcacgaa ggagggcacg      900
aaaccaggcg aaagatgcat aagctacaaa tccttcatca tgcacgcgcc caattatcta      960
cgtcacctag cgcagcagct tcgctcagcg ggcgttccga tccagcggaa acgcctgaca     1020
tcgctcgaag aagcgtacaa cctcccttca tacggccgcg tcaatctagt gatcaacgct     1080
acgggtctag gtgctcgttc gttactgggc aataaggatc caagcgatat atatcccatc     1140
aggggacaga ctgtccttgt caaagtaccg cagggatgga agaaaacctg cttcatgatg     1200
gcgagcgacc atccggacga aagacgacg aaagatacgg aaatcccaga accgacttat      1260
attattccga gacctggtcc agagggacat gtagtactgt gagtgacgag cttcattctt     1320
aatattgtgc actcgaggaa gtctggtctt atgctggtct catcgtagag gaggttcatt     1380
ccaagtcaac aattgggaat atgcaccaga ctacgcatta gcggaacgca ttctgaagcg     1440
taactacgag ttgtgccctg aactggcagg tccaaatgga aaatcgtgga agacagtaa      1500
ggcttgattc ctatgtgaca gaattggtgt tacgtactga tagcactttta ctatttctac     1560
agttgaaatc gtagcccaca atgtcggatt cagacctagc cgacaaggag gatgcaggct     1620
tgatctcgag cctattgagc taggtaacgc taaacaagaa ggaatgcaac tcgctcccaa     1680
atcgacaatt accgaaccta ggactggagc tatattgcat gcctatggaa taggtgagcc     1740
acactcatct gcatcacagt gtggtaaaat gctccactta aatactgatg ttgcgcttcc     1800
tcttttgtgt atctctgata caaacgatga aataggcccg gccggattcc aagcttccct     1860
cggatacgct ctagaagctg gagatatggt cgactcatac ttcaagaagg gcgacgcgaa     1920
gaagcgaagt tcgaagctgt aaacacgaga aggaagggaa tggaagttaa ggagcacagg     1980
gcactcatac atcgtcaact atccaaagaa gatgcttgat acggaaggcg taacgaggaa     2040
tcaaaagaag ggaagttgac ctgaacttag tgaagcatat acttgttcaa ag             2092
```

<210> SEQ ID NO 16
<211> LENGTH: 394
<212> TYPE: PRT
<213> ORGANISM: Rhodotorula minuta

<400> SEQUENCE: 16

Met Thr Leu Pro Leu Leu Glu Asp Ala Pro Arg Ala Leu Asp Ala Val
1               5                   10                  15

Ile Ile Gly Ala Gly Val Thr Gly Leu Ser Ile Gly Leu Glu Leu Val
            20                  25                  30

Lys Arg Gly Tyr Lys Ile Ala Val Ala Lys Asp Leu Pro Glu Asp
        35                  40                  45

Asp Gln Ser Pro Gly Phe Ala Ser Pro Trp Ala Gly Cys Asn Trp Cys
    50                  55                  60

Ser Phe Ala Asp Asn Asn Lys Arg Glu Gln Glu Trp Asp Arg Lys Thr
65                  70                  75                  80

Tyr Gln Ala Leu Phe Asn Val Ala Glu Asn His Pro Asn Leu Cys Glu
                85                  90                  95

Leu Ile Gln Phe His Ser Tyr Glu Ser Asp Lys Leu Pro Glu Pro Trp
                100                 105                 110

Phe Lys Asp Leu Val Lys Asp Tyr Lys Val Thr Lys Glu Gly Thr Lys
            115                 120                 125

Pro Gly Glu Arg Cys Ile Ser Tyr Lys Ser Phe Ile Met His Ala Pro
        130                 135                 140

Asn Tyr Leu Arg His Leu Ala Gln Gln Leu Arg Ser Ala Gly Val Pro
145                 150                 155                 160

Ile Gln Arg Lys Arg Leu Thr Ser Leu Glu Glu Ala Tyr Asn Leu Pro
                165                 170                 175

Ser Tyr Gly Arg Val Asn Leu Val Ile Asn Ala Thr Gly Leu Gly Ala
            180                 185                 190

Arg Ser Leu Leu Gly Asn Lys Asp Pro Ser Asp Ile Tyr Pro Ile Arg
        195                 200                 205

Gly Gln Thr Val Leu Val Lys Val Pro Gln Gly Trp Lys Lys Thr Cys
210                 215                 220

Phe Met Met Ala Ser Asp His Pro Asp Glu Lys Thr Thr Lys Asp Thr
225                 230                 235                 240

Glu Ile Pro Glu Pro Thr Tyr Ile Ile Pro Arg Pro Gly Pro Glu Gly
                245                 250                 255

His Val Leu Gly Gly Ser Phe Gln Val Asn Asn Trp Glu Tyr Ala
            260                 265                 270

Pro Asp Tyr Ala Leu Ala Glu Arg Ile Leu Lys Arg Asn Tyr Glu Leu
        275                 280                 285

Cys Pro Glu Leu Ala Gly Pro Asn Gly Lys Ser Trp Lys Asp Ile Glu
290                 295                 300

Ile Val Ala His Asn Val Gly Phe Arg Pro Ser Arg Gln Gly Gly Cys
305                 310                 315                 320

Arg Leu Asp Leu Glu Pro Ile Glu Leu Gly Asn Ala Lys Gln Glu Gly
                325                 330                 335

Met Gln Leu Ala Pro Lys Ser Thr Ile Thr Glu Pro Arg Thr Gly Ala
        340                 345                 350

Ile Leu His Ala Tyr Gly Ile Gly Pro Ala Gly Phe Gln Ala Ser Leu
        355                 360                 365

Gly Tyr Ala Leu Glu Ala Gly Asp Met Val Asp Ser Tyr Phe Lys Lys
    370                 375                 380

Gly Asp Ala Lys Lys Arg Ser Ser Lys Leu
385                 390

<210> SEQ ID NO 17
<211> LENGTH: 1749
<212> TYPE: DNA
<213> ORGANISM: Sporobolomyces roseus

<400> SEQUENCE: 17
atgccgacgc gtgagcctca gagagtagtc gtactaggcg caggaggtat gtagcaacgg    60
atttccactt cggctactcc cgaggttttc ctcccccact tgttttagcc gccaaccgac   120
ctctccttat ctcgcgctgc actctgctga tgcactcgag ggaactcgga cagtcatcgg   180
attaacttgc gcccttcac tcgtcgaaca aggctacacg gttcacgttg tcgcaagaga    240
ccttccggaa gacaccgact ctaccgcgtt cgcttctccc tgggccggcg ccaacgtatg   300
tccattcaag agtctcgagg aaggtccgag agaagcgaga tgggaaaccg tcactttgtc   360
agttgttact tgcctctcct ctcccccgag tcgacccgaa ctctctcatt cgacttttg    420

```
cactttccca cttttctagc aaaaaacttt caaccatgat cccatctggc ttggccatga    480
ctctcaaagg tactcggagg ttcgcacacg aagaatccca gttgttgggc cactggtaca    540
aagacgtcgt tccgaacgtg agcttttctt ccttcttttc ttcccccccga cctcgtaact   600
ccgtctcctc tctgagctcg agtctcgctc gaagcaaatt acttcgtgtg ttctgatctc    660
cgctttgtgt gagttgatta gtaccgacac ttgaatcgcg aagaatgtcc acccaatgcg    720
atcggagtcg aattcgatac catctcggtc aacgcaccga atattgtca ctacctcgct     780
cacgagttga ggtcaaaggg agtcacgatc gagaggaggt acgtcaagtc tattgaagag    840
gttttccgag aaacgtttgg agcgagaaac gatttcgtcg tcaatgcgac tggattaggt    900
actattttcc ctttcccgac tctctctctc tctctctctg tctgtctttc ctcataccga    960
actcgttgta ttgactgatt tgctcgtggt tataggagca aaaagtatcg caggagtaga    1020
agatcaagaa gtgagaccga ttcgaggtca aaccgtcttg atcaaatcgg attgcgttcg    1080
gtgtacgatg gattcgagtg gttgagttct ttgtctttct ccctataccc ctttccccga   1140
accttgagtg ttgcattcaa tcgctaaata acgttcttgt gtgcgggttt tcttctttct    1200
tcagatccaa cctcttccgc ttacatcatc cctcgacctg gaggtgaagt catttgcggt    1260
ggctcttacg gtgtacgtct gttacgtttt ccctctatct ctcccgagga atcaaagtcc    1320
caaactcatt ttttttcttt ctcttttgg gtctcttctg ttcgtcgaca ggtggacgac     1380
tgggacttgt cggtttctcc cgatcatgcg aaacgtatac tctctcactg tctacgacta    1440
gaccttcga tctctcgaga tggtacccctc gaaggcatcg aaatcttgag gcacaacgtc    1500
gggctgagac cttctaggag ttctggaccg agagtcgaaa aggaaatcat cgagctgaac    1560
cacgaaaaga gtccgattcg gatcgggtct cgtctcgacg atgcgaccaa ggggaagagt    1620
gcgaagacac gtggagtggt ggtacacgct tacggagtgg gaccggcggg ataccagcag    1680
agttggggaa tcgcacaaga cgtcgtcaag ttgatacaag aaggagaagc acgagaatcc    1740
aagttgtag                                                           1749
```

<210> SEQ ID NO 18
<211> LENGTH: 371
<212> TYPE: PRT
<213> ORGANISM: Sporobolomyces roseus

<400> SEQUENCE: 18

Met Pro Thr Arg Glu Pro Gln Arg Val Val Leu Gly Ala Gly Val
1               5                   10                  15

Ile Gly Leu Thr Cys Ala Leu Ser Leu Val Glu Gln Gly Tyr Thr Val
            20                  25                  30

His Val Val Ala Arg Asp Leu Pro Glu Asp Thr Asp Ser Thr Ala Phe
        35                  40                  45

Ala Ser Pro Trp Ala Gly Ala Asn Val Cys Pro Phe Lys Ser Leu Glu
    50                  55                  60

Glu Gly Pro Arg Glu Ala Arg Trp Glu Thr Val Thr Phe Lys Lys Leu
65                  70                  75                  80

Ser Thr Met Ile Pro Ser Gly Leu Ala Met Thr Leu Lys Gly Thr Arg
                85                  90                  95

Arg Phe Ala His Glu Glu Ser Gln Leu Leu Gly His Trp Tyr Lys Asp
            100                 105                 110

Val Val Pro Asn Tyr Arg His Leu Asn Arg Glu Glu Cys Pro Pro Asn
        115                 120                 125

Ala Ile Gly Val Glu Phe Asp Thr Ile Ser Val Asn Ala Pro Lys Tyr

```
            130                 135                 140
Cys His Tyr Leu Ala His Glu Leu Arg Ser Lys Gly Val Thr Ile Glu
145                 150                 155                 160

Arg Arg Tyr Val Lys Ser Ile Glu Glu Val Phe Arg Glu Thr Phe Gly
                165                 170                 175

Ala Arg Asn Asp Phe Val Val Asn Ala Thr Gly Leu Gly Ala Lys Ser
            180                 185                 190

Ile Ala Gly Val Glu Asp Gln Glu Val Arg Pro Ile Arg Gly Gln Thr
        195                 200                 205

Val Leu Ile Lys Ser Asp Cys Val Arg Cys Thr Met Asp Ser Ser Asp
    210                 215                 220

Pro Thr Ser Ser Ala Tyr Ile Ile Pro Arg Pro Gly Gly Glu Val Ile
225                 230                 235                 240

Cys Gly Gly Ser Tyr Gly Val Asp Asp Trp Asp Leu Ser Val Ser Pro
                245                 250                 255

Asp His Ala Lys Arg Ile Leu Ser His Cys Leu Arg Leu Asp Pro Ser
            260                 265                 270

Ile Ser Arg Asp Gly Thr Leu Glu Gly Ile Glu Ile Leu Arg His Asn
        275                 280                 285

Val Gly Leu Arg Pro Ser Arg Ser Ser Gly Pro Arg Val Glu Lys Glu
    290                 295                 300

Ile Ile Glu Leu Asn His Glu Lys Ser Pro Ile Arg Ile Gly Ser Arg
305                 310                 315                 320

Leu Asp Asp Ala Thr Lys Gly Lys Ser Ala Lys Thr Arg Gly Val Val
                325                 330                 335

Val His Ala Tyr Gly Val Gly Pro Ala Gly Tyr Gln Gln Ser Trp Gly
            340                 345                 350

Ile Ala Gln Asp Val Val Lys Leu Ile Gln Glu Gly Glu Ala Arg Glu
        355                 360                 365

Ser Lys Leu
    370

<210> SEQ ID NO 19
<211> LENGTH: 1474
<212> TYPE: DNA
<213> ORGANISM: Sporobolomyces linderae

<400> SEQUENCE: 19
tctttcacac ttgtccacgc ggcccaagct tgtctgcgcg gcaacccgag cgcgcgagcg      60
cgcgagcgac gtttccgagt caccccctct ccgcccgctc tcccagcagc atggctcctg     120
ctgcctctcc acgtgtgctc gtcatcggag ccggcgcgtc gcccgcgctc gcgcgcgctc     180
gactgacttg gcaggcgtcg tgggcctaac gacggccgtg gagatccagc gcgctctgcc     240
tgagggtgcg cagtcgctgc gctgcccgag ctgaggcctc agccgccgtg accatcttcg     300
cggcgcagac agccgaggat ctcaagtcga cgcgctacac cagctcgtgg gccggcgcgc     360
atcacgtcac gctggagggc cccggtctgc agcgcgactg cgaggtggac acgttcaagg     420
cgctctgggc gctcgcgcac gacgatccga gcgtgccgtt gctcgtgtgc ccacagaccg     480
aggtgctgtc tgaccgccgc gcccgcttgc tcgctccagc gatcggctga gcgagctgta     540
cgcctcggca tgagccagct gacgccgatc aggtcttcga ggatgcgtcc aaggccgact     600
tcatgcgcaa gaatctcagc tcgttcatgc ccgacgtcaa gccgctcgaa ccttcagcgc     660
tgcccgaagg ctgcacagcg gggctgtcgt tcacgaccat cgcgctcgac acgccaaact     720
```

```
atctgccatg gctcgcgcag cgattccgcg cggccggcgg gaccgtcgtc cgtcgcgagc    780
tcggcaagct gagtgacgcg ccgctcgacg agttcgacgc cgtcgtcaac tgctcgggcc    840
taggcgcgct cacgctcgtc ggcgacgaca gcatgtaccc gatccgcggc cagaccgtgc    900
tcgtccgcgc gccgtggatc cgttccggca tcacgcgatc cggcagcgac aactggagtg    960
cgttgccgtt tcgttgtcga gctgatcgcg cagcatacat cattccgcgc aagcagggcg   1020
acgtgattgt tggcgggaca cgcggcatcg acgactggtc cgtcggcgcg cctggccaga   1080
ctgacgctgc aggcacgagc agcctcgacc cgaaacggcg tcggagatcc tcgcgcgcgg   1140
cctcaagctg tgccctgcgc tgctgcccga ggcgaagcgg gcgtcaatgc gcgtcgagga   1200
catcgacgtc gtggagcacg gctggtccgt tccgcttcgt cggccgcgct gacctcgcag   1260
cggcttccga ccggcgcgca aaggcggcgt ccgcatcgag ctcgaccacg tcgcggcgcc   1320
cgacggtcgg tcactgccgc tcgtgcacaa ctacggccac gctggcgccg gcttccagat   1380
gtcgatcggc tcggcgactc gcgctgtgga tctgctgcgg tctgcgctcg cgtcctgatt   1440
gtgcatgacg cgtcatgcac agggttgtct cgtc                               1474
```

<210> SEQ ID NO 20
<211> LENGTH: 343
<212> TYPE: PRT
<213> ORGANISM: Sporobolomyces linderae

<400> SEQUENCE: 20

```
Met Ala Pro Ala Ala Ser Pro Arg Val Leu Val Ile Gly Ala Gly Val
1               5                   10                  15

Val Gly Leu Thr Thr Ala Val Glu Ile Gln Arg Ala Leu Pro Glu Ala
            20                  25                  30

Ala Val Thr Ile Phe Ala Ala Gln Thr Ala Glu Asp Leu Lys Ser Thr
        35                  40                  45

Arg Tyr Thr Ser Ser Trp Ala Gly Ala His His Val Thr Leu Glu Gly
    50                  55                  60

Pro Gly Leu Gln Arg Asp Cys Glu Val Asp Thr Phe Lys Ala Leu Trp
65                  70                  75                  80

Ala Leu Ala His Asp Pro Ser Val Pro Leu Val Cys Pro Gln
                85                  90                  95

Thr Glu Val Phe Glu Asp Ala Ser Lys Ala Asp Phe Met Arg Lys Asn
            100                 105                 110

Leu Ser Ser Phe Met Pro Asp Val Lys Pro Leu Glu Pro Ser Ala Leu
        115                 120                 125

Pro Glu Gly Cys Thr Ala Gly Leu Ser Phe Thr Thr Ile Ala Leu Asp
    130                 135                 140

Thr Pro Asn Tyr Leu Pro Trp Leu Ala Gln Arg Phe Arg Ala Ala Gly
145                 150                 155                 160

Gly Thr Val Val Arg Arg Glu Leu Gly Lys Leu Ser Asp Ala Pro Leu
                165                 170                 175

Asp Glu Phe Asp Ala Val Val Asn Cys Ser Gly Leu Gly Ala Leu Thr
            180                 185                 190

Leu Val Gly Asp Asp Ser Met Tyr Pro Ile Arg Gly Gln Thr Val Leu
        195                 200                 205

Val Arg Ala Pro Trp Ile Arg Ser Gly Ile Thr Arg Ser Gly Ser Asp
    210                 215                 220

Asn Trp Thr Tyr Ile Ile Pro Arg Lys Gln Gly Asp Val Ile Val Gly
225                 230                 235                 240
```

-continued

```
Gly Thr Arg Gly Ile Asp Asp Trp His Glu Gln Pro Arg Pro Glu Thr
                245                 250                 255

Ala Ser Glu Ile Leu Ala Arg Gly Leu Lys Leu Cys Pro Ala Leu Leu
            260                 265                 270

Pro Glu Ala Lys Arg Ala Ser Met Arg Val Glu Asp Ile Asp Val Val
        275                 280                 285

Glu His Gly Cys Gly Phe Arg Pro Ala Arg Lys Gly Gly Val Arg Ile
    290                 295                 300

Glu Leu Asp His Val Ala Ala Pro Asp Gly Arg Ser Leu Pro Leu Val
305                 310                 315                 320

His Asn Tyr Gly His Ala Gly Ala Gly Phe Gln Met Ser Ile Gly Ser
                325                 330                 335

Ala Thr Arg Ala Val Asp Leu
            340

<210> SEQ ID NO 21
<211> LENGTH: 2157
<212> TYPE: DNA
<213> ORGANISM: Puccinia triticina

<400> SEQUENCE: 21
atggatggat gcactccatg gtttgatttg aaagacatgt ttgtaatata ccttgtctcc      60
gaggaggttt ccccgctcct gctgtgcaat caggtgcctt tatgtatttt gaggaccatc     120
attcctggtc tcaagccatt cagttaacat ctcatcaagt gcccaccccc aaggacatat     180
tatcgcccca cgaatctggt ccttcaatcc tcgagttgct agtgatctct ggtcatgtcc     240
gccccaccga gccaagagcc gccgtgcatt gtcaacgtca tcggatccgg tgtactcggt     300
ctcacctgtg cactcgagct cgccaaacag ccgggctcac catatcgtgt caatgtggtc     360
accgccgaaa gcgcgctgac tgcatggtct caagacccgt cgacgaagct cccggtggaa     420
ccagattttg cttccccttg ggcggtacgt gtttcaaatg agacacattt ctttcattca     480
ttttcattca tttggcagag aaaaaaaaat tatgagccgg aggaagaagt gacttgacct     540
cttttctgat tgcgcatgta gggtgctttc tggcacccct tcactcctca accagagacc     600
gagctgcaga aaagggtagc cggatgggag acgaagtcgt ttaagcatct ttgggagatt     660
gctgagcaag atccttcggt tgtcatggtt agcggctcag acggctcaag ccctccccat     720
ccacaccctc caagatctgc tgaaaacctt cgtttctcgg gggctattgt agaaagctga     780
cttcaagaaa tattatgacc atcggttgac tgaattaccg tggtatatgg acctatgtcc     840
ggaggtgaat tatccgttgg tttatatctg gacactccaa tctttccaat tgagtaaact     900
gacttgagag cgcacgtgat tgaaaggctc gaaaaatgaa cgacgaagaa ttagcgaagg     960
cgccagaagg aaaagtagat ggaataatct gtaaatccgt ttccttgaac ccaatccgtt    1020
acctggatta cctcagaaag caactggtca aatacgaagt ccaaatcatt caccatcgtc    1080
ttgaaaccgt ctcggaggct ttctgggggg atcccaagtt tggcatcccg gcggcgaaaa    1140
tagtagtaaa tgcgtcaggt ctcggcgcgg gcagcttgtg tggtgtgtca gacgaattga    1200
tggagccgat tcgtggtcaa acgatcctca tcaggccccc tcaaccgatc caactaatca    1260
cacgggatga cgataaatgt atctacatct gctcgcgccc acctaccata cccggcgaag    1320
gcgaagaggt catcttgggt ggctcatatg aacctggcaa ctcctcttta tccatcgaca    1380
acggaatcgc cgataggatc ttgaccgaag cgctcaagct ccggcccgat cttagccgtg    1440
acggcacgtc caacggcatc gaaatattgg atcatattgc ggctttgagg cccagtcgca    1500
```

-continued

```
aggatggtcc tcgggttgaa agggaaaatt tcacgatttc taagaaagga gaaactcagg    1560
atgaaactgg ctcttggtc cattgttatg gaattgggta aatttcttcc ctcgttgtcc    1620
taacctggta attccttagc aaaccggtgg ctcaaattta cttccgtatt acactttttg    1680
cattgatcag aggaggaggc tttcaggtgc gtgaatgaag gcatttgatt tctgcctgag    1740
cgtaaagtga agagcatctc atcggtgatg attttttctt gcttcccgtg cacgtgaaag    1800
gcgagctacg gggcagcggc agaagttaga agcttgatag agactcagaa aaacatctct    1860
tgatcggtga cttgtctgga ggatttcatt caggtaaaac ttgatgtgtt gattggtcta    1920
tcagattgac ctcattaacc tcaattttag ttgttgcaga catgaaactc cacctcatta    1980
aaacatccgg gaatcaagta cagaacaagt attttaacag ttttgtttt cgtattagca    2040 cggaaatggg tgtgtttgct tgatgttgag aagtatcttt actaagcatg tcatgagagt    2100
taaatctaaa ttttccaagt acaagaaaaa aatgatagag attgcgttca atgtggt       2157
```

<210> SEQ ID NO 22
<211> LENGTH: 385
<212> TYPE: PRT
<213> ORGANISM: Puccinia triticina

<400> SEQUENCE: 22

```
Met Ser Ala Pro Pro Ser Gln Glu Pro Pro Cys Ile Val Asn Val Ile
1               5                   10                  15

Gly Ser Gly Val Leu Gly Leu Thr Cys Ala Leu Glu Leu Ala Lys Gln
            20                  25                  30

Pro Gly Ser Pro Tyr Arg Val Asn Val Val Thr Ala Glu Ser Ala Leu
        35                  40                  45

Thr Ala Trp Ser Gln Asp Pro Ser Thr Lys Leu Pro Val Glu Pro Asp
    50                  55                  60

Phe Ala Ser Pro Trp Ala Gly Ala Phe Trp His Pro Phe Thr Pro Gln
65                  70                  75                  80

Pro Glu Thr Glu Leu Gln Lys Arg Val Ala Gly Trp Glu Thr Lys Ser
                85                  90                  95

Phe Lys His Leu Trp Glu Ile Ala Glu Gln Asp Pro Ser Val Val Met
            100                 105                 110

Lys Ala Asp Phe Lys Lys Tyr Tyr Asp His Arg Leu Thr Glu Leu Pro
        115                 120                 125

Trp Tyr Met Asp Leu Cys Pro Glu Ala Arg Lys Met Asn Asp Glu Glu
    130                 135                 140

Leu Ala Lys Ala Pro Glu Gly Lys Val Asp Gly Ile Ile Cys Lys Ser
145                 150                 155                 160

Val Ser Leu Asn Pro Ile Arg Tyr Leu Asp Tyr Leu Arg Lys Gln Leu
                165                 170                 175

Val Lys Tyr Glu Val Gln Ile Ile His His Arg Leu Glu Thr Val Ser
            180                 185                 190

Glu Ala Phe Leu Gly Asp Pro Lys Phe Gly Ile Pro Ala Ala Lys Ile
        195                 200                 205

Val Val Asn Ala Ser Gly Leu Gly Ala Gly Ser Leu Cys Gly Val Ser
    210                 215                 220

Asp Glu Leu Met Glu Pro Ile Arg Gly Gln Thr Ile Leu Ile Arg Pro
225                 230                 235                 240

Pro Gln Pro Ile Gln Leu Ile Thr Arg Asp Asp Lys Cys Ile Tyr
                245                 250                 255

Ile Cys Ser Arg Pro Pro Thr Ile Pro Gly Glu Gly Glu Glu Val Ile
```

```
              260                 265                 270
Leu Gly Gly Ser Tyr Glu Pro Gly Asn Ser Ser Leu Ser Ile Asp Asn
            275                 280                 285

Gly Ile Ala Asp Arg Ile Leu Thr Glu Ala Leu Lys Leu Arg Pro Asp
        290                 295                 300

Leu Ser Arg Asp Gly Thr Ser Asn Gly Ile Glu Ile Leu Asp His Ile
305                 310                 315                 320

Ala Ala Leu Arg Pro Ser Arg Lys Asp Gly Pro Arg Val Glu Arg Glu
                325                 330                 335

Asn Phe Thr Ile Ser Lys Lys Gly Glu Thr Gln Asp Glu Thr Gly Leu
            340                 345                 350

Leu Val His Cys Tyr Gly Ile Gly Gly Gly Phe Gln Ala Ser Tyr
        355                 360                 365

Gly Ala Ala Ala Glu Val Arg Ser Leu Ile Glu Thr Gln Lys Asn Ile
    370                 375                 380

Ser
385

<210> SEQ ID NO 23
<211> LENGTH: 1602
<212> TYPE: DNA
<213> ORGANISM: Puccinia graminis

<400> SEQUENCE: 23
```

| | | | | | |
|---|---|---|---|---|---|
| atgtccaatg | tcaacgtcat | cggatccggt | gttcttggcc | tcacctgtgc | tctcgagctc | 60 |
| gccaaacagc | ccggatcacc | ataccgtgtc | actgtggtga | ccgccgaaaa | cgctatggct | 120 |
| agatggtctc | aagacccgtc | cacgaagctt | ccagtggagc | ccgattttgc | ttctccttgg | 180 |
| gcggtatgtc | ataaatagac | tttcggttca | tcagtttgaa | tggaaaaaat | gaaaagtgat | 240 |
| gaacagggta | agaaagaac | catttttctga | tctcgggatg | ttctctaaat | ttagggcgct | 300 |
| ttcttccacc | ccttcactcc | acaacccgag | accgagctac | agaaaagggt | ggcctcatgg | 360 |
| gagaggaagt | cgtttaagcc | tctttgggag | atcgctgagc | aagatccttc | ggtcgtcatg | 420 |
| gtcagcggtc | tcagacggct | aaaactctct | atcttcatcc | tccatcaaca | cgtgctgagg | 480 |
| ttcttcatct | ctcggtggct | actagaaaac | cgacttcaaa | agtattaca | accatccgtt | 540 |
| gtccgaatta | ccgtggtata | tggatctgtt | cccagaggtg | aagaaatcat | ggatgcgct | 600 |
| agattctctc | tctacgcaag | tgaactgact | tgaggctaaa | cattttcact | ggaaggctcg | 660 |
| aaaaatgaac | gccgaagaaa | tagcgaatgg | acccgaagga | aaagtcgacg | gcctgatctg | 720 |
| caaatcggtg | accctgaacc | cgatccggta | cctagattac | cttcgacaac | aactagccaa | 780 |
| atatgacgtc | cgcatcattc | accatcgtct | cgagaccgtc | actgaggctt | ttgagggcca | 840 |
| tcccgagtgc | ggtctaccgg | cggcaaagat | agtgatcaat | gcgtgtggtc | taggcgcggg | 900 |
| caagataggg | ggcgtgtcgg | acggaatgat | ggagccgatt | cgcggccaga | ccatgctcat | 960 |
| ccgcccccct | caaccgctcc | aactgatcac | acgggacgac | gagaaatgta | tctacatctg | 1020 |
| ttcccgtcca | cccacgatcc | cgggagaagg | cgaagaggtc | gtcctgggag | gctcttatca | 1080 |
| acctggcgac | tcctcattgg | agatcgatga | ccaaatctct | cataggatct | tgtccgaggc | 1140 |
| actcaaaatc | aggcccgatc | tcagccatga | cggcacggtt | gaaggcgtcc | aaatagtgga | 1200 |
| acatgtcgcg | gctctgagac | ctcataataa | gaatggccct | cgtgtcgaac | gtgaagattt | 1260 |
| ccacattaaa | tctactagtc | aaggagagac | tcagaattca | actgggatat | tggtccattg | 1320 |
| ttatggaatc | gggttagtct | tctatcgtct | catccttcct | cttcaatcaa | attgatgaat | 1380 |

```
taaaattgac tctcttcctg ctcacaatct ttgtatcgag caggggagga ggattccaag    1440
tgagtgaatc aaaaaaagac cgtgttcctt cttgtgacct ctgtttgaac ttgggattag    1500
ctcttctttg ctgacatatt cctggttatt ttgtttgttt gaaaggcaag ctatggggtt    1560
gcagaagaag tgagaaatct agtagaacaa ggccggtctt ga                      1602
```

<210> SEQ ID NO 24
<211> LENGTH: 376
<212> TYPE: PRT
<213> ORGANISM: Puccinia graminis

<400> SEQUENCE: 24

```
Met Ser Asn Val Asn Val Ile Gly Ser Gly Val Gly Leu Thr Cys
1               5                   10                  15

Ala Leu Glu Leu Ala Lys Gln Pro Gly Ser Pro Tyr Arg Val Thr Val
            20                  25                  30

Val Thr Ala Glu Asn Ala Met Ala Arg Trp Ser Gln Asp Pro Ser Thr
        35                  40                  45

Lys Leu Pro Val Glu Pro Asp Phe Ala Ser Pro Trp Ala Gly Ala Phe
    50                  55                  60

Phe His Pro Phe Thr Pro Gln Pro Glu Thr Glu Leu Gln Lys Arg Val
65                  70                  75                  80

Ala Ser Trp Glu Arg Lys Ser Phe Lys Pro Leu Trp Glu Ile Ala Glu
                85                  90                  95

Gln Asp Pro Ser Val Val Met Lys Thr Asp Phe Lys Lys Tyr Tyr Asn
            100                 105                 110

His Pro Leu Ser Glu Leu Pro Trp Tyr Met Asp Leu Phe Pro Glu Ala
        115                 120                 125

Arg Lys Met Asn Ala Glu Glu Ile Ala Asn Gly Pro Glu Gly Lys Val
    130                 135                 140

Asp Gly Leu Ile Cys Lys Ser Val Thr Leu Asn Pro Ile Arg Tyr Leu
145                 150                 155                 160

Asp Tyr Leu Arg Gln Gln Leu Ala Lys Tyr Asp Val Arg Ile Ile His
                165                 170                 175

His Arg Leu Glu Thr Val Thr Glu Ala Phe Glu Gly His Pro Glu Cys
            180                 185                 190

Gly Leu Pro Ala Ala Lys Ile Val Ile Asn Ala Cys Gly Leu Gly Ala
        195                 200                 205

Gly Lys Ile Gly Gly Val Ser Asp Gly Met Met Glu Pro Ile Arg Gly
    210                 215                 220

Gln Thr Met Leu Ile Arg Pro Pro Gln Pro Leu Gln Leu Ile Thr Arg
225                 230                 235                 240

Asp Asp Glu Lys Cys Ile Tyr Ile Cys Ser Arg Pro Pro Thr Ile Pro
                245                 250                 255

Gly Glu Gly Glu Val Val Leu Gly Gly Ser Tyr Gln Pro Gly Asp
            260                 265                 270

Ser Ser Leu Glu Ile Asp Asp Gln Ile Ser His Arg Ile Leu Ser Glu
        275                 280                 285

Ala Leu Lys Ile Arg Pro Asp Leu Ser His Asp Gly Thr Val Glu Gly
    290                 295                 300

Val Gln Ile Val Glu His Val Ala Ala Leu Arg Pro His Asn Lys Asn
305                 310                 315                 320

Gly Pro Arg Val Glu Arg Glu Asp Phe His Ile Lys Ser Thr Ser Gln
                325                 330                 335
```

Gly Glu Thr Gln Asn Ser Thr Gly Ile Leu Val His Cys Tyr Gly Ile
            340                 345                 350

Gly Gly Gly Gly Phe Gln Ala Ser Tyr Gly Val Ala Glu Glu Val Arg
        355                 360                 365

Asn Leu Val Glu Gln Gly Arg Ser
    370                 375

<210> SEQ ID NO 25
<211> LENGTH: 1585
<212> TYPE: DNA
<213> ORGANISM: Melampsora laricis-populina

<400> SEQUENCE: 25
atgagcttca atccagagca taagagcgag cacttgaata tcatcggttc aggagtcctc 60
ggtctcactt gcgctctaga aatagcgaaa gaaaaaggac gttacactat aaccatcatc 120
actgcggatg ccgattcatc cacttggtca ccatcggctc caccaaaaat tgagaaagtc 180
gccgaggact ttgcttcacc ttgggcagtt gagtaaacct catcgaacca aaatctgtac 240
tcctgcctaa ctttcgttca agttttgcct tgaactttca agggcgcata ttggcaatca 300
tttgtagcga ctagagatcc taagacgttc aacgaaaaaa gattacaaga ttgggagaaa 360
acttccttca aagaattatg gaaaatctca gagacggaca aatcaattgt gatggtgaaa 420
tatttgattc ttggagttct cagcccaagg gatgtgttcg ttgaaacatc tcaacactat 480
tccagcaaac cgattgtcac gaatattttg atgaagaact tagtgaccat gagttacctt 540
ggtacaccga tttgtgtcca gaggttggct aaagtctttg cgattcaatt atgccaggta 600
aacaaaaagc taatggccac taccctcaat ccccaaccac aagtttcgac gactaacctc 660
atcagagctt gcaagtctgc cccgccccccg acaagcaggg atttcattca agacgatctc 720
actcaatccg atgatgtatc taacttttct gcatactcaa ttatccaaga tgggcgttcg 780
aatcgttcac catcgcttga actcgcttgc ggaagccttc gaaggcaata acactcttca 840
aattccgcgc gctgacatcg tcatcaatgc gtcaggtcta ggggctgcta ccttacttgg 900
tgtagaagac aaatctgtac atcccattcg tggccagcta gttctagtca aaccacctca 960
gccaatatgt ttctcgacaa gagattcttc aaggaagact tacatcatct ctcgtccttc 1020
cgttgacccg gagattgacg aggaagtaat actaggaggg tgctaccagg ctgataattt 1080
tgacctttca gttgaccccg atctgactaa tcacattctg tgtgaggctt tccagacacg 1140
gccagaccta agtagtgatg gtaccctaca gggaatacat gtattgaaag aggttgtagc 1200
gcttagacct gctagaaagg atggagctcg acttgaggta gagaaagtcg tcatttctgg 1260
ggaaaacaag catgctgtac attgctatgg aattgggtac gtcccttgtc tatttagtgg 1320
tcaaggcttc catacacttt ctatgcatcc cttcaagtga attactgctg agccatgtct 1380
tgatcgcttc ttacagtggt gctgggtttc aggtaagaga tgtccctctc tttcatggcc 1440
cttttgtcct ccgaatttac catatttttt ctgcttgtgg gtgcgaaaca attgccactc 1500
atttttcctt cagtcaagtt atggtatggc acaggaagca ttgggattga ttaaggcact 1560
tcgagagggt cgggaaactg tttaa 1585

<210> SEQ ID NO 26
<211> LENGTH: 378
<212> TYPE: PRT
<213> ORGANISM: Melampsora laricis-populina

<400> SEQUENCE: 26

Met Ser Phe Asn Pro Glu His Lys Ser Glu His Leu Asn Ile Ile Gly
1               5                   10                  15

Ser Gly Val Leu Gly Leu Thr Cys Ala Leu Glu Ile Ala Lys Glu Lys
            20                  25                  30

Gly Arg Tyr Thr Ile Thr Ile Ile Thr Ala Asp Ala Asp Ser Ser Thr
        35                  40                  45

Trp Ser Pro Ser Ala Pro Pro Lys Ile Glu Lys Val Ala Glu Asp Phe
    50                  55                  60

Ala Ser Pro Trp Ala Gly Ala Tyr Trp Gln Ser Phe Val Ala Thr Arg
65                  70                  75                  80

Asp Pro Lys Thr Phe Asn Glu Lys Arg Leu Gln Asp Trp Glu Lys Thr
                85                  90                  95

Ser Phe Lys Glu Leu Trp Lys Ile Ser Glu Thr Asp Lys Ser Ile Val
            100                 105                 110

Met Val Lys Tyr Leu Ile Leu Gly Val Leu Ser Pro Arg Asp Val Phe
        115                 120                 125

Val Glu Thr Ser Gln His Tyr Ser Ser Lys Pro Ile Val Thr Asn Ile
130                 135                 140

Leu Met Lys Asn Leu Val Thr Met Ser Tyr Leu Gly Thr Pro Ile Cys
145                 150                 155                 160

Val Gln Arg Leu Ala Lys Val Phe Ala Ile Gln Leu Cys Gln Met Gly
                165                 170                 175

Val Arg Ile Val His His Arg Leu Asn Ser Leu Ala Glu Ala Phe Glu
            180                 185                 190

Gly Asn Asn Thr Leu Gln Ile Pro Arg Ala Asp Ile Val Ile Asn Ala
        195                 200                 205

Ser Gly Leu Gly Ala Ala Thr Leu Leu Gly Val Glu Asp Lys Ser Val
210                 215                 220

His Pro Ile Arg Gly Gln Leu Val Leu Val Lys Pro Pro Gln Pro Ile
225                 230                 235                 240

Cys Phe Ser Thr Arg Asp Ser Ser Arg Lys Thr Tyr Ile Ile Ser Arg
                245                 250                 255

Pro Ser Val Asp Pro Glu Ile Asp Glu Glu Val Ile Leu Gly Gly Cys
            260                 265                 270

Tyr Gln Ala Asp Asn Phe Asp Leu Ser Val Asp Pro Asp Leu Thr Asn
        275                 280                 285

His Ile Leu Cys Glu Ala Phe Gln Thr Arg Pro Asp Leu Ser Ser Asp
290                 295                 300

Gly Thr Leu Gln Gly Ile His Val Leu Lys Glu Val Val Ala Leu Arg
305                 310                 315                 320

Pro Ala Arg Lys Asp Gly Ala Arg Leu Glu Val Glu Lys Val Val Ile
                325                 330                 335

Ser Gly Glu Asn Lys His Ala Val His Cys Tyr Gly Ile Gly Gly Ala
            340                 345                 350

Gly Phe Gln Ser Ser Tyr Gly Met Ala Gln Glu Ala Leu Gly Leu Ile
        355                 360                 365

Lys Ala Leu Arg Glu Gly Arg Glu Thr Val
    370                 375

<210> SEQ ID NO 27
<211> LENGTH: 1098
<212> TYPE: DNA
<213> ORGANISM: Ustilago maydis 521

<400> SEQUENCE: 27

```
atgacaaatc aacttcacgt agtggtcctc ggcgctggag tgcttggact gaccgatgcc    60
tttgagctgc gcgaacgcgg ctacagagtg accatcctcg cacgcgatct acctttcgac   120
tctttctccc agaccttcgc cagtccttgg gctggagcca actggtgttc cttcgctact   180
ctcgacgaca agccagcaca gcgtcgagac gaaatcacgt ttaagaaatg gctcaagctt   240
cacacgcgtt taccagagga agtaatggca ataatggagt ttaccgatat cggcctcacc   300
aagcgagata ccaaggatgt atggttcagc aacctgactc ctgaattcag cgtcctgcca   360
gacgccgatg aaatgggagc gcatgcaatc aagtacaaat cttttactat tagcgtaccg   420
ctgtacacgc gctggttggt gtcggagttg acttcgacca agcccattct ccttgatgct   480
acgcgagccg gtccgccagt agaaatccga cgatgctcca cgctaaccag cttatccgct   540
gtacgatcac tcgtaccagg ctgcgatttg gtagtcaatg cgacaggcgt aggagcggca   600
gacttggccg acgtacgcga tcccaacgtc tacccaattc gtggacaaac cgttcttatc   660
aatgtaccat ccttcgcctc ccccaatcgc gctgctcgct gcgttatgaa gctctccaag   720
cccaacgcct actacgtcat tccacgagca aggtctgggc aagtcatcct cggtggaagc   780
tttgaacttc ggcaatcatc caccacccct gatcgcaact ggcggaaaag gatcatggaa   840
gagtgcgcaa agctggtgcc tgaaattgta cccgagggaa agacatggaa agatatcgac   900
gttgtttctc acaatgtcgg cttgagacct gctaggagaa tggggctag ggttgagttg    960
gagaggttgg gaggaaatgg gttgacggtg gttcattcgt atggaatcgg tccggcaggc  1020
tatcaggcta gttttggtat cgcaaaggag gtggctgatc tggtggataa gcatgctggt  1080
cgccagtcga ggctgtag                                                1098
```

<210> SEQ ID NO 28
<211> LENGTH: 365
<212> TYPE: PRT
<213> ORGANISM: Ustilago maydis 521

<400> SEQUENCE: 28

```
Met Thr Asn Gln Leu His Val Val Leu Gly Ala Gly Val Leu Gly
1               5                   10                  15
Leu Thr Asp Ala Phe Glu Leu Arg Glu Arg Gly Tyr Arg Val Thr Ile
            20                  25                  30
Leu Ala Arg Asp Leu Pro Phe Asp Ser Phe Ser Gln Thr Phe Ala Ser
        35                  40                  45
Pro Trp Ala Gly Ala Asn Trp Cys Ser Phe Ala Thr Leu Asp Asp Lys
    50                  55                  60
Pro Ala Gln Arg Arg Asp Glu Ile Thr Phe Lys Lys Trp Leu Lys Leu
65                  70                  75                  80
His Thr Arg Leu Pro Glu Glu Val Met Ala Ile Met Glu Phe Thr Asp
                85                  90                  95
Ile Gly Leu Thr Lys Arg Asp Thr Lys Asp Val Trp Phe Ser Asn Leu
            100                 105                 110
Thr Pro Glu Phe Ser Val Leu Pro Asp Ala Asp Glu Met Gly Ala His
        115                 120                 125
Ala Ile Lys Tyr Lys Ser Phe Thr Ile Ser Val Pro Leu Tyr Thr Arg
    130                 135                 140
Trp Leu Val Ser Glu Leu Thr Ser Thr Lys Pro Ile Leu Leu Asp Ala
145                 150                 155                 160
Thr Arg Ala Gly Pro Pro Val Glu Ile Arg Arg Cys Ser Thr Leu Thr
```

165                 170                 175
Ser Leu Ser Ala Val Arg Ser Leu Val Pro Gly Cys Asp Leu Val Val
        180                 185                 190

Asn Ala Thr Gly Val Gly Ala Ala Asp Leu Ala Asp Val Arg Asp Pro
    195                 200                 205

Asn Val Tyr Pro Ile Arg Gly Gln Thr Val Leu Ile Asn Val Pro Ser
    210                 215                 220

Phe Ala Ser Pro Asn Arg Ala Ala Arg Cys Val Met Lys Leu Ser Lys
225                 230                 235                 240

Pro Asn Ala Tyr Tyr Val Ile Pro Arg Ala Arg Ser Gly Gln Val Ile
                245                 250                 255

Leu Gly Gly Ser Phe Glu Leu Arg Gln Ser Ser Thr Thr Pro Asp Arg
            260                 265                 270

Asn Leu Ala Glu Arg Ile Met Glu Glu Cys Ala Lys Leu Val Pro Glu
        275                 280                 285

Ile Val Pro Glu Gly Lys Thr Trp Lys Asp Ile Asp Val Val Ser His
    290                 295                 300

Asn Val Gly Leu Arg Pro Ala Arg Glu Asn Gly Ala Arg Val Glu Leu
305                 310                 315                 320

Glu Arg Leu Gly Gly Asn Gly Leu Thr Val Val His Ser Tyr Gly Ile
                325                 330                 335

Gly Pro Ala Gly Tyr Gln Ala Ser Phe Gly Ile Ala Lys Glu Val Ala
            340                 345                 350

Asp Leu Val Asp Lys His Ala Gly Arg Gln Ser Arg Leu
        355                 360                 365

<210> SEQ ID NO 29
<211> LENGTH: 1267
<212> TYPE: DNA
<213> ORGANISM: Sporisorium reilianum

<400> SEQUENCE: 29
atgaccggac agtctcacgt cgtggtgctt ggagccggag gtaagcaacg cttcagtagc      60
cagttgatga tgatcagcgc aactcactcg atttccgctt cctcgtgttg ttcgacagtg     120
ctcgggctga ccgacgcctt tgagctgcga gagcgaggct acaaggtcac catcctcgcc     180
cgcgatctgc cgcaggactc cttctctcaa acgttcgcca gtccttgggc ggtgagtagc     240
aaccacgacc tcccaccagt cactcattga agatcaccac tgacacacct caccttttca     300
ccgcacgaca cagggagcca actggtgctc gttcgcaacg ctcaccgaca caccagccca     360
gcgtcgcgac gagatcacct tcaaaaagtg gctccagctc cacaccgat gccaccgca      420
agtcatggcc atggtcgagt tcaccgacat cagccccgtc aagcgcgaag ccaaggacgt     480
atggttcagc cgactcactc ccaacttcgc cgtcatcccc gaaggcgacg gtacgggcgc     540
acacgcgatc aggtacgact cgttcaccat cagcgtgccg ctgtacacgc agtggctggt     600
ctcggagctc acatccccga agcccgtgct gttggacgcg gcgcgagcag gaccgccggt     660
cgagatccga cgctgctcga cgctggcgtc gctggcggct gtgcggtcgc tggtgccggg     720
gtgcgacgtg gtcgtcaatg cgacgggggt cggtgcgggc gatctggccg acgtgcgcga     780
tcccgacgtg tatccgatcc gcggacagac ggtgctcgtg tccgtaccgg cgttcaagag     840
ccccaacaac ggcgctcggt gcgtcatgaa gctcggcagc ccgccaagt acgtcatccc      900
acgagcgcgg tccggccagg tcatcctcgg cggttcgttt gatgttcgac agtccagcac     960
cacgcccgat aaagcgctgg cggacaagat cctgcaggac tgcgccaagc tcgtgccgga    1020

```
gatcgtaccg gagggcaaga cgtggcgcga gatcgatgtc atctcgcaca atgttggatt    1080
gaggccaggc agggacaatg gagccagggt ggagctggag cacatccaac ccaaggacgg    1140
cgctgccagg ttgacggtgg tccattcgta cggcatcggt ccggcgggat atcaggccag    1200
ctttggcatc gcgaaggagg tggctgactt ggttgacgga cacctcgctc gtcaagctcg    1260
attgtaa                                                               1267
```

<210> SEQ ID NO 30  
<211> LENGTH: 368  
<212> TYPE: PRT  
<213> ORGANISM: Sporisorium reirlianum

<400> SEQUENCE: 30

```
Met Thr Gly Gln Ser His Val Val Leu Gly Ala Gly Val Leu Gly
1               5                   10                  15

Leu Thr Asp Ala Phe Glu Leu Arg Glu Arg Gly Tyr Lys Val Thr Ile
            20                  25                  30

Leu Ala Arg Asp Leu Pro Gln Asp Ser Phe Ser Gln Thr Phe Ala Ser
        35                  40                  45

Pro Trp Ala Gly Ala Asn Trp Cys Ser Phe Ala Thr Leu Thr Asp Thr
    50                  55                  60

Pro Ala Gln Arg Arg Asp Glu Ile Thr Phe Lys Lys Trp Leu Gln Leu
65                  70                  75                  80

His Thr Arg Leu Pro Pro Gln Val Met Ala Met Val Glu Phe Thr Asp
                85                  90                  95

Ile Ser Pro Val Lys Arg Glu Ala Lys Asp Val Trp Phe Ser Arg Leu
            100                 105                 110

Thr Pro Asn Phe Ala Val Ile Pro Glu Gly Asp Gly Thr Gly Ala His
        115                 120                 125

Ala Ile Arg Tyr Asp Ser Phe Thr Ile Ser Val Pro Leu Tyr Thr Gln
    130                 135                 140

Trp Leu Val Ser Glu Leu Thr Ser Pro Lys Pro Val Leu Leu Asp Ala
145                 150                 155                 160

Ala Arg Ala Gly Pro Pro Val Glu Ile Arg Arg Cys Ser Thr Leu Ala
                165                 170                 175

Ser Leu Ala Ala Val Arg Ser Leu Val Pro Gly Cys Asp Val Val
            180                 185                 190

Asn Ala Thr Gly Val Gly Ala Gly Asp Leu Ala Asp Val Arg Asp Pro
        195                 200                 205

Asp Val Tyr Pro Ile Arg Gly Gln Thr Val Leu Val Ser Val Pro Ala
    210                 215                 220

Phe Lys Ser Pro Asn Asn Gly Ala Arg Cys Val Met Lys Leu Gly Ser
225                 230                 235                 240

Pro Ala Lys Tyr Val Ile Pro Arg Ala Arg Ser Gly Gln Val Ile Leu
                245                 250                 255

Gly Gly Ser Phe Asp Val Arg Gln Ser Ser Thr Thr Pro Asp Lys Ala
            260                 265                 270

Leu Ala Asp Lys Ile Leu Gln Asp Cys Ala Lys Leu Val Pro Glu Ile
        275                 280                 285

Val Pro Glu Gly Lys Thr Trp Arg Glu Ile Asp Val Ile Ser His Asn
    290                 295                 300

Val Gly Leu Arg Pro Gly Arg Asp Asn Gly Ala Arg Val Glu Leu Glu
305                 310                 315                 320
```

His Ile Gln Pro Lys Asp Gly Ala Ala Arg Leu Thr Val Val His Ser
      325                 330                 335

Tyr Gly Ile Gly Pro Ala Gly Tyr Gln Ala Ser Phe Gly Ile Ala Lys
          340                 345                 350

Glu Val Ala Asp Leu Val Asp Gly His Leu Ala Arg Gln Ala Arg Leu
      355                 360                 365

<210> SEQ ID NO 31
<211> LENGTH: 1000
<212> TYPE: DNA
<213> ORGANISM: Rhodosporidium toruloides ATCC 10657
<220> FEATURE:
<221> NAME/KEY: misc_feature
<222> LOCATION: (779)..(806)
<223> OTHER INFORMATION: DNA motif 1

<400> SEQUENCE: 31

```
ctgatcgctt gtgtgcgaga ggtcgaccat catgccgagc tgttcagct   ccggtacaag      60 ctcgcgcccg aaggcggtca ggccgttccc gtcgtgtaca ggctcgatag gagagccgtc     120
cccggcggaa gaggcgaagg ctgtgagaaa acccgtcaa  cagagcggaa gaaggccgag     180
aggtcgcctc gcctcacaag tgtggcaggt gtgcgtgagc gtaaggtacc gcacgccgag     240
ttgctgaaag aggcgtagga tggccagcga gttcatcagg tgatgcgagc tgtaggaaga     300
gcgggttagc gggaggatgt cggtagagac tgttcgtaca aaccctcta gcccaatcaa      360 ggacgcgatc ttcccctccg cgaacgcact ccgcacctcg tccgccgttc gagcgagcgc     420
catctcctca ggatagtgct ccaccatccg atgaataagg tcgacgctct cgagtgccca     480
ctcgaccgcg ttcgtgggct caaggaagtc ctccccccgtc ggctgcgcat cacacggagc    540
atacgcaaca tggaacaagc ctcctacgcg tccttgacgc aacttcggga ggtcgacatg    600
gcctgcaaga ccggtcgcaa gttcagggag gacgtcgagc ggtctccggc agaggtggcg    660
agcgacgtag gggaggtcga cgtgtccgtc tatgagtggg tggcgtttca ggatcccgcg    720
ggcctcagcg agcaaggact cgttgggcaa agtgaaggtg tactgatgag cggttgcgag    780
gccgcagagc agcgctgcga cgacgggaag cttcggcacg agcatgactg tgagtagtag    840
tccaaggaga acagcgcaga gtcggcagga gggcacatgg aggcagagcg tggggcggag    900
gaggcagatg gggagtcgcg ctggggggacg agagggtgcc gctcgaccaa ctgctctctt    960
tcgctcttgc tgctgcttgt actgctcgaa cgacgccatg                          1000
```

<210> SEQ ID NO 32
<211> LENGTH: 1000
<212> TYPE: DNA
<213> ORGANISM: Rhodosporidium toruloides MTCC 457
<220> FEATURE:
<221> NAME/KEY: misc_feature
<222> LOCATION: (779)..(806)
<223> OTHER INFORMATION: DNA motif 1

<400> SEQUENCE: 32

```
tctgatcact ggtgtgcgag aggtcgacca tcatgccgag cctgttcagc tccggtacga      60
gttcgcggcc aaatgcagtt aggccattcc cgtcatgcac aggctcgata ggagagccat     120
cgccggcgga agaggcaaag gctgcgggag cattgggtca gcaagctaac cgaagtgaag    180
gactggatcc gctcacaggt gtggcaggtg tgcgtgagcg tgaggtatcg cacgccaagt    240
tgctggaaga gtcgcaggat ggcgagcgag ttcatcaggt gatgggagct gttcgcaaga    300
gccagtcagc gggacgaagt cgggatagac tgttcgtgca cacccttcca agccaataag    360
```

```
cgacgcaatt ttgccctccg caaacgcact ccgcacctcg tccgctgtcc gagcgagtgc      420
catctcttca ggataatgct cgaccatccg atgaatgagg tcgacactct cgagcgccca      480
ctcgaccgca ttcgtcggct cgaggaagtc ctctcccgtc ggttgcgcat cgcagggagc      540
atacgcgaca tggaacaagc ctcctacgcc tcctcgacgc agtttcggga ggtcgacatg      600
gcctgcgagg ccggttgcga gttcagggag gacgtcgagc ggtctccggg agaggtggcg      660
ggcgacgtag ggaaggtcga cgtgtccgtc gatgagtggg tggcgtttca ggatcccgcg      720
ggcttcagcg agcaaggagt cgtcgggtaa agtgaaggtc gactggtaag cgtttgcaag      780
gccgcagagc agcgctgcga cgacgggaag cttcggcacg agcatgagtg tgaatgatgg      840
tccaaggagg acagcgcaga gtcaacagga gggcacatgg aggcagagcg tggggcggag      900
gaggcagatg gggagtcgcg ctgggggacg aggggtgtc gctcgactaa cagctctcta      960
tcgctcttgc tgctgcttgt actactcgaa cgacgccatg                          1000
```

<210> SEQ ID NO 33
<211> LENGTH: 1000
<212> TYPE: DNA
<213> ORGANISM: Rhodosporidium toruloides NP11
<220> FEATURE:
<221> NAME/KEY: misc_feature
<222> LOCATION: (779)..(806)
<223> OTHER INFORMATION: DNA motif 1

<400> SEQUENCE: 33

```
tctgatcact ggtgtgcgag aggtcgacca tcatgccgag cctgttcagc tccggtacga       60
gttcgcggcc aaatgcagtt aggccattcc cgtcatgcac aggctcgata ggagagccat      120
cgccggcgga agaggcaaag gctgcgggag cattgggtca gcaagctaac cgaagtgaag      180
gactggatcc gctcacaggt gtggcaggtg tgcgtgagcg tgaggtatcg cacgccaagt      240
tgctggaaga gtcgcaggat ggcgagcgag ttcatcaggt gatgggagct gttcgcaaga      300
gccagtcagc gggacgaagt cgggatagac tgttcgtgca cacccttcca agccaataag      360
cgacgcaatt ttgccctccg caaacgcact ccgcacctcg tccgctgtcc gagcgagtgc      420
catctcttca ggataatgct cgaccatccg atgaatgagg tcgacactct cgagcgccca      480
ctcgaccgca ttcgtcggct cgaggaagtc ctctcccgtc ggttgcgcat cgcagggagc      540
atacgcgaca tggaacaagc ctcctacgcc tcctcgacgc agtttcggga ggtcgacatg      600
gcctgcgagg ccggttgcga gttcagggag gacgtcgagc ggtctccggg agaggtggcg      660
ggcgacgtag ggaaggtcga cgtgtccgtc gatgagtggg tggcgtttca ggatcccgcg      720
ggcttcagcg agcaaggagt cgtcgggtaa agtgaaggtc gactggtaag cgtttgcaag      780
gccgcagagc agcgctgcga cgacgggaag cttcggcacg agcatgagtg tgaatgatgg      840
tccaaggagg acagcgcaga gtcaacagga gggcacatgg aggcagagcg tggggcggag      900
gaggcagatg gggagtcgcg ctgggggacg aggggtgtc gctcgactaa cagctctcta      960
tcgctcttgc tgctgcttgt actactcgaa cgacgccatg                          1000
```

<210> SEQ ID NO 34
<211> LENGTH: 1000
<212> TYPE: DNA
<213> ORGANISM: Rhodotorula glutinis ATCC 204091
<220> FEATURE:
<221> NAME/KEY: misc_feature
<222> LOCATION: (779)..(806)
<223> OTHER INFORMATION: DNA motif 1

<400> SEQUENCE: 34

```
ctgatcgctt gtgtgcgaga ggtcgaccat catgccgagc ctgttcagct ccggtacaag    60
ctcgcgcccg aaggcggtca ggccgttccc gtcgtgtaca ggctcgatag agagccgtc   120 cccggcggaa gaggcgaagg ctgtgagaaa aacccgtcaa cagagcggaa gaaggccgag   180
aggtcgcctc gcctcacaag tgtggcaggt gtgcgtgagc gtaaggtacc gcacgccgag   240
ttgctgaaag aggcgtagga tggccagcga gttcatcagg tgatgcgagc tgtaggaaga   300
gcgggttagc ggggaggatgt cggtagagac tgttcgtaca aacccctcta gcccaatcaa   360
ggacgcgatc ttcccctccg cgaacgcact ccgcacctcg tccgccgttc gagcgagcgc   420
catctcctca ggatagtgct ccaccatccg atgaataagg tcgacgctct cgagtgccca   480
ctcgaccgcg ttcgtgggct caaggaagtc ctcccccgtc ggctgcgcat cacacggagc   540
atacgcaaca tggaacaagc ctcctacgcg tccttgacgc aacttcggga ggtcgacatg   600
gcctgcaaga ccggtcgcaa gttcagggag gacgtcgagc ggtctccggc agaggtggcg   660
agcgacgtag ggaggtcga cgtgtccgtc tatgagtggg tggcgtttca ggatcccgcg   720
ggcctcagcg agcaaggact cgttgggcaa agtgaaggtg tactgatgag cggttgcgag   780
gccgcagagc agcgctgcga cgacgggaag cttcggcacg agcatgactg tgagtagtag   840
tccaaggaga acagcgcaga gtcggcagga gggcacatgg aggcagagcg tggggcggag   900
gaggcagatg gggagtcgcg ctgggggacg agagggtgcc gctcgaccaa ctgctctctt   960
tcgctcttgc tgctgcttgt actgctcgaa cgacgccatg                         1000
```

```
<210> SEQ ID NO 35
<211> LENGTH: 1000
<212> TYPE: DNA
<213> ORGANISM: Rhodotorula graminis WP1
<220> FEATURE:
<221> NAME/KEY: misc_feature
<222> LOCATION: (693)..(720)
<223> OTHER INFORMATION: DNA motif 1

<400> SEQUENCE: 35
```

```
agcgagggag tgtgtatatt cgcagaggga gactcgcaac aagcaaatct gtacgaccgt    60
cgccgaccca ttgtaccacc ccctcccctc gtagtcgtct gctgcaacct gccctcctct   120
cccatctctc ggaccgtcgt gagcggcccc gagagcgctt gcgacctcgc tctggctcgt   180
gcgcttcgag ttgtcgagct gcgagggtgc ggcttggcga tgtcgtcggg gtggaaggtg   240
ctgtggcgga cctgcatgcg tcggagggac agggagagaa agagagtcag tgaggttgct   300
cgggacgagg agaacggctg cttgtgctct tgaagcggga gggggccaa aggatcagat   360 ctggcctaat gtgtcgccat gtcgagcgcc tcgtcctcgc cgatccagtc gagcgcaccg   420
cgccgccgga acgcacagcg cgagggaagg gttggcgacg gcgagtgagg tccgtcgaag   480
agggagggca ggacgagagg cgccacgaga actcggatat ccattctgtg tgtgtcatcg   540
tgtcgagagg ggccctcctg cttcgcgttc gagtgagaga gagctcacct cgaggttcga   600
gtgcgagtcg agcggtcggg gcgagggctc agccggcggg gatgccgcgc ttgtggtgct   660
tgacggcggc gaggctcatg ctcatggtga cgaggacgaa gccgaggaac ttgaagaagg   720
cggtgcgcga gtactcgcgc tcctcgagag gcgagcggaa cgaggcgaac tggacggtgg   780
ggacggggtc agcgcggggc acgcacgagg gaggggagga gagggtgcgc acaatgttgc   840
gcaggttggg cagagccatg gcggtgttgg tcgagcgagt cgagtgaccg tcctggacga   900
gacgtcgagc gacaacgacg cttggctcca ccgccgcgcc cgctgcagca ctagccgctc   960
```
ccgctgagcc agcttgctcc ctctcgttcg cactacaatg         1000

<210> SEQ ID NO 36
<211> LENGTH: 1003
<212> TYPE: DNA
<213> ORGANISM: Sporobolomyces roseus
<220> FEATURE:
<221> NAME/KEY: misc_feature
<222> LOCATION: (748)..(775)
<223> OTHER INFORMATION: DNA motif 1

<400> SEQUENCE: 36
cctagctatc aagtgattga actctcgagg cgaaggaaag agacagagat agagagcgag     60
agcgaggtgt gtcggaggag cgcttggatt gactagtagg aaggtgtcga tttgatcgcc    120
tcgtctcgtt ggcggagaaa ggaggggggt gccgtctgcg cgcgtggggc acggatgaac    180
gaacgaaact gttggacccg cccaagccgg aaacaaccaa gttttcggat cgccccgaag    240
atcctgcctg tcgcccgaac gaagaaggga acgagttttt ttagtcagct ctatttggat    300
cgtctctggg aggtcgcgaa cgtggttccg tagaaaagta ggttcagatc tggccttgtt    360
tctttcttcg ccatgagaga ggaacaatga gaaacctcgc ccttgtacat ctccaacctg    420
gtccccactc atcctttctc cgattcctct agagacgcac actccgagga gagggttcct    480
tgagagagag gaagagagcg aggcggttga atgaaggacg acaaaagacg agatctcaga    540
ttgttcgaga gagtgtgtgt gtgaatgtcc gatatccatt ctgttgctat attgctcatc    600
ctgtactttg ggtatacgct gccgacgcta gcgagctaga gagagcgaga gagagagaat    660
gctcaccttt tggttcatca acgcaggagg atcgatagat ggttgcgttt gttctttgtc    720
gcgatcaaac tcatgctcat cgtgacgagg acccagccga ggaacttgaa gaaggccgta    780
cgagagtact cgcgttcttc gagcggagat cgaaacgatg caaactgatc gatccacggg    840
aacccggcgc gtcagtctcg atccaacagt tggaagagta ccaccagact cacaatgttg    900
cggaggttgg gtagagccat gtttcagagt gaggaatccg aggacaaacg atcagcttga    960
ctcttgacac ttgactcttc actcttgttt cccttcgatc atg                     1003

<210> SEQ ID NO 37
<211> LENGTH: 1003
<212> TYPE: DNA
<213> ORGANISM: Puccinia triticina

<400> SEQUENCE: 37
ctgtctttcc aaagaaaaaa gaaaacagta tttacgcaaa aagaataaat gaacgctggt 60
caggttactg accagcttaa tttttacttc cttggtttgt ctaggatata tagtggtttg 120
ataagaaact ggctttcgct ttcaatagca tcacatggcg tatggtacaa attaccacaa 180
ccattaaatc tggtgcctgt ctaccgtagt accacgtcag aaggaaaagg actgagtaag 240
tttgattatc cactggctct gaaggctctg atccggacac cgcagatccg tcgaaatgcg 300
gcaaccctcc agacccgatc cgtattcggg acggagctga tgaaatctag gatccggccg 360
taaaagtgag gctttgggta aaccccggaa agccgcctca gatcggggat tccttcgggg 420
aattcctggg aatctcgcag cacgagctta ttgttgtact tttgtttttg caataaatat 480
caaaaatagc cacattgaaa tccagttgaa tccgaccgga ttctggatac gaccagggag 540
agggtgcggg ataggtgata tattccagct ccgaggcacc ggattggacc ctcaaaattt 600
attctggctc gaaggagacg gcgatggaag cttcactgtg tgatggctac cattcagttc 660
tccaccagga agtgaggttt ggcaacagtt tcagccgata gcatatcatg ccctcatctg 720

| | |
|---|---|
| tatatcctct tcagcatcgg tggtctttaa ccctggtgga ccaagcatgg atggatgcac | 780 |
| tccatggttt gatttgaaag acatgtttgt aatatacctt gtctccgagg aggtttcccc | 840 |
| gctcctgctg tgcaatcagg tgcctttatg tattttgagg accatcattc ctggtctcaa | 900 |
| gccattcagt taacatctca tcaagtgccc acccccaagg acatattatc gccccacgaa | 960 |
| tctggtcctt caatcctcga gttgctagtg atctctggtc atg | 1003 |

<210> SEQ ID NO 38
<211> LENGTH: 1003
<212> TYPE: DNA
<213> ORGANISM: Puccinia graminis

<400> SEQUENCE: 38

| | |
|---|---|
| tcccaagaaa atgtccattt ttcaagggg gtggggccca ataaccggcc tgtgtaccta | 60 |
| aagtgttaca cagaaagata gagaagatct gggggatttt gtctgtctaa aaggcagaga | 120 |
| ttcattccag tggaaaggga gggaaatggt tggaggaaac tttttcccta tcaacagctc | 180 |
| ccagcttgca cacaaaaaca cagaccttca gggcaagtcc ctcctttgga ggggtgcccg | 240 |
| gtgctttgca ccagcctgat ctcaggcccc ccgattgagg ggcttgtggt taggaatcaa | 300 |
| aaaacaggga tttgtataca acagcatttg atccagtttg atgtgaattt cagacctgat | 360 |
| tcctgttcct ggagggtttt cctagacagg agcacagttt cacaagtggt ctttctcttt | 420 |
| actgggtttt gacctgcaca ggctcttgag gcagttttga accccctat tgggttaggt | 480 |
| ggtgaacagg aatgatcttt tcattacttt caaaaaatca tagaagggga ccaagctgg | 540 |
| cagatgagga gatgagacca cctgccaaat gaaagcttgg tcctaaaagt tcaatctggc | 600 |
| tctgagccag gctcgaggcc tgtagagcat tataaggcta aggagccagg gccttaacaa | 660 |
| attaatccat tcacttgcca gccatttgca tttgatgtcc caaccaaaaa atttggcttg | 720 |
| gggagttgtg atatgtaagt gaggaaggac ttggttaagt caggctcggc tcgagaaaca | 780 |
| gccgactgcg taactccatt ggcatttgga tgagttgata gtggaatggc cagtgctcat | 840 |
| gggttccagt gaaatcgatt gatctctcca agaaatctt aaatattagc ctgaagaaac | 900 |
| ataagcatca ctgctcactt aaaatcatcc ttaacaagtc attcatatcg aattcctacc | 960 |
| cccctgaatc tgatcggttg agccgccagt atctcttgtc atg | 1003 |

<210> SEQ ID NO 39
<211> LENGTH: 1003
<212> TYPE: DNA
<213> ORGANISM: Rhodotorula minuta

<400> SEQUENCE: 39

| | |
|---|---|
| gtggcatttg ctccattgac tgatccatcg tctgttccct caatagatcc ctctcttgtc | 60 |
| cttgtagtgt catcctctac tatgtgctgg tcctctcctt gctgaggatg ttgccctccc | 120 |
| tcattctccc tggaatgctg ctcttccatg ctaccttccg tatcgctctt ctccttcttc | 180 |
| aaacgcagcg acgagctagc tgactactac tactcttctg gatcaggtct cttatctaat | 240 |
| aatgaacgct ttcaaagcat gcttttatac accccggtga ctacggtgat ggatgtgata | 300 |
| tctttctcgg tcatcaaaga gaagagccgc ctcagaatga ctgttcgaaa gagagctaac | 360 |
| tcggtcattt ggagaaatga cacacattca caaagacacc gactctttg cctttctggc | 420 |
| cagcaataaa caactacagg tatacatctg cattctaacg tgcattgatg gagtggacag | 480 |
| cagctcaaca atgccaatgc aggccatacg aagtccgcct accgcagctg ccaacgccag | 540 |

-continued

```
ctttgaagat cacgagaacg ttgtagtcag agctagatag ggcaccgtgc tcctctgagg      600
ccatgcagac cttctgaaga ctttagcagt catatatacc tgcctcatgc tgccttagga      660
gcccattgct gccttccgta cacaataagc ggtttcctcg cctcagacct gtactttgga      720
agacgtatgc cactattccg ctgggtcatc catgtgggcg ccggaaaacc cacacgatgc      780
aagcgtgcga gcagaatgct aatcaaagcc agattgctat acattacgag tcaaagccgt      840
atccgctagc tgtgcgagcg accacgcaga aatgtcaatg ctttcaagat aagctatctt      900
tggcttctta gcaggccgat cgggcgtctc tcaaacaagt tcaaacggac cggaagcgat      960
aacctgcttt tcttcttcat aaccacacat tctgacaagc atg                      1003
```

<210> SEQ ID NO 40
<211> LENGTH: 1000
<212> TYPE: DNA
<213> ORGANISM: Sporobolomyces linderae
<220> FEATURE:
<221> NAME/KEY: misc_feature
<222> LOCATION: (716)..(743)
<223> OTHER INFORMATION: DNA motif 1

<400> SEQUENCE: 40

```
tcgagccatc aggccgacct cgaccgggcg cgcttcgatc tcagatcagc cgggccgccg       60
acgatggagt accggagtcg gtcggtcccg caggcgccgg ggtattggcc gcagccgccg      120
tcgttgccgc cgagccatcc ggcgcaggcg atgatggcgc cgccgctgat cgcgccgccg      180
ccgctcgggc gacgagcgac cgtgccatcg ccgtcgcatt cgctcggcgg gccgtggacg      240
catcaggcgc cgccatcggc ctacacgcat ccgcaggccg cggccttcta ctcgccgcca      300
ttgccgacgt cgccctactc gcccgcggcc tcgcccatgt cgccgtccga ttcgaccacg      360
tcggcgggcg acagcgacct gccgcgctac gcgtgtacgc agtgtccgaa gcgattctcg      420
tgcgctcgtc gttcttcttc gcaacgctga cctcgcagtc gccctcttc gctgcgcatt      480 caccagtaca gccactcggg cgagcggtgc gtcggcgatg catcgggcga tctgaccatc      540
taggcccttc gtctgcgaag agtgcggtcg cggcttcagc gtgcaggtgc gtttgcgctg      600
cagtgccttg atctgaccgg ctctcagagc aatctgcgtc ggcacggccg cgtccatcag      660
cccaagtcgg gcgtgccgcc ttcgcccgct gcgtccaccg tcacgatcgt cgaggaggac      720
gactacgacg aggatgagga cgcgatgcag gtgggatgag gcggcgacgc ggcgctgtca      780
atggcgctgt cggagcgaag ttcacgttcg atcgtccatt cgacgatacc cacgccaatc      840
tgtgtacaac acatgctcct ccgttaccct gtgcactatc atacaagtct ttcacacttg      900
tccacgcggc ccaagcttgt ctgcgcggca acccgagcgc gcgagcgcgc gagcgacgtt      960
tccgagtcac cccctctccg cccgctctcc cagcagcatg                           1000
```

<210> SEQ ID NO 41
<211> LENGTH: 1003
<212> TYPE: DNA
<213> ORGANISM: Ustilago maydis 521
<220> FEATURE:
<221> NAME/KEY: misc_feature
<222> LOCATION: (533)..(560)
<223> OTHER INFORMATION: DNA motif 1

<400> SEQUENCE: 41

```
gagtaacgtg caggagccgt agtccgagtg agaaccagca cggatgcttg tagttgccga       60
tgtgtcagta gatgaatcgc aaacggcagt cggaggatag tgaatcagcc gcaatcgatc      120
atgctggcca tgatgtgaat cggcaaagta tctcgtaggc agatctatcg cctccgcaaa      180
```

```
gcctgctaaa actgtatcgc agacacccttt gcatttttcg atgaaggtcg caatcgcttc      240
tcgatgctgt gacagtgttg gcggtagcgt ctgtgaaggc ggtcgatact gctcctcaac      300
tgtcgacgat ccccccttcag ctcgagagag gccagcgagg tagaacgact ctttgagatc     360
gccttcagcc ttgctctttg gatcaagacg ctcttgcatc atcgatgtgt agcccgtatt      420
gttattccgg tcctggtggc tctggcgctc agcttccgac tcatttagga agaactcggc      480
actttgactg aagagcagat cgatttcgtc ctggttgata ccatggtggg tgaggtagaa      540
gaagccggtc ttgacgacgg catccaagat ccgtgcaccg aggggtgctc cagcgtcgtc      600
gctatggagt gaaatgatag gaatcggagt tgcttcggcc attctgatag caaatgggtt      660
aaacttcagc ggtccgctcg gcctcgatct ttggagaaaa gtagaagaga cagtcacgag      720
taacacagtg acagcgatca agcaagaaac gttgagcaaa cagaggtaag gtcccttgga      780
actgcgcttt gttttagttt ttctgcctca acaagcaact gtgcgcccac tgaatttccc      840
ggtggaaaag ccggcctgat acggcagtta ccaagccaat gagatcaatt cagaaaccac      900
atatctcctt ggagccaacg tcgctcccga ccatcgccac gcctactact cgcgtacctc      960
gccacgctac tacctctgat cagcattgcc atctagcgcg atg                      1003

<210> SEQ ID NO 42
<211> LENGTH: 1003
<212> TYPE: DNA
<213> ORGANISM: Sporisorium reilianum
<220> FEATURE:
<221> NAME/KEY: misc_feature
<222> LOCATION: (610)..(637)
<223> OTHER INFORMATION: DNA motif 1

<400> SEQUENCE: 42
accacaatgc atcccctttg cggtggaatg tcgacccact ggcccggctt catctcgact       60
tgcagcccgc cgacgtcctt ttggaagagc agcgtacacg agccgtagtc cgaatgagaa      120
cctgcacgga tgcttgtcgt cgcagcgtcg tcgctcgata cgggagttgg aggatagtgg      180
atgaggcgca atcgatcatg ctgtccatgg tgcgagtcgg caaagtaccg cgagggcaga      240
tcgatcgctt ccgcaaagcc ggccaggatc gtatcgcaga cgccttttgca cttttcgatg     300 aatgtcgcga gcacctcttt gtgctgcgac agtgtgggcg gcaacgactg tgacggaggt      360
cgatagcgct cttctgcggg agacgagcct ccttccaccc tggccaggcc cacgagatag      420
aatgactcct tgaggtcgcc ttccgccttg ctccccgtat ccagccgctc cgacttcatc      480
gccgtatagc ccgtgttgtt ggcgcggtct tggcattgta gccgctcgtg ttccgcttcg      540
tggaggaaga actgcgcgct ctgatcgaac agcaggttga tctcatcctg gcggatgccg      600
tggtcggcga ggtagaagaa gcccgtcttg acgacgcgt ccaagatccg tgggcccaac      660
gctgactcgt cgctgccgcc ggtgcggagg gagatgattg gaatcggtgt cgagtccgac      720
atctttgttg tgcgatgtgt cgaggaggac gagaaagcgg gacagaagca gcgacgaaca      780
gacgagagga ccccttgacgg agctttattt ttttgcttgg ctcgataaga gagagagacg     840
gcccgctgat tttcccggct gaaaagacgg cgagaaacga ttgtgcggac ccaatcagaa      900
gaagaaaagc gggactcgta cagctccgca ccaccttacc atcatccatt tgtcgacccc      960
attcctcgcc gagctcgata catcatacaa cactgcaaga atg                      1003

<210> SEQ ID NO 43
<211> LENGTH: 1003
<212> TYPE: DNA
```

<213> ORGANISM: Melampsoria laricis-populina

<400> SEQUENCE: 43
gcaagtgact tgagctggtt gtagttggct gctttatgaa tagtccctgg gtgatgtttg 60
ggctggtgat gtagttcatt tttgacaaaa atacctgttg ggtgggtatc tgaggatgtt 120
aatcttttca ggatcaagtt gtgtgtgatg tctccgcttt gataaccatg tgaatggtgt 180
gagatatgtg tagtggcttt catttgtttg aagtgcattt gaaagctcta acaaataatt 240
cattttctgc gttttgtctc ttttctgata gtctgtttac tttcatgttg ttcagttatg 300
tgtctggggg tgggcatctg gctgtagact acccccaaaa gtaggctctc ctccagtagg 360
gctctgggga aggtgggagg gcatataaaa agttgaggat ttgtgttcca agagcaccca 420
ctatggttgt gttaacaaca tgatttaggg tcagtctcct gctaaaatac agacaggtcc 480
actctagacc tgacttagac ctgcggtcca tacaactttg tcaaatcttg caccctgcgt 540
gttcaaatct acaaccacct acaacttgat ttatagtagg aactaggtaa agcagatgac 600
ccatagtgga tttcatgtgg ttaccaactt aggtaaaaca tgcatgttca aattttgcgt 660
tgaggaacgc aaaatttacg atcaaacact cttaccatag tggattctct aagagctatt 720
gagtgtgtgc tggaacttgt gatacgcggt atacgaaaag cgcgcattga gatttccaac 780
caatatctga gcggcccggt actcgggtct gcgacttttc ggctcacggg agttatccgc 840
gctcccaagc tcaggggtcc ggggaacatt cggaagtcgt cgtgcttttg gacatccgtg 900
gcatacaggg cgacatacca ttacagcctg tcggcacttg acactacttg acttcacttg 960
actctttcta gtcgaatcgc tcgaaagcgt gatagtatca atg 1003

<210> SEQ ID NO 44
<211> LENGTH: 29
<212> TYPE: DNA
<213> ORGANISM: Rhodotorula graminis WP1

<400> SEQUENCE: 44
gaggacgaag ccgaggaact tgaagaagg 29

<210> SEQ ID NO 45
<211> LENGTH: 29
<212> TYPE: DNA
<213> ORGANISM: Ustilago maydis 521

<400> SEQUENCE: 45
gaggtagaag aagccggtct tgacgacgg 29

<210> SEQ ID NO 46
<211> LENGTH: 29
<212> TYPE: DNA
<213> ORGANISM: Sporisorium reilianum

<400> SEQUENCE: 46
gaggtagaag aagcccgtct tgacgacgg 29

<210> SEQ ID NO 47
<211> LENGTH: 29
<212> TYPE: DNA
<213> ORGANISM: Sporobolomyces roseus

<400> SEQUENCE: 47
gaggacccag ccgaggaact tgaagaagg 29

<210> SEQ ID NO 48
<211> LENGTH: 29
<212> TYPE: DNA
<213> ORGANISM: Rhodotorula glutinis ATCC 204091

<400> SEQUENCE: 48
gaggccgcag agcagcgctg cgacgacgg                                29

<210> SEQ ID NO 49
<211> LENGTH: 29
<212> TYPE: DNA
<213> ORGANISM: Rhodosporidium toruloides ATCC 10657

<400> SEQUENCE: 49
aaggccgcag agcagcgctg cgacgacgg                                29

<210> SEQ ID NO 50
<211> LENGTH: 28
<212> TYPE: DNA
<213> ORGANISM: Sporobolomyces linderae

<400> SEQUENCE: 50
gaggacgact acgacgagga tgaggacg                                 28

<210> SEQ ID NO 51
<211> LENGTH: 1660
<212> TYPE: DNA
<213> ORGANISM: Artificial Sequence
<220> FEATURE:
<223> OTHER INFORMATION: Synthetic codon optimized Rhodosporidium
      toruloides LUC-2 gene

<400> SEQUENCE: 51
ccatggagga cgccaagaac atcaagaagg gcccggcccc gttctacccg cttgaggacg      60
gcaccgccgg cgagcagctc cacaaggcca tgaagcgcta cgccctcgtc cccggcacca    120
tcgccttcac cgacgcccac atcgaggtgg acatccccta cgccgagtac ttcgagatgt    180
cggtccgcct cgccgaggcg atgaagcggt acggcctcaa caccaaccac cgcatcgtcg    240
tctgctcgga gaactcgctc cagttcttca tgccggtcct cggcgccctc ttcatcggcg    300
tcgccgtcgc ccccgccaac gacatctaca cgagcgcga gctcctcaac tcgatgggca    360
tctcgcagcc gaccgtcgtc ttcgtctcga agaagggcct ccagaagatc ctcaacgtcc    420
agaagaagct cccgatcatc caaaagatca tcatcatgga ctcgaagacc gactaccagg    480
gcttccagtc gatgtacacc ttcgtcacct cgcacctccc gccgggcttc aacgagtacg    540
acttcgtccc ggagtcgttc gaccgcgaca agaccatcgc cctcatcatg aactcgtcgg    600
gctcgaccgg cctcccgaag ggagtcgccc tcccgcaccg caccgcctgc gtccgcttct    660
cgcacgcccg cgacccgatc ttcggcaacc agatcatccc ggacaccgcc atcctctcgg    720 tcgtccccttt ccaccacggc ttcggcatgt tcaccaccct cggctacctc atctgcggct    780
tccgcgtcgt cctcatgtac cgcttcgagg aggagctctt cctccgctcg ctccaggact    840
acaagatcca gtcggccctc ctcgtcccga ccctcttctc gttcttcgcc aagtcgaccc    900
tcatcgataa gtacgacctc tcgaacctcc acgagatcgc ctcgggcggc gccccgctct    960
cgaaggaggt cggcgaggcc gtcgccaagc gcttccacct cccgggcatc cgccagggct   1020
acggcctcac cgagaccacc tcggccatct catcaccccc ggagggcgac gacaagccgg   1080
gcgccgtcgg caaggtcgtc ccgttcttcg aggccaaggt cgtcgacctc gacaccggca   1140
agaccctcgg cgtcaaccag cgcggcgagc tctgcgtccg cggcccgatg atcatgtcgg   1200

```
gctacgtcaa caacccggag gccaccaacg ccctcatcga caaggacggc tggctccact   1260
cgggcgacat cgcctactgg gacgaggacg agcacttctt catcgtcgac cgcctcaagt   1320
cgctcatcaa gtacaagggc taccaggtcg ccccggccga gctcgagtcg atcctcctcc   1380
agcacccgaa catcttcgac gccggagtcg ccggccttcc ggacgatgac gccggagagc   1440
tcccggccgc cgtcgtcgtc ctcgagcacg gcaagaccat gaccgagaag gagatcgtcg   1500
actacgtcgc ctcgcaggtc accaccgcca agaagctccg cggcggcgtc gtgttcgtcg   1560
acgaggtccc gaagggcctc accggcaagc tcgacgcccg caagatccgc gagatcctca   1620
tcaaggccaa gaagggcggc aagatcgccg tctagatatc                         1660
```

<210> SEQ ID NO 52
<211> LENGTH: 50
<212> TYPE: DNA
<213> ORGANISM: Rhodotorula glutinis 204091

<400> SEQUENCE: 52

```
gtgcgtcttt ccctctcctc cccacacccg acagttctcg aggaggagta               50
```

<210> SEQ ID NO 53
<211> LENGTH: 51
<212> TYPE: DNA
<213> ORGANISM: Rhodosporidium toruloides MTCC 457

<400> SEQUENCE: 53

```
gtgcgtcttt ccctctcct ccccacaccc gacagtcctc gacgaggtgt a              51
```

<210> SEQ ID NO 54
<211> LENGTH: 51
<212> TYPE: DNA
<213> ORGANISM: Rhodosporidium toruloides NP11

<400> SEQUENCE: 54

```
gtgcgtcttt tccctctcct ccccacaccc gacagtcctc gacgaggtgt a             51
```

<210> SEQ ID NO 55
<211> LENGTH: 50
<212> TYPE: DNA
<213> ORGANISM: Rhodotorula graminis WP1

<400> SEQUENCE: 55

```
gtgagcccca gccctcacac tctccccctc cccccacatt ccgaggcctg               50
```

<210> SEQ ID NO 56
<211> LENGTH: 108
<212> TYPE: DNA
<213> ORGANISM: Rhodotorula glutinis 204091

<400> SEQUENCE: 56

```
gtgcgtcttt ccctctcctc cccacacccg acagttctcg aggaggagta cagcagcgag   60
cgaggctgcc gaggggggatc tgggttgacg cagctcttga ttatacag                108
```

<210> SEQ ID NO 57
<211> LENGTH: 109
<212> TYPE: DNA
<213> ORGANISM: Rhodosporidium toruloides MTCC 457

<400> SEQUENCE: 57

```
gtgcgtcttt tccctctcct ccccacaccc gacagtcctc gacgaggtgt aggacggcga   60
```

```
gcaaagctgc cgagggcgat ctgggctgac tgagcgctcg agtgtacag      109

<210> SEQ ID NO 58
<211> LENGTH: 109
<212> TYPE: DNA
<213> ORGANISM: Rhodosporidium toruloides NP11

<400> SEQUENCE: 58
gtgcgtcttt tccctctcct ccccacaccc gacagtcctc gacgaggtgt aggacggcga      60
gcaaagctgc cgagggcgat ctgggctgac tgagcgctcg agtgtacag      109

<210> SEQ ID NO 59
<211> LENGTH: 79
<212> TYPE: DNA
<213> ORGANISM: Rhodotorula graminis WP1

<400> SEQUENCE: 59
gtgagcccca gccctcacac tctcccctc cccccacttt ccgaggcctg actcttccct      60
ctcgcccctc gcctcgcag      79

<210> SEQ ID NO 60
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 60
tttactagtc ttcccggtct cgtatcgag      29

<210> SEQ ID NO 61
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 61
tttactagta ctccgcaatc tgcagagac      29

<210> SEQ ID NO 62
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 62
tttactagtc atggtctgat cgcttgtgtg      30

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 63
tttactagtg tggcaggtgt gcgtg      25

<210> SEQ ID NO 64
<211> LENGTH: 29
<212> TYPE: DNA
<213> ORGANISM: Artificial Sequence
```

```
<220> FEATURE:
<223> OTHER INFORMATION: Oligonucleotide primer

<400> SEQUENCE: 64
tttactagtc gttcgtgggc tcaaggaag                                    29

<210> SEQ ID NO 65
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 65
tttactagtc gacgacggga agcttcg                                      27

<210> SEQ ID NO 66
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 66
tttccatggc aatcactgta taatcaagag ctg                               33

<210> SEQ ID NO 67
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 67
tttccatggc gtcgttcgag cag                                          23

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
gaagcttcgg cacgagcatg                                              20

<210> SEQ ID NO 69
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 69
acagtcatgc tcgtgccgaa gcttcgcaac cgctcatcag tacac                  45

<210> SEQ ID NO 70
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 70
ggacaaacca caactagaat gcag                                         24
```

<210> SEQ ID NO 71
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 71
aaagcatgct aattcggggg atctggat                                    28

<210> SEQ ID NO 72
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 72
ggcgtcgttc gagcagtac                                              19

<210> SEQ ID NO 73
<211> LENGTH: 48
<212> TYPE: DNA
<213> ORGANISM: Artificial Sequence
<220> FEATURE:
<223> OTHER INFORMATION: Oligonucleotide primer

<400> SEQUENCE: 73
ctgcttgtac tgctcgaacg acgccatcca ttcacagaag cgcgtcgt              48

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
gacgcaccgc ctgatccgag                                             20

<210> SEQ ID NO 75
<211> LENGTH: 69
<212> TYPE: DNA
<213> ORGANISM: Artificial Sequence
<220> FEATURE:
<223> OTHER INFORMATION: Oligonucleotide primer

<400> SEQUENCE: 75
ttgtcctcgg atcaggcggt gcgtctttaa atataataaa aaaaaagac agttctcgag  60 gaggagtac                                                         69

<210> SEQ ID NO 76
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 76
ttgtcctcgg atcaggcggt gcgtccagtt ctcgaggagg agtac                 45

<210> SEQ ID NO 77
<211> LENGTH: 19
<212> TYPE: DNA
<213> ORGANISM: Artificial Sequence

```
<220> FEATURE:
<223> OTHER INFORMATION: Oligonucleotide primer

<400> SEQUENCE: 77
gaagtactcg gcgtaggtg                                                    19

<210> SEQ ID NO 78
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 78
cttcgtgcta accaagctcg t                                                 21

<210> SEQ ID NO 79
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 79
gtctcagggt tgacggacaa g                                                 21

<210> SEQ ID NO 80
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 80
tcaaaccgtc ctcgtcaagt c                                                 21

<210> SEQ ID NO 81
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 81
gttgacggac aagtcccaat c                                                 21

<210> SEQ ID NO 82
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 82
cgacaacttt gacgaccctt c                                                 21

<210> SEQ ID NO 83
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 83
caggttggga caagttgggt a                                                 21
```

<210> SEQ ID NO 84
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 84
ggacaaacca caactagaat gcag                                          24

<210> SEQ ID NO 85
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 85
aaagcatgct aattcggggg atctggat                                      28

<210> SEQ ID NO 86
<211> LENGTH: 16
<212> TYPE: PRT
<213> ORGANISM: Rhodosporidium toruloides ATCC 10657

<400> SEQUENCE: 86

Met His Ser Gln Lys Arg Val Val Leu Gly Ser Gly Val Ile Ala
1               5                   10                  15

<210> SEQ ID NO 87
<211> LENGTH: 24
<212> TYPE: PRT
<213> ORGANISM: Rhodosporidium toruloides ATCC 10657

<400> SEQUENCE: 87

Met Ser Ala Gly Lys Gly Ser Val Asn Val Gly Ile Asn Gly Phe Gly
1               5                   10                  15

Arg Ile Gly Arg Ile Val Leu Arg
            20

<210> SEQ ID NO 88
<211> LENGTH: 368
<212> TYPE: PRT
<213> ORGANISM: Rhodosporidium toruloides ATCC 10657

<400> SEQUENCE: 88

Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Val Ala Arg Asp Leu Pro Glu Asp Val Ser Ser Gln Thr Phe Ala Ser
        35                  40                  45

Pro Trp Ala Gly Ala Asn Trp Thr Pro Phe Met Ser Leu Thr Asp Gly
    50                  55                  60

Pro Arg Gln Ala Lys Trp Glu Glu Leu Thr Phe Lys Lys Trp Val Glu
65                  70                  75                  80

Leu Val Pro Thr Gly Gln Val Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Asn Ser Ile

```
            115                 120                 125
Gly Val Thr Tyr Asp Thr Leu Ser Val His Ala Pro Lys Tyr Cys Gln
    130                 135                 140

Tyr Leu Ala Arg Gly Leu Gln Lys Leu Gly Ala Thr Phe Glu Arg Arg
145                 150                 155                 160

Thr Val Thr Ser Val Glu Gln Ala Phe Glu Gly Val Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Ala Cys
        195                 200                 205

Lys Arg Cys Thr Met Asp Ser Ser Asp Pro Ser Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Ser Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Leu Val Leu Pro Leu Asp
    290                 295                 300

Arg Ser Lys Ser Pro Leu Ser Leu Gly Lys Gly Thr Thr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Leu Leu Val
            340                 345                 350

Glu Glu Ala Phe Gln Arg Tyr His Gly Ala Ala Arg Glu Ser Lys Leu
        355                 360                 365

<210> SEQ ID NO 89
<211> LENGTH: 2046
<212> TYPE: DNA
<213> ORGANISM: Rhodosporidium toruloides
<220> FEATURE:
<221> NAME/KEY: CDS
<222> LOCATION: (118)..(2046)

<400> SEQUENCE: 89
tcctctggcc tctctcgctc cgttcgcctg gccgcgcgcc caaaccgctt tgttgacgct      60
atcagcctcc cgcgagcgct agcaggctct cttagccgcc tcacgcctac ctcgcga       117 atg tcc tcc cca cct cgc ttc gcg ccc ggt tcg acc tcg ccc acg cag      165
Met Ser Ser Pro Pro Arg Phe Ala Pro Gly Ser Thr Ser Pro Thr Gln
1               5                   10                  15 tcg agg ccg cgt gcg acg cac agc agc cca aca caa ggt ccc ttc gca      213
Ser Arg Pro Arg Ala Thr His Ser Ser Pro Thr Gln Gly Pro Phe Ala
                20                  25                  30 acg cct gcg cgc cca ggt gcg agc tca gcg gcg cac caa ccc gat cct      261
Thr Pro Ala Arg Pro Gly Ala Ser Ser Ala Ala His Gln Pro Asp Pro
            35                  40                  45 tca acc tcg aca gca ggc gcc gcc tcc ctc ctc acg tct tct cct cac      309
Ser Thr Ser Thr Ala Gly Ala Ala Ser Leu Leu Thr Ser Ser Pro His
        50                  55                  60 tac acg act tcg ctg cgc tct cga cac tcg ctt tac ggc acg gaa gac      357
```

```
Tyr Thr Thr Ser Leu Arg Ser Arg His Ser Leu Tyr Gly Thr Glu Asp
 65                  70                  75                  80 cgt gtt gtg ctg gat ctc ggc tcg cgg ata tgg aag gtc ggg ttc agc        405
Arg Val Val Leu Asp Leu Gly Ser Arg Ile Trp Lys Val Gly Phe Ser
                     85                  90                  95 ggg gag ccg cag ccg cgc gag tgc cgg agc gtc gtg agc gag ttg gcg        453
Gly Glu Pro Gln Pro Arg Glu Cys Arg Ser Val Val Ser Glu Leu Ala
                100                 105                 110 cat gag cgg gct ggg cga aga gca ggg ccg tcc ata ggc gcg aga ggg        501
His Glu Arg Ala Gly Arg Arg Ala Gly Pro Ser Ile Gly Ala Arg Gly
            115                 120                 125 gac gac gac gaa gag gac tgc ttt tgg gcg ctc gag aag gcc gag ccg        549
Asp Asp Asp Glu Glu Asp Cys Phe Trp Ala Leu Glu Lys Ala Glu Pro
130                 135                 140 agc gag gag gag tgg ttg att cgc gag gag agg gtg aag cga tta ctg        597
Ser Glu Glu Glu Trp Leu Ile Arg Glu Glu Arg Val Lys Arg Leu Leu
145                 150                 155                 160 cgc aag atc tgg ttc gaa aac ctc atg atc gac ccg aag acg cgc aaa        645
Arg Lys Ile Trp Phe Glu Asn Leu Met Ile Asp Pro Lys Thr Arg Lys
                    165                 170                 175 gtc atc gtc gtg gag aac cca ctg ctg tcg acg cgc gtg aag gag atg        693
Val Ile Val Val Glu Asn Pro Leu Leu Ser Thr Arg Val Lys Glu Met
                180                 185                 190 atc gcg cgg gtc ttg ttc gac aac ttg cag atc ccg tcg ctc agc ttc        741
Ile Ala Arg Val Leu Phe Asp Asn Leu Gln Ile Pro Ser Leu Ser Phe
            195                 200                 205 gct tcc gcc ccc ttg ctc gcc ttg atg gcg gcc ggc aca gtg acc ggt        789
Ala Ser Ala Pro Leu Leu Ala Leu Met Ala Ala Gly Thr Val Thr Gly
210                 215                 220 ctt gtg gtc gac gtc gga aac ctc gag acg acc gtt ctt ccc gtc ttt        837
Leu Val Val Asp Val Gly Asn Leu Glu Thr Thr Val Leu Pro Val Phe
225                 230                 235                 240 cac gct cgc ccg ctc ttt ccc tcc ctc acc aca act cct cgc gcg ggc        885
His Ala Arg Pro Leu Phe Pro Ser Leu Thr Thr Thr Pro Arg Ala Gly
                    245                 250                 255 tct cgc ctg aac cgc cgc ctc cgc tct ctc ctc ctc gca ttc ggc tca        933
Ser Arg Leu Asn Arg Arg Leu Arg Ser Leu Leu Leu Ala Phe Gly Ser
                260                 265                 270 tac gca cct cct ccc tcc tcc ctc aac tcc atg acg cct ccc gct atc        981
Tyr Ala Pro Pro Pro Ser Ser Leu Asn Ser Met Thr Pro Pro Ala Ile
            275                 280                 285 gga cgg ata ccg aag gag ctc ttg acg gag gag ctc ata gag gag atc       1029
Gly Arg Ile Pro Lys Glu Leu Leu Thr Glu Glu Leu Ile Glu Glu Ile
290                 295                 300 aag acg cgg ctg tgt ttt gtc ggt gag gag gtc ccg ctc gat gcg agc       1077
Lys Thr Arg Leu Cys Phe Val Gly Glu Glu Val Pro Leu Asp Ala Ser
305                 310                 315                 320 cgg ggc gag agg gag gcg tcc gcg ttc agc gga tcg gcc atg agc gtc       1125
Arg Gly Glu Arg Glu Ala Ser Ala Phe Ser Gly Ser Ala Met Ser Val
                    325                 330                 335 gac act gca tca gca cgc gac aac ttt gac gac cct tcc gac ccc gac       1173
Asp Thr Ala Ser Ala Arg Asp Asn Phe Asp Asp Pro Ser Asp Pro Asp
                340                 345                 350 aac gca cta cta aag gag ctt tac tcc cgc ttc gcc gcg aca tcg acc       1221
Asn Ala Leu Leu Lys Glu Leu Tyr Ser Arg Phe Ala Ala Thr Ser Thr
            355                 360                 365 gcc aaa ccc gtt tcc ttc cgg ata ccc aac ttg tcc caa cct gcg atc       1269
Ala Lys Pro Val Ser Phe Arg Ile Pro Asn Leu Ser Gln Pro Ala Ile
370                 375                 380
```

```
gcg aac ggt aca ggt cga ggg tgg atc cag gtg ccc ggc tgg atc agg    1317
Ala Asn Gly Thr Gly Arg Gly Trp Ile Gln Val Pro Gly Trp Ile Arg
385                 390                 395                 400 gag cgc gcc gcc gag gtg ttg tgg gag gag gat ggt gat gga gac gag    1365
Glu Arg Ala Ala Glu Val Leu Trp Glu Glu Asp Gly Asp Gly Asp Glu
            405                 410                 415 cgt ggg ctt gcc gcc gtt gtc ctt gac tgc cta ttg aag ctc ccc ctt    1413
Arg Gly Leu Ala Ala Val Val Leu Asp Cys Leu Leu Lys Leu Pro Leu
        420                 425                 430 gac ctt cga aag ccg atg gcc tcg tca atc ctc ctc acg ggc ggc acc    1461
Asp Leu Arg Lys Pro Met Ala Ser Ser Ile Leu Leu Thr Gly Gly Thr
    435                 440                 445 gcc atg ctc ccc ggc ttc ttc cca cgc ttc aag gcc gct ctt ctt gcc    1509
Ala Met Leu Pro Gly Phe Phe Pro Arg Phe Lys Ala Ala Leu Leu Ala
450                 455                 460 cag ctc gac cgc tcg cat cct cct tcc cct ccg cct tcc ccg cct ctg    1557
Gln Leu Asp Arg Ser His Pro Pro Ser Pro Pro Pro Ser Pro Pro Leu
465                 470                 475                 480 cca gca gca tcc gtc gaa cct cct tct tcc gac cct gcc gga ccc atg    1605
Pro Ala Ala Ser Val Glu Pro Pro Ser Ser Asp Pro Ala Gly Pro Met
            485                 490                 495 tcg acg gac acg gcg gca tcg cct gcg ccc tct cgc tcg agc gaa gtc    1653
Ser Thr Asp Thr Ala Ala Ser Pro Ala Pro Ser Arg Ser Ser Glu Val
        500                 505                 510 aat gcg aag cgg cgg cga aag cat gcc ctc gcg act cga ctg cac aac    1701
Asn Ala Lys Arg Arg Arg Lys His Ala Leu Ala Thr Arg Leu His Asn
    515                 520                 525 ctg cgg cat tcg cct cga tac gcc ccg ctt gtc cct ctc gct cga cac    1749
Leu Arg His Ser Pro Arg Tyr Ala Pro Leu Val Pro Leu Ala Arg His
530                 535                 540 ctc gcc atc ttg aac cac cca tct ccg aac tcc tcg gca tcg tcg acg    1797
Leu Ala Ile Leu Asn His Pro Ser Pro Asn Ser Ser Ala Ser Ser Thr
545                 550                 555                 560 gcg ccc tca tca acc ctc gct cga cag cgc gaa ggt tcg gct ccg tct    1845
Ala Pro Ser Ser Thr Leu Ala Arg Gln Arg Glu Gly Ser Ala Pro Ser
            565                 570                 575 ttc tcg ccc gcc ttg caa agc tgg atc ggc ggc agc ctc gca gga gcg    1893
Phe Ser Pro Ala Leu Gln Ser Trp Ile Gly Gly Ser Leu Ala Gly Ala
        580                 585                 590 ctc aag acg ggc ggg cct gag att gcg agg gag cag tgg gat gca ggg    1941
Leu Lys Thr Gly Gly Pro Glu Ile Ala Arg Glu Gln Trp Asp Ala Gly
    595                 600                 605 ttg cgg ttt gcg gag gca gaa gag gcg gag gga gag gaa gga gag gag    1989
Leu Arg Phe Ala Glu Ala Glu Glu Ala Glu Gly Glu Glu Gly Glu Glu
610                 615                 620 ttt gag gag cgg gaa gtg atc cgg ccg gct ctg ccg gac tgg acg agg    2037
Phe Glu Glu Arg Glu Val Ile Arg Pro Ala Leu Pro Asp Trp Thr Arg
625                 630                 635                 640 atc gcg tag                                                         2046
Ile Ala <210> SEQ ID NO 90
<211> LENGTH: 642
<212> TYPE: PRT
<213> ORGANISM: Rhodosporidium toruloides

<400> SEQUENCE: 90

Met Ser Ser Pro Pro Arg Phe Ala Pro Gly Ser Thr Ser Pro Thr Gln
1               5                   10                  15

Ser Arg Pro Arg Ala Thr His Ser Ser Pro Thr Gln Gly Pro Phe Ala
```

-continued

```
                 20                  25                  30
Thr Pro Ala Arg Pro Gly Ala Ser Ser Ala Ala His Gln Pro Asp Pro
             35                  40                  45
Ser Thr Ser Thr Ala Gly Ala Ala Ser Leu Leu Thr Ser Ser Pro His
 50                  55                  60
Tyr Thr Thr Ser Leu Arg Ser Arg His Ser Leu Tyr Gly Thr Glu Asp
 65                  70                  75                  80
Arg Val Val Leu Asp Leu Gly Ser Arg Ile Trp Lys Val Gly Phe Ser
                 85                  90                  95
Gly Glu Pro Gln Pro Arg Glu Cys Arg Ser Val Val Ser Glu Leu Ala
            100                 105                 110
His Glu Arg Ala Gly Arg Arg Ala Gly Pro Ser Ile Gly Ala Arg Gly
            115                 120                 125
Asp Asp Asp Glu Glu Asp Cys Phe Trp Ala Leu Glu Lys Ala Glu Pro
            130                 135                 140
Ser Glu Glu Glu Trp Leu Ile Arg Glu Glu Arg Val Lys Arg Leu Leu
145                 150                 155                 160
Arg Lys Ile Trp Phe Glu Asn Leu Met Ile Asp Pro Lys Thr Arg Lys
                165                 170                 175
Val Ile Val Val Glu Asn Pro Leu Leu Ser Thr Arg Val Lys Glu Met
            180                 185                 190
Ile Ala Arg Val Leu Phe Asp Asn Leu Gln Ile Pro Ser Leu Ser Phe
            195                 200                 205
Ala Ser Ala Pro Leu Leu Ala Leu Met Ala Ala Gly Thr Val Thr Gly
            210                 215                 220
Leu Val Val Asp Val Gly Asn Leu Glu Thr Thr Val Leu Pro Val Phe
225                 230                 235                 240
His Ala Arg Pro Leu Phe Pro Ser Leu Thr Thr Thr Pro Arg Ala Gly
                245                 250                 255
Ser Arg Leu Asn Arg Arg Leu Arg Ser Leu Leu Leu Ala Phe Gly Ser
                260                 265                 270
Tyr Ala Pro Pro Pro Ser Ser Leu Asn Ser Met Thr Pro Pro Ala Ile
            275                 280                 285
Gly Arg Ile Pro Lys Glu Leu Leu Thr Glu Glu Leu Ile Glu Glu Ile
            290                 295                 300
Lys Thr Arg Leu Cys Phe Val Gly Glu Glu Val Pro Leu Asp Ala Ser
305                 310                 315                 320
Arg Gly Glu Arg Glu Ala Ser Ala Phe Ser Gly Ser Ala Met Ser Val
                325                 330                 335
Asp Thr Ala Ser Ala Arg Asp Asn Phe Asp Asp Pro Ser Asp Pro Asp
            340                 345                 350
Asn Ala Leu Leu Lys Glu Leu Tyr Ser Arg Phe Ala Ala Thr Ser Thr
            355                 360                 365
Ala Lys Pro Val Ser Phe Arg Ile Pro Asn Leu Ser Gln Pro Ala Ile
            370                 375                 380
Ala Asn Gly Thr Gly Arg Gly Trp Ile Gln Val Pro Gly Trp Ile Arg
385                 390                 395                 400
Glu Arg Ala Ala Glu Val Leu Trp Glu Glu Asp Gly Asp Gly Asp Glu
                405                 410                 415
Arg Gly Leu Ala Ala Val Val Leu Asp Cys Leu Leu Lys Leu Pro Leu
            420                 425                 430
Asp Leu Arg Lys Pro Met Ala Ser Ser Ile Leu Leu Thr Gly Gly Thr
            435                 440                 445
```

```
Ala Met Leu Pro Gly Phe Phe Pro Arg Phe Lys Ala Ala Leu Leu Ala
    450                 455                 460

Gln Leu Asp Arg Ser His Pro Pro Ser Pro Pro Ser Pro Pro Leu
465                 470                 475                 480

Pro Ala Ala Ser Val Glu Pro Pro Ser Ser Asp Pro Ala Gly Pro Met
                485                 490                 495

Ser Thr Asp Thr Ala Ala Ser Pro Ala Pro Ser Arg Ser Ser Glu Val
                500                 505                 510

Asn Ala Lys Arg Arg Lys His Ala Leu Ala Thr Arg Leu His Asn
            515                 520                 525

Leu Arg His Ser Pro Arg Tyr Ala Pro Leu Val Pro Leu Ala Arg His
        530                 535                 540

Leu Ala Ile Leu Asn His Pro Ser Pro Asn Ser Ser Ala Ser Ser Thr
545                 550                 555                 560

Ala Pro Ser Ser Thr Leu Ala Arg Gln Arg Glu Gly Ser Ala Pro Ser
                565                 570                 575

Phe Ser Pro Ala Leu Gln Ser Trp Ile Gly Gly Ser Leu Ala Gly Ala
                580                 585                 590

Leu Lys Thr Gly Gly Pro Glu Ile Ala Arg Glu Gln Trp Asp Ala Gly
                595                 600                 605

Leu Arg Phe Ala Glu Ala Glu Ala Glu Gly Glu Glu Gly Glu Glu
        610                 615                 620

Phe Glu Glu Arg Glu Val Ile Arg Pro Ala Leu Pro Asp Trp Thr Arg
625                 630                 635                 640

Ile Ala

<210> SEQ ID NO 91
<211> LENGTH: 29
<212> TYPE: DNA
<213> ORGANISM: Artificial Sequence
<220> FEATURE:
<223> OTHER INFORMATION: DNA motif 1 sequence
<220> FEATURE:
<221> NAME/KEY: misc_feature
<222> LOCATION: (18)..(18)
<223> OTHER INFORMATION: n is a, c, g, or t

<400> SEQUENCE: 91
ragghmsmmk mvsmssrnbd ygavgamgg                                    29

<210> SEQ ID NO 92
<211> LENGTH: 48
<212> TYPE: DNA
<213> ORGANISM: Artificial Sequence
<220> FEATURE:
<223> OTHER INFORMATION: DNA motif 2 sequence
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 92
khkdvdrbsw rnbkbhvhbv wbmwtbyygh hsmtrdtbns hdbhbbyw               48

<210> SEQ ID NO 93
<211> LENGTH: 48
<212> TYPE: DNA
```

```
<213> ORGANISM: Artificial Sequence
<220> FEATURE:
<223> OTHER INFORMATION: DNA motif 3 sequence
<220> FEATURE:
<221> NAME/KEY: misc_feature
<222> LOCATION: (4)..(4)
<223> OTHER INFORMATION: n is a, c, g, or t

<400> SEQUENCE: 93
gmkndysmmy tsvvyckbrh ksbybbkmty vrrvhdsysb dvhhbcrw          48

<210> SEQ ID NO 94
<211> LENGTH: 241
<212> TYPE: DNA
<213> ORGANISM: Rhodosporidium toruloides
<220> FEATURE:
<221> NAME/KEY: misc_feature
<222> LOCATION: (23)..(50)
<223> OTHER INFORMATION: DNA motif 1

<400> SEQUENCE: 94
ggtgtactga tgagcggttg cgaggccgca gagcagcgct gcgacgacgg gaagcttcgg     60
cacgagcatg actgtgagta gtagtccaag gagaacagcg cagagtcggc aggagggcac    120
atggaggcag agcgtggggc ggaggaggca gatgggagt cgcgctgggg gacgagaggg     180
tgccgctcga ccaactgctc tctttcgctc ttgctgctgc ttgtactgct cgaacgacgc    240
c                                                                    241

<210> SEQ ID NO 95
<211> LENGTH: 541
<212> TYPE: DNA
<213> ORGANISM: Rhodosporidium toruloides
<220> FEATURE:
<221> NAME/KEY: misc_feature
<222> LOCATION: (323)..(350)
<223> OTHER INFORMATION: DNA motif 1

<400> SEQUENCE: 95
aaggtcgacg ctctcgagtg cccactcgac cgcgttcgtg ggctcaagga agtcctcccc     60
cgtcggctgc gcatcacacg gagcatacgc aacatggaac aagcctccta cgcgtccttg    120
acgcaacttc gggaggtcga catggcctgc aagaccggtc gcaagttcag ggaggacgtc    180
gagcggtctc cggcagaggt ggcgagcgac gtaggggagg tcgacgtgtc cgtctatgag    240
tgggtggcgt ttcaggatcc cgcgggcctc agcgagcaag gactcgttgg gcaaagtgaa    300
ggtgtactga tgagcggttg cgaggccgca gagcagcgct gcgacgacgg gaagcttcgg    360
cacgagcatg actgtgagta gtagtccaag gagaacagcg cagagtcggc aggagggcac    420
atggaggcag agcgtggggc ggaggaggca gatgggagt cgcgctgggg gacgagaggg     480
tgccgctcga ccaactgctc tctttcgctc ttgctgctgc ttgtactgct cgaacgacgc    540
c                                                                    541

<210> SEQ ID NO 96
<211> LENGTH: 1541
<212> TYPE: DNA
<213> ORGANISM: Rhodosporidium toruloides
<220> FEATURE:
<221> NAME/KEY: misc_feature
<222> LOCATION: (1323)..(1350)
<223> OTHER INFORMATION: DNA motif 1

<400> SEQUENCE: 96
aagtctgcta ggtcgtcttc cgtccatcct cgtcgcaaca actccgcaat ctgcagagac     60
```

```
gaggtagtca gcacatgtca tagctgaaga agcaagcgat gcgcaccaag ttcggaaact      120
tcgacgcgtc ctcaagcccc tcaacactcg agcgcatacc gtcaaagtca gacccgagac      180
cgacgtgctt cttgccgcag acggaggcga tgtactcgat atgatcggcg acacggattt      240
gcgtggcgtt cgtagggtcg ataaaggaag ggtagaagac gaccattctg cgagacgcga      300
aggtcagccg gaaacttctg acgacaggaa gtaacgtcgt acgcacacga tgccgtggtt      360
ctggtgctcg cctggcccga tcagctgaag aacttcctct gggacgtttc gcgggtggtc      420
gtggatcgct cgcgcgccag agtgcgagaa gatgacgggc gcaacgctga gttcgagggc      480
ctgctcgcaa atcgtcagct aaagctcgaa agtgttgaag cgcggtgcgc acgtcgagca      540
tggtctgatc gcttgtgtgc gagaggtcga ccatcatgcc gagcctgttc agctccggta      600
caagctcgcg cccgaaggcg gtcaggccgt tcccgtcgtg tacaggctcg ataggagagc      660
cgtccccggc ggaagaggcg aaggctgtga gaaaacccg tcaacagagc ggaagaaggc       720
cgagaggtcg cctcgcctca caagtgtggc aggtgtgcgt gagcgtaagg taccgcacgc      780
cgagttgctg aaagaggcgt aggatggcca gcgagttcat caggtgatgc gagctgtagg      840
aagagcgggt tagcgggagg atgtcggtag agactgttcg tacaaacccc tctagcccaa      900
tcaaggacgc gatcttcccc tccgcgaacg cactccgcac ctcgtccgcc gttcgagcga      960
gcgccatctc ctcaggatag tgctccacca tccgatgaat aaggtcgacg ctctcgagtg     1020
cccactcgac cgcgttcgtg ggctcaagga agtcctcccc cgtcggctgc gcatcacacg     1080
gagcatacgc aacatggaac aagcctccta cgcgtccttg acgcaacttc gggaggtcga     1140
catggcctgc aagaccggtc gcaagttcag ggaggacgtc gagcggtctc cggcagaggt     1200
ggcgagcgac gtaggggagg tcgacgtgtc cgtctatgag tgggtggcgt ttcaggatcc     1260
cgcgggcctc agcgagcaag gactcgttgg gcaaagtgaa ggtgtactga tgagcggttg     1320
cgaggccgca gagcagcgct gcgacgacgg gaagcttcgg cacgagcatg actgtgagta     1380
gtagtccaag gagaacagcg cagagtcggc aggagggcac atggaggcag agcgtgggc      1440 ggaggaggca gatggggagt cgcgctgggg gacgagaggg tgccgctcga ccaactgctc     1500
tctttcgctc ttgctgctgc ttgtactgct cgaacgacgc c                         1541
```

<210> SEQ ID NO 97
<211> LENGTH: 2021
<212> TYPE: DNA
<213> ORGANISM: Rhodosporidium toruloides
<220> FEATURE:
<221> NAME/KEY: misc_feature
<222> LOCATION: (1803)..(1830)
<223> OTHER INFORMATION: DNA motif 1

<400> SEQUENCE: 97

```
cttcccggtc tcgtatcgag cggaagacat cccctcttc ctcgctcaga ttgccgctct        60
cctgcaaggc cagcagtggg gcgtcggtgc gtgcccaact cgtctgaagt ggccaaatgg      120
ctgacagtgc tcccgcaggt cacgacgctg ccgccatcct tcgcggtctt cggcagcgga      180
agctttgatt cttcttgcc tctctcggtt gtacaatcgt cgtgctcgcc agtttgttgt       240
tgatatccct agccttgcct tccatactga acaatctaca actcgtcctt cttgcgcggc     300
ggaaagcgct tcagcacctc gttctgcacg tcttgcggca agtactcccc acccggtcct     360
gcccacatca ccggcagatc tgtccgcttc tcatacactg ctggtgaggc aggttgcgag     420
gcgagagagc gctggaccgc ctcgacttct tccattacgc gaaggaggtt gccgccgatc     480
```

```
aagtctgcta ggtcgtcttc cgtccatcct cgtcgcaaca actccgcaat ctgcagagac      540
gaggtagtca gcacatgtca tagctgaaga agcaagcgat gcgcaccaag ttcggaaact      600
tcgacgcgtc ctcaagcccc tcaacactcg agcgcatacc gtcaaagtca gacccgagac     660
cgacgtgctt cttgccgcag acggaggcga tgtactcgat atgatcggcg acacggattt     720
gcgtggcgtt cgtagggtcg ataaaggaag ggtagaagac gaccattctg cgagacgcga     780
aggtcagccg gaaacttctg acgacaggaa gtaacgtcgt acgcacacga tgccgtggtt     840
ctggtgctcg cctggcccga tcagctgaag aacttcctct gggacgtttc gcgggtggtc     900
gtggatcgct cgcgcgccag agtgcgagaa gatgacgggc gcaacgctga gttcgagggc     960
ctgctcgcaa atcgtcagct aaagctcgaa agtgttgaag cgcggtgcgc acgtcgagca    1020
tggtctgatc gcttgtgtgc gagaggtcga ccatcatgcc gagcctgttc agctccggta    1080
caagctcgcg cccgaaggcg gtcaggccgt tcccgtcgtg tacaggctcg ataggagagc    1140
cgtccccggc ggaagaggcg aaggctgtga gaaaacccg tcaacagagc ggaagaaggc     1200
cgagaggtcg cctcgcctca caagtgtggc aggtgtgcgt gagcgtaagg taccgcacgc    1260
cgagttgctg aaagaggcgt aggatggcca gcgagttcat caggtgatgc gagctgtagg    1320
aagagcgggt tagcgggagg atgtcggtag agactgttcg tacaaacccc tctagcccaa    1380
tcaaggacgc gatcttcccc tccgcgaacg cactccgcac ctcgtccgcc gttcgagcga    1440
gcgccatctc ctcaggatag tgctccacca tccgatgaat aaggtcgacg ctctcgagtg    1500
cccactcgac cgcgttcgtg ggctcaagga agtcctcccc cgtcggctgc gcatcacacg    1560
gagcatacgc aacatggaac aagcctccta cgcgtccttg acgcaacttc gggaggtcga    1620
catggcctgc aagaccggtc gcaagttcag ggaggacgtc gagcggtctc cggcagaggt    1680
ggcgagcgac gtaggggagg tcgacgtgtc cgtctatgag tgggtggcgt ttcaggatcc    1740
cgcgggcctc agcgagcaag gactcgttgg gcaaagtgaa ggtgtactga tgagcggttg    1800
cgaggccgca gagcagcgct gcgacgacgg gaagcttcgg cacgagcatg actgtgagta    1860
gtagtccaag gagaacagcg cagagtcggc aggagggcac atggaggcag agcgtggggc    1920
ggaggaggca gatggggagt cgcgctgggg gacgagaggg tgccgctcga ccaactgctc    1980
tctttcgctc ttgctgctgc ttgtactgct cgaacgacgc c                        2021
```